US008470532B2

(12) United States Patent
Lu et al.

(10) Patent No.: US 8,470,532 B2
(45) Date of Patent: Jun. 25, 2013

(54) APTAMER-BASED COLORIMETRIC SENSOR SYSTEMS

(75) Inventors: Yi Lu, Champaign, IL (US); Juewen Liu, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 13/008,568

(22) Filed: Jan. 18, 2011

(65) Prior Publication Data
US 2011/0236991 A1 Sep. 29, 2011

Related U.S. Application Data

(63) Continuation of application No. 11/202,380, filed on Aug. 11, 2005, now Pat. No. 7,892,734.

(51) Int. Cl.
*C12Q 1/68* (2006.01)
(52) U.S. Cl.
USPC ............................................................ 435/6.1
(58) Field of Classification Search
CPC ............................. C12Q 1/6804; C12Q 1/6813
USPC .................................................. 435/91.2, 6.1
See application file for complete search history.

(56) References Cited

U.S. PATENT DOCUMENTS

| 4,362,603 | A | 12/1982 | Presson et al. |
| 4,703,017 | A | 10/1987 | Campbell et al. |
| 4,746,631 | A | 5/1988 | Clagett |
| 4,855,240 | A | 8/1989 | Rosenstein et al. |
| 4,857,319 | A | 8/1989 | Crowe et al. |
| 5,008,109 | A | 4/1991 | Tin |
| 5,459,040 | A | 10/1995 | Hammock et al. |
| 5,472,881 | A | 12/1995 | Beebe et al. |
| 5,580,967 | A | 12/1996 | Joyce |
| 5,593,835 | A | 1/1997 | Rando et al. |
| 5,631,148 | A | 5/1997 | Urdea |
| 5,663,064 | A | 9/1997 | Burke et al. |
| 5,807,718 | A | 9/1998 | Joyce et al. |
| 5,807,967 | A | 9/1998 | Snow et al. |
| 5,910,408 | A | 6/1999 | Szostak et al. |
| 5,989,813 | A | 11/1999 | Gerdes |
| 6,040,138 | A | 3/2000 | Lockhart et al. |
| 6,110,462 | A | 8/2000 | Barbas et al. |
| 6,159,347 | A | 12/2000 | Sumner, Jr. et al. |
| 6,287,765 | B1 | 9/2001 | Cubicciotti |
| 6,316,194 | B1 | 11/2001 | Karn et al. |
| 6,326,508 | B1 | 12/2001 | Godbole et al. |
| 6,361,944 | B1 | 3/2002 | Mirkin et al. |
| 6,387,617 | B1 | 5/2002 | Asher et al. |
| 6,426,335 | B1 | 7/2002 | Janjic et al. |
| 6,451,535 | B1 | 9/2002 | Jenne et al. |
| 6,485,982 | B1 | 11/2002 | Charlton |
| 6,541,617 | B1 | 4/2003 | Bamdad et al. |
| 6,630,306 | B1 | 10/2003 | Breaker |
| 6,706,474 | B1 | 3/2004 | Lu et al. |
| 6,818,455 | B2 | 11/2004 | May et al. |
| 6,843,890 | B1 | 1/2005 | Godbole |
| 6,849,414 | B2 | 2/2005 | Guan et al. |
| 6,858,608 | B2* | 2/2005 | Mailliet et al. ................ 514/241 |
| 6,890,719 | B2 | 5/2005 | Lu et al. |
| 7,109,165 | B2 | 9/2006 | Matulic-Adamic et al. |
| 7,192,708 | B2 | 3/2007 | Lu et al. |
| 7,332,283 | B2 | 2/2008 | Lu et al. |
| 7,459,145 | B2 | 12/2008 | Bao et al. |
| 7,485,419 | B2 | 2/2009 | Lu et al. |
| 7,534,560 | B2 | 5/2009 | Lu et al. |
| 7,612,185 | B2 | 11/2009 | Lu et al. |
| 7,799,554 | B2 | 9/2010 | Mazumdar et al. |
| 7,829,350 | B2 | 11/2010 | Josephson et al. |
| 7,892,734 | B2 | 2/2011 | Lu et al. |
| 7,902,353 | B2 | 3/2011 | Lu et al. |
| 7,906,320 | B2 | 3/2011 | Lu et al. |
| 2003/0149257 | A1 | 8/2003 | Sorge et al. |
| 2003/0215810 | A1 | 11/2003 | Lu et al. |
| 2003/0235611 | A1 | 12/2003 | Ehringer et al. |
| 2004/0018515 | A1 | 1/2004 | Diener et al. |
| 2004/0126882 | A1 | 7/2004 | Ellington et al. |
| 2004/0158051 | A1 | 8/2004 | Ozkan et al. |
| 2004/0175693 | A1 | 9/2004 | Lu et al. |
| 2004/0180360 | A1* | 9/2004 | Wilson et al. ...................... 435/6 |
| 2005/0037075 | A1 | 2/2005 | Farokhzad et al. |
| 2005/0136500 | A1 | 6/2005 | Yang et al. |
| 2005/0282186 | A1 | 12/2005 | Lu et al. |
| 2006/0019406 | A1 | 1/2006 | Wei et al. |
| 2006/0045910 | A1 | 3/2006 | Ehringer |
| 2006/0094026 | A1 | 5/2006 | Lu et al. |
| 2006/0166222 | A1 | 7/2006 | Lu et al. |
| 2007/0037171 | A1 | 2/2007 | Lu et al. |
| 2007/0269821 | A1 | 11/2007 | Mazumdar et al. |
| 2008/0176228 | A1 | 7/2008 | Lu et al. |
| 2009/0011402 | A1 | 1/2009 | Lu et al. |
| 2009/0029874 | A1 | 1/2009 | Lu et al. |
| 2009/0098550 | A1 | 4/2009 | Lu et al. |
| 2009/0197261 | A1 | 8/2009 | Lu et al. |
| 2010/0105039 | A1 | 4/2010 | Lu et al. |
| 2010/0151579 | A1 | 6/2010 | Wang et al. |

(Continued)

FOREIGN PATENT DOCUMENTS

EP 121970 10/1984
EP 1219708 7/2002

(Continued)

OTHER PUBLICATIONS

Abstract of Joyce, G., "Design and catalytic activity of enzyumic DNA molecules"., (1998).

(Continued)

*Primary Examiner* — Gary Benzion
*Assistant Examiner* — Cynthia Wilder
(74) *Attorney, Agent, or Firm* — Klarquist Sparkman, LLP

(57) ABSTRACT

The present invention provides an aptamer-based colorimetric sensor system for determining the presence and optionally the concentration of an analyte in a sample. Methods of utilizing the sensor system and kits that include the sensor also are provided. The sensor utilizes a linker and oligonucleotide functionalized particles to form an aggregate, which disaggregates in response to the analyte.

30 Claims, 16 Drawing Sheets

U.S. PATENT DOCUMENTS

| | | | |
|---|---|---|---|
| 2010/0166842 | A1 | 7/2010 | Lu et al. |
| 2011/0123982 | A1 | 5/2011 | Lu et al. |
| 2011/0171635 | A1 | 7/2011 | Lu et al. |

FOREIGN PATENT DOCUMENTS

| | | |
|---|---|---|
| EP | 1 312 674 | 5/2003 |
| GB | 2339280 | 1/2000 |
| WO | WO 91/14696 | 10/1991 |
| WO | WO 96/17086 | 6/1996 |
| WO | WO 97/09342 | 3/1997 |
| WO | WO 98/04740 | 2/1998 |
| WO | WO 98/27104 | 6/1998 |
| WO | WO 98/39484 | 9/1998 |
| WO | WO 98/49346 | 11/1998 |
| WO | WO 99/13338 | 3/1999 |
| WO | WO 99/27351 | 6/1999 |
| WO | WO 99/47704 | 9/1999 |
| WO | WO 00/26226 | 5/2000 |
| WO | WO 00/58505 | 10/2000 |
| WO | WO 01/00876 | 1/2001 |
| WO | WO 01/23548 | 4/2001 |
| WO | WO 01/24696 | 4/2001 |
| WO | WO 01/27612 A2 | 4/2001 |
| WO | WO 01/27612 A3 | 4/2001 |
| WO | WO 01/51665 | 7/2001 |
| WO | WO 01/73123 | 10/2001 |
| WO | WO 02/00006 | 1/2002 |
| WO | WO 02/22882 | 3/2002 |
| WO | WO 02/098364 | 12/2002 |
| WO | WO 03/062422 | 7/2003 |
| WO | WO 03/068963 | 8/2003 |
| WO | WO 03/094838 | 11/2003 |
| WO | WO 03/095648 | 11/2003 |
| WO | WO 2004/046687 | 6/2004 |
| WO | 2004/081235 | 9/2004 |
| WO | WO 2005/082922 | 9/2005 |
| WO | WO 2005/095967 | 10/2005 |
| WO | WO 2005/100602 | 10/2005 |
| WO | WO 2006/020768 | 2/2006 |
| WO | WO 2006/020786 | 2/2006 |
| WO | WO 2006/048164 | 5/2006 |
| WO | WO 2006/052419 | 5/2006 |
| WO | WO 2006/078660 | 7/2006 |
| WO | WO 2007/106118 | 9/2007 |
| WO | WO 2007/109500 | 9/2007 |
| WO | WO 2008/089248 | 7/2008 |
| WO | WO 2009/012309 | 1/2009 |
| WO | WO 2009/045632 | 4/2009 |

OTHER PUBLICATIONS

Aggarwal, S.K., et al., "Determination of lead in urine and whole blood by stable isotope dilution gas chromatography-mass spectrometry"., Clinical Chemistry, vol. 40, No. 8, pp. 1494-1502, (1994).
Alivisatos, A.P., et al., "Organization of "nanocrystal molecules" using DNA"., Nature, vol. 382, pp. 609-611, (1996).
Allara, D. et al., "Spontaneously organized molecular assemblies. 1.Formation, dynamics and physical properties of n-alkanoic acids adsorbed from solution on an oxidized aluminum surface"., Langmuir, vol. 1, No. 1, pp. 45-52, (1985).
Andreola, M-L., et al., "DNA aptamers selected against the HIV-1 RNase H display in vitro antiviral activity"., Biochemistry, vol. 40, No. 34, pp. 10087-10094, (2001).
Bain, C. D., et al., "Modeling organic surfaces with self-assembled monolayers"., Angew. Chem. Int. Ed. Engl., vol. 28, No. 4, pp. 506-512, (1989).
Bannon, D.I., et al., "Graphite furnace atomic absorption spectroscopic measurement of blood lead in matrix-matched standards"., Clinical Chemistry, vol. 40, No. 9, pp. 1730-1734, (1994).
Been, M.D., et al., "Self-cleaving ribozymes of hepatitis delta virus RNA"., Eur. J. Biochem., vol. 247, pp. 741-753, (1997).
Berens, C., et al., "A tetracycline-binding RNA aptamer"., Bioorganic & Medicinal Chemistry, vol. 9, pp. 2549-2556, (2001).
Biroccio, A., et al., "Selection of RNA aptamers that are specific and high-affinity ligands of the hepatitis C virus RNA-dependent RNA polymerase"., Journal of Virology, vol. 76, No. 8, pp. 3688-3696, (2002).

Blake, D.A., et al., "Antibody-based sensors for heavy metal ions"., Biosensors & Bioelectronics, vol. 16, pp. 799-809, (2001).
Blank, M., et al., "Systematic evolution of a DNA aptamer binding to rat brain tumor microvessels. Selective targeting of endothelial regulatory protein pigpen"., Journal of Biological Chemistry, vol. 276, No. 19, pp. 16464-16468, (2001).
Bock, L.C., et al., "Selection of single-stranded DNA molecules that bind and inhibit human thrombin"., Nature, vol. 355, pp. 564-566, (1992).
Bogden, J.D., et al., "Soil contamination from lead in paint chips"., Bulletin of Environmental Contamination & Toxicology, vol. 14, No. 3, pp. 289-294, (1975).
Boiziau, C., et al., "DNA aptamers selected against the HIV-1 trans-activation-responsive RNA element form RNA-DNA kissing complexes"., Journal of Biological Chemistry, vol. 274, No. 18, pp. 12730-12737, (1999).
Bowins, R.J., et al., "Electrothermal isotope dilution inductively coupled plasma mass spectrometry method for the determination of sub-ng ml$^{-1}$ levels of lead in human plasma"., Journal of Analytical Atomic Spectrometry, vol. 9, pp. 1233-1236, (1994).
Breaker, R.R., "Catalytic DNA: in training and seeking employment"., Nature Biotechnology, vol. 17, pp. 422-423, (1999).
Breaker, R.R., "DNA aptamers and DNA enzymes" Current Opinion in Chemical Biology, vol. 1, pp. 26-31, (1997).
Breaker, R.R., "DNA enzymes"., Nature Biotechnology, vol. 15, pp. 427-431, (1997).
Breaker, R.R., "Molecular Biology: Making Catalytic DNAs"., Science, vol. 290, issue 5499, pp. 2095-2096, (2000).
Breaker, R.R., et al., "A DNA enzyme that cleaves RNA"., Chemistry & Biology, vol. 1, No. 4, pp. 223-229, (1994).
Breaker, R.R., et al., "A DNA enzyme with $Mg^{2+}$-dependent RNA phosphoesterase activity"., Chemistry & Biology, vol. 2, No. 10, pp. 655-660, (1995).
Breaker, R.R., et al., "Engineered allosteric ribozymes as biosensor components"., Current Opinion in Biotechnology, vol. 13, pp. 31-39, (2002).
Brody, E.N., et al., "Aptamers as therapeutic and diagnostic agents"., Reviews in Molecular Biotechnology, vol. 74, pp. 5-13, (2000).
Broude, N. E., "Stem-loop oligonucleotides: a robust tool for molecular biology and biotechnology", Trends in Biotechnology, vol. 20, No. 6, pp. 249-256, (2002).
Brown, A.K., et al., "A lead-dependent DNAzyme with a two-step mechanism"., Biochemistry, vol. 42, No. 23, pp. 7152-7161, (2003).
Bruesehoff, P.J., et al., "Improving metal ion specificity during In Vitro selection of catalytic DNA"., Combinatorial Chemistry & High Throughput Screening, vol. 5, pp. 327-335, (2002).
Bruno, J.G., et al., "In vitro selection of DNA aptamers to anthrax spores with electrochemiluminescence detection"., Biosensors & Bioelectronics, vol. 14, pp. 457-464, (1999).
Bruno, J.G., et al., "Use of magnetic beads in selection and detection of biotoxin aptamers by electrochemiluminescence and enzymatic methods"., BioTechniques, vol. 32, No. 1, pp. 178-180, pp. 182-183, (2002).
Brust, M., et al., "Novel gold-dithiol nano-networks with non-metallic electronic properties"., Advanced Materials, vol. 7, No. 9, pp. 795-797, (1995).
Burdette, S.C., et al., "Fluorescent Sensors for $Zn^{2+}$ Based on a Fluorescein Platform: Synthesis, Properties and Intracellular Distribution"., J. Am. Chem. Soc., vol. 123, No. 32, pp. 7831-7841, (2001).
Burgstaller, P., et al., "Isolation of RNA aptamers for biological cofactors by in vitro selection"., Angew. Chem. Int. Ed. Engl, vol. 33, No. 10, pp. 1084-1087, (1994).
Burgstaller, P., et al., "Structural probing and damage selection of citrulline- and arginine-specific RNA aptamers identify base positions required for binding"., Nucleic Acids Research, vol. 23, No. 23, pp. 4769-4776, (1995).
Burke, D.H., et al., "A Novel Acidophilic RNA Motif That Recognizes Coenzyme A"., Biochemistry, vol. 37, No. 13, pp. 4653-4663, (1998).
Burke, D.H., et al., "RNA aptamers to the adenosine moiety of S-adenosyl methionine: structural inferences from variations on a theme and the reproducibility of SELEX"., Nucleic Acids Research, vol. 25, No. 10, pp. 2020-2024, (1997).

Burke, D.H., et al., "RNA aptamers to the peptidyl transferase inhibitor chloramphenicol"., Chemistry & Biology, vol. 4, No. 11, pp. 833-843, (1997).
Burmeister, J., et al., "Cofactor-assisted self-cleavage in DNA libraries with a 3'-5'-phosphoramidate bond"., Angew. Chem. Int. Ed. Engl., vol. 36, No. 12, pp. 1321-1324, (1997).
Burwell Jr., R.L., "Modified silica gels as adsorbents and catalysts"., Chemical Technology, 4, pp. 370-377, (1974).
Cadwell, R.C., et al., "Mutagenic PCR"., PCR Methods and Applications, vol. 3, pp. S136-S140, (1994).
Cadwell, R.C., et al., "Randomization of genes by PCR mutagenesis"., PCR Methods and Applications, vol. 2, pp. 28-33, (1992).
Cake, K.M., et al., "In vivo x-ray fluorescence of bone lead in the study of human lead metabolism: serum lead, whole blood lead, bone lead, and cumulative exposure"., Advances in X-Ray Analysis, vol. 38, pp. 601-606, (1995).
Camara Rica, C., et al., "Determination of trace concentrations of lead and nickel in human milk by electrothermal atomisation atomic absorption spectrophotometry and inductively coupled plasma emission spectroscopy"., The Science of the Total Environment, vol. 22, pp. 193-201, (1982).
Cao, Y.W., et al., "DNA-modified core-shell Ag/Au nanoparticles"., J. Am. Chem. Soc., vol. 123, No. 32, pp. 7961-7962, (2001).
Carmi, N., et al., "Cleaving DNA with DNA"., Proc. Natl. Acad. Sci. USA, vol. 95, pp. 2233-2237, (1998).
Carmi, N., et al., "In vitro selection of self-cleaving DNAs"., Chemistry & Biology, vol. 3, No. 12, pp. 1039-1046, (1996).
Cech, T.R., "Structure and mechanism of the large catalytic RNAs: group I and group II introns and ribonuclease P"., The RNA World, pp. 239-269, Cold Spring Harbor Laboratory Press, Cold Spring Harbor, New York, (1993).
Cech, T.R., et al., "Group I ribozymes: substrate recognition, catalytic strategies, and comparative mechanistic analysis"., Nucleic Acids and Molecular Biology, vol. 10, pp. 1-17, (1996).
Chaloin, L., et al., "Endogenous expression of a high-affinity pseudoknot RNA aptamer suppresses replication of HIV-1"., Nucleic Acids Research, vol. 30, No. 18, pp. 4001-4008, (2002).
Chapman, K.B., et al., "In vitro selection of catalytic RNAs"., Current Opinion in Structural Biology, vol. 4, pp. 618-622, (1994).
Chartrand, P., et al., "Effect of structural modifications on the activity of the leadzyme"., Biochemistry, vol. 36, No. 11, pp. 3145-3150, (1997).
Chen, J., et al, "Synthesis from DNA of a molecule with the connectivity of a cube"., Nature, vol. 350, pp. 631-633, (1991).
Chen, C-T., et al., "A highly selective fluorescent chemosensor for lead ions"., J. Am. Chem. Soc., vol. 124, pp. 6246-6247, (2002).
Chen, J-H., et al., "A specific quadrilateral synthesized from DNA branched junctions"., J. Am. Chem. Soc., vol. 111, No. 16, pp. 6402-6407, (1989).
Chen, L., et al., "Crystal structure of a four-stranded intercalated DNA: d($C_4$)"., Biochemistry, vol. 33, No. 46, pp. 13540-13546, (1994).
Chinnapen, D.J.F., et al., "Hemin-stimulated docking of cytochrome c to a hemin-DNA aptamer complex"., Biochemistry, vol. 41, No. 16, pp. 5202-5212, (2002).
Ciesiolka, J., et al., "Selection of an RNA domain that binds $Zn^{2+}$"., RNA, vol. 1, pp. 538-550, (1995).
Ciesiolka, J., et al., "Small RNA-divalent domains"., RNA, vol. 2, pp. 785-793, (1996).
Conaty, J., et al., "Selected classes of minimised hammerhead ribozyme have very high cleavage rates at low $Mg^{2+}$ concentration"., Nucleic Acids Research, vol. 27, No. 11, pp. 2400-2407, (1999).
Conn, M.M., et al., "Porphyrin Metalation Catalyzed by a Small RNA Molecule"., J. Am. Chem. Soc, vol. 118, No. 29, pp. 7012-7013, (1996).
Connell, G.J., et al., "RNAs with dual specificity and dual RNAs with similar specificity"., Science, New Series, vol. 264, issue 5162, pp. 1137-1141, (1994).
Connell, G.J., et al., "Three small ribooligonucleotides with specific arginine sites"., Biochemistry, vol. 32, No. 21, pp. 5497-5502, (1993).

Cuenoud, B., et al., "A DNA metalloenzyme with DNA ligase activity"., Nature, vol. 375, pp. 611-614, (1995).
Czarnik, A.W., "Desperately seeking sensors"., Chemistry & Biology, vol. 2, No. 7, pp. 423-428, (1995).
Dai, X., et al., "Cleavage of an amide bond by a ribozyme"., Science, New Series, vol. 267, issue 5195, pp. 237-240, (1995).
Davis, J.H., et al., "Isolation of high-affinity GTP aptamers from partially structured RNA libraries"., Proc. Natl. Acad. Sci. USA, vol. 99, No. 18, pp. 11616-11621, (2002).
Davis, K.A., et al., "Staining of cell surface human CD4 with 2'-F-pyrimidine-containing RNA aptamers for flow cytometry"., Nucleic Acids Research, vol. 26, No. 17, pp. 3915-3924, (1998).
Definition of the word "ion" printed from Merriam-Webster online dictionary (www.m-w.com) on Jun. 30, 2004.
Definition of the word "particle" printed from Merriam-Webster online dictionary (www.m-w.com) on Jun. 29, 2004.
Deo, S., et al., "A Selective, Ratiometric Fluorescent Sensor for $Pb^{2+}$"., J. Am. Chem. Soc., vol. 122, No. 1, pp. 174-175, (2000).
Derose, V.J., "Two Decades of RNA Catalysis"., Chemistry & Biology, vol. 9, pp. 961-969, (2002).
Didenko, V.V., "DNA probes using fluorescence resonance energy transfer (FRET): Designs and applications"., BioTechniques, vol. 31, pp. 1106-1121, (2001).
Doudna, J.A., et al., "The Chemical Repertoire of Natural Ribozymes"., Nature, vol. 418, pp. 222-228, (2002).
Dubois, L.H., et al., "Synthesis, structure, and properties of model organic surfaces"., Annu. Rev. Phys. Chem., vol. 43, pp. 437-463, (1992).
Earnshaw, D.J., et al., "Modified oligoribonucleotides as site-specific probes of RNA structure and function"., Biopolymers (Nucleic Acid Sciences), vol. 48, pp. 39-55, (1998).
Ekland, E.H., et al., "RNA-catalysed RNA polymerization using nucleoside triphosphates"., Nature, vol. 382, pp. 373-376, (1996).
Ekland, E.H., et al., "Structurally complex and highly active RNA ligases derived from random RNA sequences"., Science, vol. 269, issue 5222, pp. 364-370, (1995).
Elghanian, R., et al., "Selective colorimetric detection of polynucleotides based on the distance-dependent optical properties of gold nanoparticles"., Science, vol. 277, pp. 1078-1081, (1997).
Ellington, A.D., et al., "Aptamers as potential nucleic acid pharmaceuticals"., Biotechnology Annual Review, vol. 1, pp. 185-214, (1995).
Ellington, A.D., et al., "In vitro selection of RNA molecules that bind specific ligands"., Nature, vol. 346, pp. 818-822, (1990).
Ellington, A.D., et al., "Selection in vitro of single-stranded DNA molecules that fold into specific ligand-binding structures"., Nature, vol. 355, pp. 850-852, (1992).
Famulok, M., "Molecular Recognition of Amino Acids by RNA-Aptamers: An L-Citrulline Binding RNA Motif and Its Evolution into an L-Arginine Binder"., J. Am. Chem. Soc., vol. 116, No. 5, pp. 1698-1706, (1994).
Famulok, M., "Oligonucleotide aptamers that recognize small molecules", Current Opinion in Structural Biology, vol. 9, pp. 324-329, (1999).
Famulok, M., et al., "In Vitro Selection Analysis of Neomycin Binding RNAs with a Mutagenized Pool of Variants of the 16S rRNA Decoding Region"., Biochemistry, vol. 35, No. 14, pp. 4265-4270, (1996).
Famulok, M., et al., "Stereospecific recognition of tryptophan agarose by in vitro selected RNA"., J. Am. Chem. Soc., vol. 114, No. 10, pp. 3990-3991, (1992).
Faulhammer, D., et al., "Characterization and Divalent Metal-ion Dependence of in Vitro Selected Deoxyribozymes which Cleave DNA/RNA Chimeric Oligonucleotides"., J. Mol. Biol., vol. 269, pp. 188-202, (1997).
Faulhammer, D., et al., "The $Ca^{2+}$ ion as a cofactor for a novel RNA-cleaving deoxyribozyme"., Angew. Chem., Int. Ed. Engl., vol. 35, No. 23/24, pp. 2837-2841, (1996).
Feldman, B.J., et al., "Determination of lead in blood by square wave anodic stripping voltammetry at a carbon disk ultramicroelectrode"., Analytical Chemistry, vol. 66, No. 13, pp. 1983-1987, (1994).

Ferguson, A., et al., "A novel strategy for selection of allosteric ribozymes yields riboreporter™ sensors for caffeine and aspartame"., Nucleic Acids Research, vol. 32, No. 5, pp. 1756-1766, (2004).

Fodor, S.P.A., et al., "Light-directed, spatially addressable parallel chemical synthesis"., Science, New Series, vol. 251, issue 4995, pp. 767-773, (1991).

Frank, D.N., et al., "In vitro selection for altered divalent metal specificity in the RNase P RNA"., Proc. Natl. Acad. Sci. USA, vol. 94, pp. 14355-14360, (1997).

Frens, G., et al., "Controlled Nucleation for the regulation of the particle size in monodisperse gold suspensions"., Nature Physical Science, vol. 241, pp. 20-22, (1973).

Fukusaki, E-I., et al., "DNA aptamers that bind to chitin"., Bioorganic & Medicinal Chemistry letters, vol. 10, pp. 423-425, (2000).

Geiger, A., et al., "RNA aptamers that bind L-arginine with sub-micromolar dissociation constants and high enantioselectivity"., Nucleic Acids Research, vol. 24, No. 6, pp. 1029-1036, (1996).

Geyer, C.R., et al., "Evidence for the metal-cofactor independence of an RNA phosphodiester-cleaving DNA enzyme"., Chemistry & Biology, vol. 4, No. 8, pp. 579-593, (1997).

Geyer, C.R., et al., "Lanthanide Probes for a Phosphodiester-cleaving, Lead-dependent, DNAzyme", J. Mol. Biol., vol. 275, pp. 483-489, (1998).

Giver, L., et al., "Selection and design of high-affinity RNA ligands for HIV-1 Rev"., Gene, vol. 137, pp. 19-24, (1993).

Giver, L., et al., "Selective optimization of the Rev-binding element of HIV-1".,Nucleic Acids Research, vol. 21, No. 23, pp. 5509-5516, (1993).

Godwin, H.A., et al., "A Flourescent Zinc Probe Based on Metal-Induced Peptide Folding"., J. Am. Chem. Soc., vol. 118, pp. 6514-6515, (1996).

Grabar, K., et al., "Preparation and characterization of Au colloid Monolayers"., Analytical chemistry, vol. 67, No. 4, pp. 735-743, (1995).

Granadillo, V.A., et al., "The influence of the blood levels of lead, aluminum and vanadium upon the arterial hypertension"., Clinica Chimica Acta, vol. 233, pp. 47-59, (1995).

Grate, D., et al., "Laser-mediated, site-specific inactivation of RNA transcripts"., Proc. Natl. Acad. Sci. USA, vol. 96, pp. 6131-6136, (1999).

Guschin, D., et al., "Manual manufacturing of oligonucleotide, DNA, and protein microchips"., Analytical Biochemistry, vol. 250, pp. 203-211, (1997).

Haller, A.A., et al., "In vitro selection of a 7-methyl-guanosine binding RNA that inhibits translation of capped mRNA molecules"., Proc. Natl. Acad. Sci. USA, vol. 94, pp. 8521-8526, (1997).

Harada, K., et al., "Identification of two novel arginine binding DNAs"., The EMBO Journal, vol. 14, No. 23, pp. 5798-5811, (1995).

Hartig, J.S., et al., "Reporter ribozymes for real-time analysis of domain-specific interactions in biomolecules: HIV-1 reverse transcriptase and the primer-template complex"., Angew. Chem. Int. Ed., vol. 41, No. 22, pp. 4263-4266, (2002).

He, X-x., et al., "Bioconjugated nanoparticles for DNA protection from cleavage"., J. Am. Chem. Soc., vol. 125, No. 24, pp. 7168-7169, (2003).

Hennrich, G., et al., "Redox switchable fluorescent probe selective for either Hg(II) or Cd(II) and Zn(II)" J. Am. Chem. Soc., vol. 121, No. 21, pp. 5073-5074, (1999).

Hesselberth, J., et al., "In vitro selection of nucleic acids for diagnostic applications"., Reviews in Molecular Biotechnology, vol. 74, pp. 15-25, (2000).

Hesselberth, J.R., et al., "Simultaneous detection of diverse analytes with an aptazyme ligase array", Analytical Biochemistry vol. 312, pp. 106-112, (2003).

Ho, H-A., et al., "Optical sensors based on hybrid aptamer/conjugated polymer complexes"., J. Am. Chem. Soc., vol. 126, No. 5, pp. 1384-1387, (2004).

Hock, B., "Antibodies for immunosensors, A review"., Analytica Chimica Acta, vol. 347, pp. 177-186, (1997).

Hofmann, H.P., et al., "$Ni^{2+}$-binding RNA motifs with an asymmetric purine-rich internal loop and a G-A base pair"., RNA, vol. 3, pp. 1289-1300, (1997).

Holeman, L.A., et al., "Isolation and characterization of fluorophore-binding RNA aptamers"., Folding & Design, vol. 3, pp. 423-431, (1998).

Hoogstraten, C.G., et al., "NMR solution structure of the lead-dependent ribozyme: Evidence for dynamics in RNA catalysis"., J. Mol. Biol., vol. 284, pp. 337-350, (1998).

Hoogstraten, C.G., et al., "Structural analysis of metal ion ligation to nucleotides and nucleic acids using pulsed EPR spectroscopy"., J. Am. Chem. Soc., vol. 124, No. 5, pp. 834-842, (2002).

Huizenga, D.E., et al., "A DNA aptamer that binds adenosine and ATP"., Biochemistry, vol. 34, No. 2, pp. 656-665, (1995).

Iler, R.K., "The Chemistry of Silica: Solubility, Polymerization, Colloid and Surface Properties, and Biochemistry, Chapter 6, The surface chemistry of silica"., pp. 622-729, A Wiley-Interscience Publication, New York, (1979).

Illangasekare, M., et al., "Small-molecule-substrate interactions with a self-aminoacylating ribozyme"., J. Mol. Biol., vol. 268, pp. 631-639, (1997).

Imperiali, B., et al., "Peptide platforms for metal ion sensing"., Proc. SPIE—The international society for optical engineering, vol. 3858, pp. 135-143, (1999).

International Search Report dated Jan. 15, 2003 for corresponding PCT application No. PCT/US01/20557.

International Search Report dated Aug. 1, 2003 for corresponding PCT application No. PCT/US03/08483.

Iqbal, S.S., et al., "A review of molecular recognition technologies for detection of biological threat agents"., Biosensors & Bioelectronics, vol. 15, pp. 549-578, (2000).

Jagner, D., et al., "Determination of lead in microliter amounts of whole blood by stripping potentiometry"., Electroanalysis, vol. 6, pp. 285-291, (1994).

Jayasena, S.D., "Aptamers: an emerging class of molecules that rival antibodies in diagnostics"., Clinical Chemistry, vol. 45, No. 9, pp. 1628-1650, (1999).

Jenison, R., et al., "Interference-based detection of nucleic acid targets on optically coated silicon", Nature Biotechnology, vol. 19, pp. 62-65, (2001).

Jenison, R.D., et al., "High-resolution molecular discrimination by RNA"., Science, vol. 263, pp. 1425-1429, (1994).

Jenne, A., et al., "Rapid Identification and Characterization of Hammerhead-Ribozyme Inhibitors Using Fluorescence-Based Technology"., Nature Biotechnology, vol. 19, pp. 56-61, (2001).

Jenne, A., et al., "Real-time Characterization of Ribozymes by Fluorescence Resonance Energy Transfer (FRET)"., Angewandte Chemie. International Edition, vol. 38, No. 9, pp. 1300-1303, (1999).

Jhaveri, S., et al., "In vitro selection of signaling aptamers"., Nature Biotechnology, vol. 18, pp. 1293-1297, (2000).

Jhaveri, S.D., et al., "Designed signaling aptamers that transduce molecular recognition to changes in fluorescence intensity"., J. Am. Chem. Soc., vol. 122, No. 11, pp. 2469-2473, (2000).

Jin, R., et al., "What controls the melting properties of DNA-linked gold nanoparticle assemblies?"., J. Am. Chem. Soc., vol. 125, No. 6, pp. 1643-1654, (2003).

Joos, B., et al., "Covalent attachment of hybridizable oligonucleotides to glass supports"., Analytical Biochemistry, vol. 247, pp. 96-101, (1997).

Josephson, L., et al., "Magnetic nanosensors for the detection of oligonucleotide sequences"., Angewandte Chemie. International Edition, vol. 40, No. 17, pp. 3204-3206, (2001).

Joyce, G.F., "Appendix 3: Reactions Catalyzed by RNA and DNA Enzymes". The RNA World, vol. 37, pp. 687-690, Cold Spring Harbor Laboratory Press, Cold Spring Harbor, New York, (1999).

Joyce, G.F., "In vitro evolution of nucleic acids"., Current Opinion in Structural Biology, vol. 4, pp. 331-336, (1994).

Katahira, M., et al., "Two metal-binding sites in a lead ribozyme bound to competitively by $Pb^{2+}$ and $Mg^{2+}$: Induced structural changes as revealed by NMR"., European Journal of Biochemistry, vol. 255, pp. 727-733, (1998).

Kato, T., et al., "In vitro selection of DNA aptamers which bind to cholic acid"., Biochimica et Biophysica Acta, vol. 1493, pp. 12-18, (2000).

Kawakami, J., et al., "In vitro selection of aptamers that act with $Zn^{2+}$"., Journal of Inorganic Biochemistry, vol. 82, pp. 197-206, (2000).

Khan, R., et al., "Interaction of retroviral nucleocapsid proteins with transfer $RNA^{Phe}$: a lead ribozyme and $^1H$ NMR study"., Nucleic Acids Research, vol. 24, No. 18, pp. 3568-3575, (1996).

Khosraviani, M., et al., "Detection of heavy metals by immunoassay: Optimization and validation of a rapid, portable assay for ionic cadmium"., Environ. Sci. Technol., vol. 32, No. 1, pp. 137-142, (1998).

Kiga, D., et al., "An RNA aptamer to the xanthine/guanine base with a distinctive mode of purine recognition"., Nucleic Acids Research, vol. 26, No. 7, pp. 1755-1760, (1998).

Kim, M.H., et al., "Activation and repression of the activity of a lead ribozyme by the combination of $Pb^{2+}$ and $Mg^{2+1}$"., J. Biochem., vol. 122, No. 5, pp. 1062-1067, (1997).

Kluβmann, S., et al., "Mirror-image RNA that binds D-adenosine"., Nature Biotechnology, vol. 14, pp. 1112-1115, (1996).

Kohama, T., et al., "Molecular Cloning and Functional Characterization of Murine Sphingosine Kinase", The Journal of Biological Chemistry, vol. 273, No. 37, pp. 23722-23728, (1998).

Koizumi, M., et al., "Allosteric selection of ribozymes that respond to the second messengers cGMP and cAMP"., Nature Structural Biology, vol. 6, No. 11, pp. 1062-1071, (1999).

Koizumi, M., et al., "Molecular Recognition of cAMP by an RNA Aptamer"., Biochemistry, vol. 39, No. 30, pp. 8983-8992, (2000).

Koizumi, M., et al., "Allosteric ribozymes sensitive to the second messengers cAMP and cGMP"., Nucleic Acids Symposium Series, No. 42, pp. 275-276, (1999).

Kruger, K., et al., "Self-splicing RNA: autoexcision and autocyclization of the ribosomal RNA intervening sequence of the Tetrahymena"., Cell, vol. 31, pp. 147-157, (1982).

Lato, S.M., et al., "In vitro selection of RNA lectins: Using combinatorial chemistry to interpret ribozyme evolution"., Chemistry & Biology, vol. 2, No. 5, pp. 291-303, (1995).

Lauhon, C.T., et al., "RNA aptamers that bind flavin and nicotinamide redox cofactors"., J. Am. Chem. Soc., vol. 117, No. 4, pp. 1246-1257, (1995).

Lebruska, L.L., "Selection and Characterization of an RNA Decoy for Transcription Factor NF-κB"., Biochemistry, vol. 38, No. 10, pp. 3168-3174, (1999).

Lee, M., et al., "A fiber-optic microarray biosensor using aptamers as receptors"., Analytical Biochemistry, vol. 282, pp. 142-146, (2000).

Lee, S-W., et al., "Ordering of quantum dots using genetically engineered viruses"., Science, vol. 296, pp. 892-895, (2002).

Legault, P., et al., "Order, dynamics and metal-binding in the lead-dependent ribozyme"., J. Mol. Biol., vol. 284, pp. 325-335, (1998).

Lehman, N., et al., "Evolution in vitro of an RNA enzyme with altered metal dependence"., Nature, vol. 361, pp. 182-185, (1993).

Lemieux, S., et al., "Modeling active RNA structures using the intersection of conformational space: application to the lead-activated ribozyme"., RNA, vol. 4, pp. 739-749, (1998).

Levy, M., et al., "ATP-Dependent Allosteric DNA Enzymes"., Chemistry & Biology, vol. 9, pp. 417-426, (2002).

Li, J., et al., "A highly sensitive and selective catalytic DNA biosensor for lead ions"., J. Am. Chem. Soc., vol. 122, No. 42, pp. 10466-10467, (2000).

Li, J., et al., "In vitro selection and characterization of a highly efficient Zn(II)-dependent RNA-cleaving deoxyribozyme"., Nucleic Acids Research, vol. 28, No. 2, pp. 481-488, (2000).

Li, J.J., et al., "Using molecular beacons as a sensitive fluorescence assay for enzymatic cleavage of single-stranded DNA"., Nucleic Acids Research, vol. 28, No. 11, e52, pp. i-vi, (2000).

Li, Y., et al., "A catalytic DNA for porphyrin metallation"., Nature Structural Biology, vol. 3, No. 9, pp. 743-747, (1996).

Li, Y., et al., "Capping DNA with DNA"., Biochemistry, vol. 19, No. 11, pp. 3106-3114, (2000).

Li, Y., et al., "Deoxyribozymes: new players in the ancient game of biocatalysis"., Current Opinion in Structural Biology, vol. 9, pp. 315-323, (1999).

Li, Y., et al., "Phosphorylating DNA with DNA"., Proc. Natl. Acad. Sci. USA, vol. 96, pp. 2746-2751, (1999).

Link, S., et al., "Alloy formation of gold-silver nanoparticles and the dependence of the plasmon absorption on their composition"., J. Phys. Chem. B, vol. 103, No. 18, pp. 3529-3533, (1999).

Liu, H-W., et al., "Determination of cadmium, mercury and lead in seawater by electrothermal vaporization isotope dilution inductively coupled plasma mass spectrometry"., Spectrochimica Acta Part B Atomic Spectroscopy 54, pp. 1367-1375, (1999).

Liu, J., et al., "A colorimetric lead biosensor using DNAzyme-directed assembly of gold nanoparticles", J. Am. Chem. Soc., vol. 125, No. 22, pp. 6642-6643, (2003).

Liu, J., et al., "Accelerated color change of gold nanoparticles assembled by DNAzymes for simple and fast colorimetric $Pb^{2+}$ detection"., J. Am. Chem. Soc., vol. 126, No. 39, pp. 12298-12305, (2004).

Liu, J., et al., "Adenosine-dependent assembly of aptazyme-functionalized gold nanoparticles and its application as a colorimetric biosensor"., Analytical Chemistry, vol. 76, No. 6, pp. 1627-1632, (2004).

Liu, J., et al., "Colorimetric biosensors based on DNAzyme-assembled gold nanoparticles"., Journal of Fluorescence, vol. 14, No. 4, pp. 343-354, (2004).

Liu, J., et al., "Highly dispersible molecular sieve carbon nanoparticles"., Chem. Mater., vol. 16, No. 22, pp. 4205-4207, (2004).

Liu, X., et al., "A fiber-optic evanescent wave DNA biosensor based on novel molecular beacons"., Analytical Chemistry, vol. 71, No. 22, pp. 5054-5059, (1999).

Liu, Z., et al., "Assemblage of signaling DNA enzymes with intriguing metal-ion specificities and pH dependences"., J. Am. Chem. Soc., vol. 125, No. 25, pp. 7539-7545, (2003).

Lohse, P.A., et al., "Ribozyme-catalysed amino-acid transfer reactions"., Nature, vol. 381, pp. 442-444, (1996).

Lorsch, J.R., et al., "In vitro evolution of new ribozymes with polynucleotide kinase activity"., Nature, vol. 371, pp. 31-36, (1994).

Lorsch, J.R., et al., "In vitro selection of RNA aptamers specific for cyanocobalamin"., Biochemistry, vol. 33, No. 4, pp. 973-982, (1994).

Lott, W.B., et al., "A two-metal ion mechanism operates in the hammerhead ribozyme-mediated cleavage of an RNA substrate"., Proc. Natl. Acad. Sci. USA, vol. 95, pp. 542-547, (1998).

Lu, Y., "New transition-metal-dependent DNAzymes as efficient endonucleases and as selective metal biosensors"., Chem. Eur. J., vol. 8, No. 20, pp. 4589-4596, (2002).

Lu, Y., et al., "New fluorescent and colorimetric DNAzyme biosensors for metal ions", Journal of Inorganic Biochemistry, vol. 96, issue 1, pp. 30, Abstract of the 11th International Conference on Biological Inorganic Chemistry; (Jul. 15, 2003).

Majerfeld, I., et al., "An RNA pocket for an aliphatic hydrophobe"., Structural Biology, vol. 1, No. 5, pp. 287-292, (1994).

Majerfeld, I., et al., "Isoleucine:RNA sites with associated coding sequences"., RNA, vol. 4, pp. 471-478, (1998).

Mannironi, C., et al., "In vitro selection of dopamine RNA ligands"., Biochemistry, vol. 36, No. 32, pp. 9726-9734, (1997).

Maoz, R., et al., "Penetration-controlled reactions in organized monolayer assemblies. 1. Aqueous permanganate interaction with monolayer and multilayer films of long-chain surfactants"., Langmuir, vol. 3, No. 6, pp. 1034-1044, (1987).

Marcus, A.H., et al., "Estimating the contribution of lead based paint to soil lead, dust lead, and childhood blood lead"., American Society for Testing and Materials Spec. STP 1226, pp. 12-23, (1995).

Marsh, T.C., et al., "A new DNA nanostructure, the G-wire, imaged by scanning probe microscopy"., Nucleic Acids Research, vol. 23, No. 4, pp. 696-700, (1995).

Matteucci, M.D., et al., "Synthesis of Deoxyoligonucleotides on a polymer support"., J. Am. Chem. Soc., vol. 103, No. 11, pp. 3185-3191, (1981).

Mecklenburg, M., et al., "A strategy for the broad range detection of compounds with affinity for nucleic acids"., Analytica Chimica Acta, vol. 347, pp. 79-86, (1997).

Mei, S.H.J., et al., "An efficient RNA-cleaving DNA enzyme that synchronizes catalysis with fluorescence signaling"., J. Am. Chem. Soc., vol. 125, No. 2, pp. 412-420, (2003).

Meli, M., et al., "Adenine-aptamer complexes: A bipartite RNA site that binds the adenine nucleic base"., The Journal of Biological Chemistry, vol. 277, No. 3, pp. 2104-2111, (2002).

Mirkin, C.A., et al., "A DNA-based method for rationally assembling nanoparticles into macroscopic materials"., Nature, vol. 382, pp. 607-609, (1996).

Mirkin, S.M., et al., "H-DNA and related structures"., Annu. Rev. Biophys. Biomol. Struct., vol. 23, pp. 541-576, (1994).

Miyawaki, A., et al. "Fluorescent indicators for $Ca^{2+}$ based on green fluorescent proteins and calmodulin"., Nature, vol. 388, pp. 882-887, (1997).

Mucic, R.C., et al., "Synthesis and characterization of DNA with ferrocenyl groups attached to their 5'-termini: electrochemical characterization of a redox-active nucleotide monolayer"., Chem. Commun., pp. 555-557, (1996).

Mullah, B., et al., "Automated synthesis of double dye-labeled oligonucleotides using tetramethylrhodamine (TAMRA) solid supports"., Tetrahedron Letters, vol. 38, No. 33, pp. 5751-5754, (1997).

Nazarenko, I.A., et al., "A closed tube format for amplification and detection of DNA based on energy transfer"., Nucleic Acids Research, vol. 26, No. 12, pp. 2516-2521, (1997).

Nazarenko, I.A., et al., "Defining a Smaller RNA Substrate for Elongation Factor Tu"., Biochemistry, vol. 34, No. 8, pp. 2545-2552, (1995).

Niemeyer, C.M., "Nanoparticles, proteins, and nucleic acids: Biotechnology meets materials science"., Angew. Chem. Int. Edition, vol. 40, pp. 4128-4158, (2001).

Nieuwlandt, D., et al., "In Vitro Selection of RNA Ligands to Substance P"., Biochemistry, vol. 34, No. 16, pp. 5651-5659, (1995).

Nissen, P., et al., "The structural basis of ribosome activity in peptide bond synthesis"., Science, vol. 289, pp. 920-930, (2000).

Nolte, A., et al., "Mirror-design of L-oligonucleotide ligands binding to L-arginine"., Nature Biotechnology, vol. 14, pp. 1116-1119, (1996).

Nutiu, R., et al., "Structure-switching signaling aptamers"., J. Am. Chem. Soc., vol. 125, No. 16, pp. 4771-4778, (2003).

Nuzzo, R.G., et al., "Spontaneously organized molecular assemblies. 3. Preparation and properties of solution adsorbed monolayers of organic disulfides on gold surfaces"., J. Am. Chem. Soc., vol. 109, No. 8, pp. 2358-2368, (1987).

O'Donnell, M.J., et al., "High-Density, Covalent Attachment of DNA to Silicon Wafers for Analysis by MALDI-TOF Mass Spectrometry"., Analytical Chemistry, vol. 69, No. 13, pp. 2438-2443, (1997).

Oehme, I., et al., "Optical sensors for determination of heavy metal ions"., Mikrochim. Acta, vol. 126, pp. 177-192, (1997).

Ohmichi, T., et al., "Role of $Nd^{3+}$ and $Pb^{2+}$ on the RNA cleavage reaction by a small ribozyme"., Biochemistry, vol. 36, No. 12, pp. 3514-3521, (1997).

Ohmichi, T., et al., "Effect of substrate RNA sequence on the cleavage reaction by a short ribozyme"., Nucleic Acids Research, vol. 26, No. 24, pp. 5655-5661, (1998).

Okazawa, A., et al., "In vitro selection of hematoporphyrin binding DNA aptamers"., Bioorganic & Medicinal Chemistry, Letters 10, pp. 2653-2656, (2000).

Ota, N., et al., "Effects of helical structures formed by the binding arms of DNAzymes and their substrates on catalytic activity"., Nucleic Acids Research, vol. 26, No. 14, pp. 3385-3391, (1998).

Pan, T., et al., "A small metalloribozyme with a two-step mechanism"., Nature, vol. 358, pp. 560-563, (1992).

Pan, T., et al., "In vitro selection of RNAs that undergo autolytic cleavage with $Pb^{2+}$"., Biochemistry, vol. 31, No. 16, pp. 3887-3895, (1992).

Pan, T., et al., "Properties of an in vitro selected $Pb^{2+}$ cleavage motif"., Biochemistry, vol. 33, No. 32, pp. 9561-9565, (1994).

Pan, W., et al., "Isolation of virus-neutralizing RNAs from a large pool of random sequences"., Proc. Natl. Acad. Sci. USA, vol. 92, pp. 11509-11513, (1995).

Park, S-J., et al., "Array-based electrical detection of DNA with nanoparticle probes"., Science, vol. 295, pp. 1503-1506, (2002).

Parsons, P.J., et al., "A rapid Zeeman graphite furnace atomic absorption spectrometric method for the determination of lead in blood"., Spectrochimica Acta, vol. 48B, No. 6/7, pp. 925-939, (1993).

Pavlov, A.R., et al., "Determination of lead in environmental water samples by a rapid and portable immunoassay"., ANYL, Book of Abstracts, 219th ACS National Meeting, San Francisco, CA, Mar. 26-30, 2000.

Pavlov, V., et al., "Aptamer-functionalized Au nanoparticles for the amplified optical detection of thrombin"., J. Am. Chem. Soc., vol. 126, No. 38, pp. 11768-11769, (2004).

Pearce, D.A., et al., "Peptidyl chemosensors incorporating a FRET mechanism for detection of Ni(II)"., Bioorganic & Medicinal Chemistry, Letters 8, pp. 1963-1968, (1998).

Pease, A.C., et al., "Light-generated oligonucleotide arrays for rapid DNA sequence analysis"., Proc. Natl. Acad. Sci. USA, vol. 91, pp. 5022-5026, (1994).

Piccirilli, J.A., et al., "Aminoacyl esterase activity of the tetrahymena ribozyme"., Science, New Series, vol. 256, issue 5062, pp. 1420-1424, (1992).

Pley, H.W., et al., "Three-dimensional structure of a hammerhead ribozyme"., Nature, vol. 372, pp. 68-74, (1994).

Potyrailo, R.A., et al., "Adapting selected nucleic acid ligands (aptamers) to biosensors"., Analytical Chemistry, vol. 70, No. 16, pp. 3419-3425, (1998).

Prudent, J.R., et al., "Expanding the scope of RNA catalysis"., Science, New Series, vol. 264, issue 5167, pp. 1924-1927, (1994).

Qiao, H., et al., "Transferability of blood lead determinations by furnace atomic absorption spectrophotometry and continuum background correction"., Clinical Chemistry, vol. 41, No. 10, pp. 1451-1454, (1995).

Rabinowitz, M., et al., "Home refinishing, lead paint, and infant blood lead levels"., American Journal of Public Health, vol. 75, No. 4, pp. 403-404, (1985).

Rajendran, M., et al., "Selecting nucleic acids for biosensor applications"., Combinatorial Chemistry and High Throughput Screening, vol. 5, No. 4, pp. 263-270, (2002).

Rakow, N.A., et al., "A colorimetric sensor array for odour visualization"., Nature, vol. 406, pp. 710-713, (2000).

Rink, S.M., et al., "Creation of RNA molecules that recognize the oxidative lesion 7,8-dihydro-8-hydroxy-2'-deoxyguanosine (8-oxodG) in DNA"., Proc. Natl. Acad. Sci. USA, vol. 95, pp. 11619-11624, (1998).

Robertson, M.P., et al., "Design and optimization of effector-activated ribozyme ligases"., Nucleic Acids Research, vol. 28, No. 8, pp. 1751-1759, (2000).

Robertson, M.P., et al., "In vitro selection of an allosteric ribozyme that transduces analytes to amplicons"., Nature Biotechnology, vol. 17, pp. 62-66, (1999).

Roth, A., et al., "An amino acid as a cofactor for a catalytic polynucleotide"., Proc. Natl. Acad. Sci. USA, vol. 95, pp. 6027-6031, (1998).

Roychowdhury-Saha, M., et al., "Flavin Recognition by an RNA Aptamer Targeted toward FAD"., Biochemistry, vol. 41, No. 8, pp. 2492-2499, (2002).

Ruckman, J., et al., "2'-Fluoropyrimidine RNA-based aptamers to the 165-amino acid form of vascular endothelial growth factor ($VEGF_{165}$) Inhibition of receptor binding and VEGF-induced vascular permeability through interactions requiring the exon 7-encoded domain"., The Journal of Biological Chemistry, vol. 273, No. 32, pp. 20556-20567, (1998).

Rurack, K., et al., "A selective and sensitive fluoroionophore for $Hg^{II}$, $Ag^{I}$, and $Cu^{II}$ with virtually decoupled fluorophore and receptor units"., J. Am. Chem. Soc., vol. 122, No. 5, pp. 968-969, (2000).

Rusconi, C.P., et al., "RNA aptamers as reversible antagonists of coagulation factor Ixa"., Nature, vol. 419, pp. 90-94, (2002).

Sabanayagam, C.R., et al., "Oligonucleotide immobilization on micropatterened streptavidin surfaces"., Nucleic Acids Research, vol. 28, No. 8, e33, pp. i-iv, (2000).

Santoro, S.W. et al., "Mechanism and utility of an RNA-cleaving DNA enzyme"., Biochemistry, vol. 37, No. 38, pp. 13330-13342, (1998).

Santoro, S.W., et al., "A general purpose RNA-cleaving DNA enzyme"., Proc. Natl. Acad. Sci. USA, vol. 94, pp. 4262-4266, (1997).

Santoro, S.W., et al., "RNA Cleavage by a DNA Enzyme with Extended Chemical Functionality"., J. Am. Chem. Soc., vol. 122, No. 11, pp. 2433-2439, (2000).
Sassanfar, M., et al., "An RNA motif that binds ATP"., Nature, vol. 364, pp. 550-553, (1993).
Schwartz, J., et al., "The risk of lead toxicity in homes with lead paint hazard"., Environmental Research, vol. 54, No. 1, pp. 1-7, (1991).
Scott, W.G., et al., "The crystal structure of an all-RNA hammerhead ribozyme: A proposed mechanism for RNA catalytic cleavage"., Cell, vol. 81, pp. 991-1002, (1995).
Scott, W.G., "RNA catalysis"., Current Opinion in Structural Biology, vol. 8, pp. 720-726, (1998).
Search results of key word search of medline, Mar. 26, 2000.
Search results of key word search on Chemical Abstracts, Mar. 24, 2000.
Search results of key word search from various databases, Mar. 24, 2000.
Seeman, N.C., et al., "Synthetic DNA knots and catenanes"., New Journal of Chemistry, vol. 17, pp. 739-755, (1993).
Seeman, N.C., et al., "Emulating biology: Building nanostructures from the bottom up"., Proc. Natl. Acad. Sci., vol. 99, suppl. 2, pp. 6451-6455, (2002).
Seeman, N.C., "DNA in a material world"., Nature, vol. 421, pp. 427-431, (2003).
Seetharaman, S., et al., "Immobilized RNA switches for the analysis of complex chemical and biological mixtures"., Nature Biotechnology, vol. 19, pp. 336-341, (2001).
Sen, D., et al., "DNA enzymes"., Current Opinion in Chemical Biology, vol. 2, pp. 680-687, (1998).
Shaiu, W-L., et al., "Atomic force microscopy of oriented linear DNA molecules labeled with 5nm gold spheres"., Nucleic Acids Research, vol. 21, No. 1, pp. 99-103, (1993).
Shaw, S.Y., et al., "Knotting of a DNA chain during ring closure"., Science, New Series, vol. 260, issue 5107, pp. 533-536, (1993).
Shekhtman, E.M., et al., "Stereostructure of replicative DNA catenanes from eukaryotic cells"., New Journal of Chemistry, vol. 17, pp. 757-763, (1993).
Sigurdsson, S.T., et al., "Small ribozymes"., RNA Structure and Function, Cold Spring Harbor Laboratory Press (Monograph 35), pp. 339-375, (1998).
Singh, K.K., et al., "Fluorescence Polarization for Monitoring Ribozyme Reactions in Real-Time"., Biotechniques, vol. 29, No. 2, pp. 344-351, (2000).
Smith, F.W., et al., "Quadruplex structure of oxytricha telomeric DNA oligonucleotides"., Nature, vol. 356, pp. 164-168, (1992).
Smith, J.O., et al., "Molecular recognition of PNA-containing hybrids: Spontaneous assembly of helical cyanine dye aggregates on PNA templates"., J. Am. Chem. Soc., vol. 121, No. 12, pp. 2686-2695, (1999).
Soriaga, M.P., et al., "Determination of the orientation of aromatic molecules adsorbed on platinum electrodes: The effect of solute concentration"., J. Am. Chem. Soc., vol. 104, No. 14, pp. 3937-3945, (1982).
Soukup, G.A., et al., "Engineering precision RNA molecular switches"., Proc. Natl. Acad. Sci. USA, vol. 96, pp. 3584-3589, (1999).
Soukup, G.A., et al., "Allosteric nucleic acid catalysts"., Current Opinion in Structural Biology, vol. 10, pp. 318-325, (2000).
Srisawat, C., et al., "Sephadex-binding RNA ligands: rapid affinity purification of RNA from complex RNA mixtures"., Nucleic Acids Research, vol. 29, No. 2 e4, pp. 1-5, (2001).
Stage-Zimmermann, T.K., et al., "Hammerhead ribozyme kinetics"., RNA, vol. 4, pp. 875-889, (1998).
Stojanovic, M.N., et al., "Aptamer-based colorimetric probe for cocaine"., J. Am. Chem. Soc., vol. 124, No. 33, pp. 9678-9679, (2002).
Stojanovic, M.N., et al., "Aptamer-based folding fluorescent sensor for cocaine"., Journal of the American Chemical Society, vol. 123, No. 21, pp. 4928-4931, (2001).
Stojanovic, M.N., et al., "Fluorescent sensors based on aptamer self-assembly"., Journal of the American Chemical Society, vol. 122, No. 46, pp. 11547-11548, (2000).

Storhoff, J.J., et al., "Programmed materials synthesis with DNA"., Chem. Rev., vol. 99, No. 7, pp. 1849-1862, (1999).
Storhoff, J.J., et al., "What Controls the Optical Properties of DNA-Linked Gold Nanoparticle Assemblies?"., J. Am. Chem. Soc., vol. 122, No. 19, pp. 4640-4650, (2000).
Storhoff, J.J., et al., "One-pot colorimetric differentiation of polynucleotides with single base imperfections using gold nanoparticle probes"., Journal of the American Chemical Society, vol. 120, No. 9, pp. 1959-1964, (1998).
Streicher, B., et al., "Lead cleavage site in the core structure of group I intron-RNA"., Nucleic Acids Research, vol. 21, No. 2, pp. 311-317, (1993).
Sugimoto, N., et al., "Site-specific cleavage reaction catalyzed by leadzyme is enhanced by combined effect of lead and rare earth ions"., FEBS Letters, vol. 393, pp. 97-100, (1996).
Sun, L.Q., et al., "Catalytic nucleic acids: From lab to applications"., Pharmacological Reviews, vol. 52, pp. 325-347, (2000).
Tahan, J.E., et al., "Electrothermal atomic absorption spectrometric determination of Al, Cu, Ge, Pb, V and Zn in clinical samples and in certified environmental reference materials"., Analytica Chimica Acta, vol. 295, pp, 187-197, (1994).
Takagi, Y., et al., "Survey and Summary: Recent advances in the elucidation of the mechanisms of action of ribozymes"., Nucleic Acids Research, vol. 29, No. 9, pp. 1815-1834, (2001).
Tang, J., et al., "Rational design of allosteric ribozymes"., Chemistry & Biology, vol. 4, No. 6, pp. 453-459, (1997).
Tang, J., et al., "Structural diversity of self-cleaving ribozymes"., Proc. Natl. Acad. Sci. USA, vol. 97, No. 11, pp. 5784-5789, (2000).
Tanner, N. K., "Biochemistry of hepatitis delta virus catalytic RNAs"., Ribozymes in the Gene Therapy of Cancer, Chapter 3, pp. 23-38, (1998).
Tao, J., et al., "Arginine-Binding RNAs Resembling TAR Identified by in Vitro Selection"., Biochemistry, vol. 35, No. 7, pp. 2229-2238, (1996).
Tarasow, T.M., et al., "RNA-catalysed carbon-carbon bond formation"., Nature, vol. 389, pp. 54-57, (1997).
Telting-Diaz, M., et al., "Mass-produced ionophore-based fluorescent microspheres for trace level determination of lead ions"., Analytical Chemistry, vol. 74, No. 20, pp. 5251-5256, (2002).
Thompson, R.B., et al., "Determination of Picomolar Concentrations of Metal Ions Using Fluorescence Anisotropy: Biosensing with a "Reagentless" Enzyme Transducer"., Analytical Chemistry, vol. 70, No. 22, pp. 4717-4723, (1998).
Timmons, C.O., et al., "Investigation of Fatty Acid Monolayers on Metals by Contact Potential Measurements", Journal of Physical Chemistry, vol. 69, No. 3, pp. 984-990, (1965).
Tompkins, H.G., et al., "The study of the gas-solid interaction of acetic acid with a cuprous oxide surface using reflection-absorption spectroscopy"., Journal of Colloid and Interface Science, vol. 49, No. 3, pp, 410-421, (1974).
Travascio, P., et al., "A ribozyme and a catalytic DNA with peroxidase activity: active sites versus cofactor-binding sites"., Chemistry & Biology, vol. 6, No. 11, pp. 779-787, (1999).
Tsang, J., et al., "In vitro evolution of randomized ribozymes"., Methods in Enzymology, vol. 267, pp. 410-426, (1996).
Tsien, R.Y., "Fluorescent and photochemical probes of dynamic biochemical signals inside living cells"., Fluorescent Chemosensors for Ion and Molecule Recognition, (ed. Czarnik, A. W.), chapter 9, pp. 130-146, American Chemical Society, (1993).
Tuerk, C., et al., "RNA pseudoknots that inhibit human immunodeficiency virus type 1 reverse transcriptase"., Proc. Natl. Acad. Sci. USA, vol. 89, pp. 6988-6992, (1992).
Tuerk, C., et al., "Systematic evolution of ligands by exponential enrichment: RNA ligands to bacteriophage T4 DNA polymerase"., Science, New Series, vol. 249, issue 4968, pp. 505-510, (1990).
Tyagi, S., et al., "Molecular Beacons: Probes that fluoresce upon hybridization"., Nature Biotechnology, vol. 14, pp. 303-308, (1996).
Tyagi, S., et al., "Multicolor molecular beacons for allele discrimination"., Nature Biotechnology, vol. 16, pp. 49-53, (1998).
Tyagi, S., et al., "Wavelength-shifting molecular beacons"., Nature Biotechnology, vol. 18, pp. 1191-1196, (2000).
Ueyama, H., "A novel potassium sensing in aqueous media with a synthetic oligonucleotide derivative. Fluorescence resonance energy transfer associated with guanine quartet-potassium ion complex formation"., J. Am. Chem. Soc., vol. 124, No. 48, pp. 14286-14287, (2002).

Uphoff, K.W., et al., "In vitro selection of aptamers: the dearth of pure reason"., Current Opinion in Structural Biology, vol. 6, pp. 281-288, (1996).

Vaish, N. K., et al., "In vitro selection of a purine nucleotide-specific hammerhead-like ribozyme"., Proc. Natl. Acad. Sci. USA, vol. 95, pp. 2158-2162, (1998).

Valadkhan, S., et al., "Splicing-related catalysis by protein-free snRNAs"., Nature, vol. 413, pp. 701-707, (2001).

Vianini, E., et al., "In vitro selection of DNA aptamers that bind L-tyrosinamide"., Bioorganic & Medicinal Chemistry, vol. 9, pp. 2543-2548, (2001).

Walkup, G.K., et al., "Design and Evaluation of a Peptidyl Fluorescent Chemosensor for Divalent Zinc"., J. Am. Chem. Soc., vol. 118, No. 12, pp. 3053-3054, (1996).

Wallace, S.T., et al., In vitro selection and characterization of streptomycin-binding RNAs: recognition discrimination between antibiotics. RNA, vol. 4, pp. 112-123, (1998).

Wallis, M.G., et al., "A novel RNA motif for neomycin recognition"., Chemistry & Biology, vol. 2, No. 8, pp. 543-552, (1995).

Wallis, M.G., et al., "In vitro selection of a viomycin-binding RNA pseudoknot"., Chemistry & Biology, vol. 4, No. 5, pp. 357-366, (1997).

Walter, F., et al., "Folding of the four-way RNA junction of the hairpin ribozyme"., Biochemistry, vol. 37, No. 50, pp. 17629-17636, (1998).

Walter, N.G., et al., "The hairpin ribozyme: structure, assembly and catalysis"., Current Opinion in Chemical Biology, vol. 2, pp. 24-30, (1998).

Wang, D.Y., et al., "A general strategy for effector-mediated control of RNA-cleaving ribozymes and DNA enzymes"., J. Mol. Biol., vol. 318, pp. 33-43, (2002).

Wang, F., et al., "Sphingosine-1-phosphate Inhibits Motility of Human Breast Cancer Cells Independently of Cell Surface Receptors"., Cancer Research, vol. 59, pp. 6185-6191, (1999).

Wang, J., "Survey and Summary: From DNA biosensors to gene chips"., Nucleic Acids Research, vol. 28, No. 16, pp. 3011-3016, (2000).

Wang, K.Y., et al., "A DNA aptamer which binds to and inhibits thrombin exhibits a new structural motif for DNA"., Biochemistry, vol. 32, No. 8, pp. 1899-1904, (1993).

Wang, Y., et al., "Assembly and characterization of five-arm and six-arm DNA branched junctions"., Biochemistry, vol. 30, pp. 5667-5674, (1991).

Wang, Y., et al., "RNA molecules that specifically and stoichiometrically bind aminoglycoside antibiotics with high affinities"., Biochemistry, vol. 35, No. 38, pp. 12338-12346, (1996).

Wecker, M., et al., "In vitro selection of a novel catalytic RNA: characterization of a sulfur alkylation reaction and interaction with a small peptide"., RNA, vol. 2, pp. 982-994, (1996).

Wedekind, J.E., et al., "Crystal structure of a lead-dependent ribozyme revealing metal binding sites relevant to catalysis"., Nature Structural Biology, vol. 6, No. 3, pp. 261-268, (1999).

Wedekind, J.E., et al., "Crystal structure of the leadzyme at 1.8 Å Resolution: Metal ion binding and the implications for catalytic mechanism and alto site ion regulation"., Biochemistry, vol. 42, No. 32, pp. 9554-9563, (2003).

Wells, R.D., "Unusual DNA structures"., Journal of Biological Chemistry, vol. 263, No. 3, pp. 1095-1098, (1988).

Werstuck, G., et al., "Controlling gene expression in living cells through small molecule-RNA interactions"., Science, vol. 282, pp. 296-298, (1998).

Whaley, S.R., et al., "Selection of peptides with semiconductor binding specificity for directed nanocrystal assembly"., Nature, vol. 405, pp. 665-668, (2000).

Whitesides, G.M., et al., "Self-assembled monolayers and lithography"., Proceedings of the Robert A. Welch Foundation 39th Conference on Chemical Research on Nanophase Chemistry, pp. 109-121, Houston, TX, Oct. 23-24, 1995.

Wiegand, T.W., et al., "High-affinity oligonucleotide ligands to human IgE inhibit binding to Fc epsilon receptor I"., The Journal of Immunology, vol. 157, pp. 221-230, (1996).

Wiegand, T.W., et al., "Selection of RNA amide synthases"., Chemistry & Biology, vol. 4, No. 9, pp. 675-683, (1997).

Williams, K.P., et al., "Bioactive and nuclease-resistant L-DNA ligand of vasopressin"., Proc. Natl. Acad. Sci. USA, vol. 94, pp. 11285-11290, (1997).

Williams, K.P., et al., "Selection of novel $Mg^{2+}$-dependent self-cleaving ribozymes" The EMBO Journal, vol. 14, No. 18, pp. 4551-4557, (1995).

Wilson, C., et al., "Functional requirements for specific ligand recognition by a biotin-binding RNA Pseudoknot"., Biochemistry, vol. 37, No. 41, pp. 14410-14419, (1998).

Wilson, C., et al., "In vitro evolution of a self-alkylating ribozyme"., Nature, vol. 374, pp. 777-782, (1995).

Wilson, C., et al., "Isolation of a fluorophore-specific DNA aptamer with weak redox activity"., Chemistry & Biology, vol. 5, No. 11, pp. 609-617, (1998).

Wilson, D.S., et al., "In vitro selection of functional nucleic acids"., Annu. Rev. Biochem. vol. 68, pp. 611-647, (1999).

Winkler, J.D., et al., "Photodynamic Fluorescent Metal Ion Sensors with Parts per Billion Sensitivity"., J. Am. Chem. Soc., vol. 120, No. 13, pp. 3237-3242, (1998).

Wittmann, C., et al.,"Microbial and Enzyme sensors for environmental monitoring"., Handbook of Biosensors and Electronic Noses: Medicine, Food, and the Environment, pp. 299-332, (1997).

Xia, P., et al., "Activation of Sphingosine Kinase by Tumor Necrosis Factor-α Inhibits Apoptosis in Human Endothelial Cells"., Journal of Biological Chemistry, vol. 274, No. 48, pp. 34499-34505, (1999).

Yan, H., et al., "DNA-Templated self-assembly of protein arrays and highly conductive nanowires"., Science, vol. 301, pp. 1882-1884, (2003).

Yang, Q., et al., "DNA ligands that bind tightly and selectively to cellobiose"., Proc. Natl. Acad. Sci. USA, vol. 95, pp. 5462-5467, (1998).

Yurke, B., et al., "A DNA-fuelled molecular machine made of DNA"., Nature, vol. 406, pp. 605-608, (2000).

Zhang, B., et al., "Peptide bond formation by in vitro selected ribozymes"., Nature, vol. 390, pp. 96-100, (1997).

Zhang, P., et al., "Design of a molecular beacon DNA probe with two fluorophores"., Angewandte Chemie International Edition, vol. 40, No. 2, pp. 402-405, (2001).

Zillmann, M., et al., "In vitro optimization of truncated stem-loop II variants of the hammerhead ribozyme for cleavage in low concentrations of magnesium under non-turnover conditions"., RNA, vol. 3, pp. 734-747, (1997).

Zimmerman, J.M., et al., "In vivo selection of spectinomycin-binding RNAs"., Nucleic Acids Research, vol. 30, No. 24, pp. 5425-5435, (2002).

Zimmermann, G.R., et al., "Molecular interactions and metal binding in the theophylline-binding core of an RNA aptamer"., RNA, vol. 6, pp. 659-667, (2000).

International Search Report dated Nov. 21, 2005 for corresponding PCT application No. PCT/US2005/001060.

Supplemental International Search Report dated Jan. 10, 2006 for corresponding PCT application No. PCT/US2005/001060.

Liu, J., et al., "Size control, metal substitution, and catalytic application of cryptomelane nanomaterials prepared using cross-linking reagents"., Chem. Mater., vol. 16, No. 2, pp. 276-285, (2004).

Abstract of: Iwasaki, K., Mizota, T., Kenkyu Hokoku—Kanagawa-ken Kogyo Shikensho 1991, 62, 57.

Storhoff, J.J., et al., "Facile colorimetric detection of polynucleotides based on gold nanoparticle probes"., Proceedings of the 1998 ERDEC Scientific Conference on Chemical and Biological Defense Research, Nov. 17-20, 1998, Aberdeen Proving Ground, pp. 221-226, (1999).

Yang, Y., et al., "Measurement of lead and magnesium in distilled spirits using inductively coupled plasma optical emission spectrometry viewed from the end"., Analytical Chemistry (Fenxi Huaxue), Chinese Journal of Analytical Chemistry, vol. 25, No. 9, pp. 1114-1117, (1997).

Cake, K.M., et al., "Partition of circulating lead between serum and red cells is different for internal and external sources of lead"., American Journal of Industrial Medicine, vol. 29, pp. 440-445, (1996).
International Search Report dated Aug. 31, 2004 for corresponding PCT application No. PCT/US2004/002946.
Hazarika, P., et al., "Reversible switching of DNA-Gold nanoparticle aggregation"., Angewandte Chemie International Edition, vol. 43, No. 47, pp. 6469-6471, (2004).
International Search Report dated May 29, 2006 for PCT application No. PCT/US2005/037896 (related application).
Liu, J., et al., "Improving fluorescent DNAzyme biosensors by combining Inter- and Intramolecular quenchers"., Analytical Chemistry, vol. 75, No. 23, pp. 6666-6672, (2003).
Liu, J., et al., "Stimuli-responsive disassembly of nanoparticle aggregates for light-up colorimetric sensing"., Journal of the American Chemical Society, vol. 127, No. 36, pp. 12677-12683, (2005).
European Search Report dated Jul. 10, 2006 for PCT application No. PCT/US2003/12576.
Tanner, F.C., et al., "Transfection of human endothelial cells"., Cardiovascular Research, vol. 35, pp. 522-528, (1997).
International Search Report dated Nov. 17, 2006 for PCT application No. PCT/US2006/001627.
Liu, J., et al., "DNAzyme-directed assembly of gold nanoparticles as colorimetric sensor for a broad range of analytes", pp. 1-3, located at http://ieeenano2003.arc.nasa.gov/THM@.pdf, (2003).
Wang, D.Y., et al., "A general approach for the use of oligonucleotide effectors to regulate the catalysis of RNA-cleaving ribozymes and DNAzymes", Nucleic Acids Research, vol. 30, No. 8, pp. 1735-1742, (2002).
Levy, M., et al., "Exponential growth by cross-catalytic cleavage of deoxyribozymogens",PNAS, vol. 100, No. 11, pp. 6416-6421, (2003).
Beyer, S., et al., "A modular DNA signal translator for the controlled release of a protein by an aptamer", Nucleic Acids Research, vol. 34, No. 5, pp. 1581-1587, (2006).
Frauendorf, C., et al., "Detection of small organic analytes by fluorescing molecular switches", Bioorganic & Medicinal Chemistry, vol. 9, pp. 2521-2524, (2001).
Glynou, K., et al., "Oligonucleotide-functionalized gold nanoparticles as probes in a dry-reagent strip biosensor for DNA analysis by hybridization", Anal. Chem, vol. 75, No. 16, pp. 4155-4160, (2003).
Liu, J., et al., "Optimization of a $Pb^{2+}$-directed gold nanoparticle/DNAzyme assembly and its application as a colorimetric biosensor for $Pb^{2+}$", Chem. Mater., vol. 16, No. 17, pp. 3231-3238, (2004).
Jones, K.D., et al., "Anniversary Essays, 3. Assay development, Changes in the development of rapid assays since 1995", Medical Devicelink, found at: http://www.devicelink.com/ivdt/archive/05/04/005.html, 3 pages, (2005).
Product Description: Pall Corporation, "Immunochromatographic, lateral flow or strip tests development ideas", found at: http://www.pall.com/34445_4154.asp, 7 pages, (1998).
Liu, J., et al., "Fast colorimetric sensing of adenosine and cocaine based on a general sensor design involving aptamers and nanoparticles", Angew. Chem. Int. Ed., vol. 45, pp. 90-94, (2006).
Liu, J., et al., "A simple and sensitive "dipstick" test in serum based on lateral flow separation of aptamer-linked nanostructures", Angewandte Chemie International Edition, vol. 45, pp. 7955-7959, (2006).
Jiang, P. et al., "Fluorescent detection of zinc in biological systems: recent development on the design of chemosensors and biosensors", Coordination Chemistry Reviews, vol. 248, pp. 205-229, (2004).
Lim, M.H. et al., "Metal-based turn-on fluorescent probes for sensing nitric oxide", Accounts of Chemical Research, vol. 40, No. 1, pp. 41-51, (2007).
Yoon, S. et al., "Screening mercury levels in fish with a selective fluorescent chemosensor", Journal of the American Chemical Society, vol. 127, pp. 16030-16031, (2005).
Yang, L. et al., "Imaging of the intracellular topography of copper with a fluorescent sensor and by synchrotron x-ray fluorescence microscopy", Proceedings of the National Academy of Science, vol. 102, No. 32, pp. 11179-11184, (2005).

He, Q. et al., "A selective fluorescent sensor for detecting lead in living cells", Journal of the American Chemical Society, vol. 128, pp. 9316-9317, (2006).
Zeng, L. et al., "A selective turn-on fluorescent sensor for imaging copper in living cells", Journal of the American Chemical Society, vol. 128, pp. 10-11, (2006).
Wegner, S.V. et al., "Design of an emission ratiometric biosensor from MerR family proteins: A sensitive and selective sensor for $Hg^{2+}$", Journal of the American Chemical Society, vol. 129, pp. 3474-3475, (2007).
Nolan, E.M. et al., "Turn-on and ratiometric mercury sensing in water with a red-emitting probe", Journal of the American Chemical Society, vol. 129, pp. 5910-5918, (2007).
Sasaki, D.Y. et al., "Metal-induced dispersion of lipid aggregates: A simple, selective, and sensitive fluorescent metal ion sensor", Angew. Chem. Int. Ed. England, vol. 34, No. 8, pp. 905-907, (1995).
Torrado, A. et al., "Exploiting polypeptide motifs for the design of selective Cu(II) ion chemosensors" Journal of the American Chemical Society, vol. 120, pp. 609-610, (1998).
Grandini, P. et al., "Exploiting the self-assembly strategy for the design of selective $Cu^{II}$ ion chemosensors", Angew. Chem. Int. Ed, vol. 38, No. 20, pp. 3061-3064, (1999).
Klein, G. et al., "A fluorescent metal sensor based on macrocyclic chelation", Chem. Comm., pp. 561-562, (2001).
Zheng, Y. et al., "A new fluorescent chemosensor for copper ions based on tripeptide glycyl-histidyl-lysine (GHK)", Organic Letters, vol. 3, No. 21, pp. 3277-3280, (2001).
Boiocchi, M. et al., "A two-channel molecular dosimeter for the optical detection of copper(II)" Chem. Comm, pp. 1812-1813, (2003).
Zheng, Y. et al., "Peptidyl fluorescent chemosensors for the detection of divalent copper", Analytical Chemistry, vol. 75, No. 7, pp. 1706-1712, (2003).
Zheng, Y. et al., "Development of fluorescent film sensors for the detection of divalent copper", Journal of the American Chemical Society, vol. 125, pp. 2680-2686, (2003).
Roy, B.C. et al., "Synthesis of new, pyrene-containing metal-chelating lipids and sensing of cupric ions", Organic Letters, vol. 5, No. 1, pp. 11-14, (2003).
Kaur, S. et al., "Photoactive chemosensors 4: a $Cu^{2+}$ protein cavity mimicking fluorescent chemosensor for selective $Cu^{2+}$ recognition", Tetrahedron Letters, vol. 45, pp. 5081-5085, (2004).
Mei, Y. et al., "A selective and sensitive chemosensor for $Cu^{2+}$ based on 8-hydroxyquinoline", Tetrahedron Letters, vol. 47, pp. 2447-2449, (2006).
Zhang, X-B. et al., "A highly selective fluorescent sensor for $Cu^{2+}$ based on 2-(2'-hydroxyphenyl) benzoxazole in a poly(vinyl chloride) matrix", Analytica Chimica Acta, vol. 567, pp. 189-195, (2006).
Comba, P. et al., "Synthesis of new phenanthroline-based heteroditopic ligands—highly efficient and selective fluorescence sensors for copper (II) ions", European Journal of Inorganic Chemistry, pp. 4442-4448, (2006).
Kim, S. H. et al., "$Hg^{2+}$-selective off-on and $Cu^{2+}$-selective on-off type fluoroionophore based upon cyclam", Organic Letters, vol. 8, No. 3, pp. 371-374, (2006).
White, B. R. et al., "Fluorescent peptide sensor for the selective detection of $Cu^{2+}$", Talanta, vol. 71, pp. 2015-2020, (2007).
Oter, O. et al., "Spectral characterization of a newly synthesized fluorescent semicarbazone derivative and its usage as a selective fiber optic sensor for copper(II)", Analytica Chimica Acta, vol. 584, pp. 308-314, (2007).
Dujols, V. et al., "A long-wavelength fluorescent chemodosimeter selective for Cu(II) ion in water", Journal of the American Chemical Society, vol. 119, pp. 7386-7387, (1997).
Yang, J-S. et al., "$Cu^{2+}$-induced blue shift of the pyrene excimer emission: a new signal transduction mode of pyrene probes", Organic Letters, vol. 3, No. 6, pp. 889-892, (2001).
Kaur, S. et al., "Photoactive chemosensors 3: a unique case of fluorescence enhancement with Cu(II)", Chem. Comm., pp. 2840-2841, (2002).
Wu, Q. et al., "Catalytic signal amplification using a heck reaction. An example in the fluorescence sensing of Cu(II)", Journal of the American Chemical Society, vol. 126, pp. 14682-14683, (2004).

Royzen, M. et al., "Ratiometric displacement approach to Cu(II) sensing by fluorescence", Journal of the American Chemical Society, vol. 127, pp. 1612-1613, (2005).

Xu, Z. et al., "Ratiometric and selective fluorescent sensor for $Cu^{II}$ based on internal charge transfer (ICT)", Organic Letters, vol. 7, No. 5, pp. 889-892, (2005).

Wen, Z-C. et al., "A highly selective charge transfer fluoroionophore for $Cu^{2+}$", Chem. Commun., pp. 106-108, (2006).

Yang, H. et al., "Highly selective ratiometric fluorescent sensor for Cu(II) with two urea groups", Tetrahedron Letters, vol. 47, pp. 2911-2914, (2006).

Martinez, R. et al., "2-aza-1,3-butadiene derivatives featuring an anthracene or pyrene unit: highly selective colorimetric and fluorescent signaling of $Cu^{2+}$ cation", Organic Letters, vol. 8, No. 15, pp. 3235-3238, (2006).

Navani, N.K. et al., "Nucleic acid aptamers and enzymes as sensors", Current Opinion in Chemical Biology, vol. 10, pp. 272-281, (2006).

Liu, J. et al., "A catalytic beacon sensor for uranium with parts-per-trillion sensitivity and millionfold selectivity", Proceedings of the National Academy of Science, vol. 104, No. 7, pp. 2056-2061, (2007).

Georgopoulos, P.G. et al., "Environmental copper: its dynamics and human exposure issues", Journal of Toxicology and Environmental Health, Part B, vol. 4, pp. 341-394, (2001).

Hertzberg, R.P. et al., "Cleavage of DNA with methidiumpropyl-EDTA-iron(II): reaction conditions and product analyses", Biochemistry, vol. 23, pp. 3934-3945, (1984).

Yazzie, M. et al., "Uranyl acetate causes DNA single strand breaks in vitro in the presence of ascorbate (Vitamin C)", Chem. Res. Toxicol., vol. 16, pp. 524-530, (2003).

Bolletta, F. et al., "A [$Ru^{II}$ (bipy)$_3$]-[1,9-diamino-3,7-diazanonane-4,6-dione] two-component system as an efficient on-off luminescent chemosensor for $Ni^{2+}$ and $Cu^{2+}$ in water, based on an ET (energy transfer) mechanism", Journal of the Chemical Society, Dalton Transactions, pp. 1381-1385, (1999).

Carmi, N. et al., "Characterization of a DNA-cleaving deoxyribozyme", Bioorganic & Medicinal Chemistry, vol. 9, issue 10, pp. 2589-2600, (2001).

Liu, J. et al., "A DNAzyme catalytic beacon sensor for paramagnetic $Cu^{2+}$ ions in aqueous solution with high sensitivity and selectivity", Journal of the American Chemical Society, 2 pages, (2007), ASAP Web Release Date: Jul. 24, 2007.

Tanaka, K. et al., "Programmable self-assembly of metal ions inside artificial DNA duplexes", Nature Nanotechnology, vol. 1, pp. 190-194, (2006).

Achenbach, J.C. et al., "DNAzymes: From creation in vitro to application in vivo", Current Pharmaceutical Biotechnology, vol. 5, pp. 321-336, (2004).

Balaji, T. et al., "Optical sensor for the visual detection of mercury using mesoporous silica anchoring porphyrin moiety", The Analyst, vol. 130, pp. 1162-1167, (2005).

Caballero, A. et al., "Highly selective chromogenic and redox or fluorescent sensors of $Hg^{2+}$ in aqueous environment based on 1,4-disubstituted azines", Journal of the American Chemical Society, vol. 127, pp. 15666-15667, (2005).

Chan, W.H. et al., "Development of a mercury ion-selective optical sensor based on fluorescence quenching of 5,10,15,20-tetraphenylporphyrin", Analytica Chimica Acta, vol. 444, pp. 261-269, (2001).

Chen, P. et al., "A general strategy to convert the merR family proteins into highly sensitive and selective fluorescent biosensors for metal ions", Journal of the American Chemical Society, vol. 126, pp. 728-729, (2004).

Chiuman, W. et al., "Efficient signaling platforms built from a small catalytic DNA and doubly labeled fluorogenic substrates", Nucleic Acids Research, vol. 35, No. 2, pp. 401-405, (2007).

Cruz, R.P.G. et al., "Dinucleotide junction cleavage versatility of 8-17 deoxyribozyme", Chemistry & Biology, vol. 11, pp. 57-67, (2004).

Frasco, M.F. et al., "Mechanisms of cholinesterase inhibition by inorganic mercury", the FEBS Journal, vol. 274, pp. 1849-1861, (2007).

Guo, X. et al., "A highly selective and sensitive fluorescent chemosensor for $Hg^{2+}$ in neutral buffer aqueous solution", The Jouranl of the American Chemical Society, vol. 126, pp. 2272-2273, (2004).

Harris, H.H. et al., "The chemical form of mercury in fish", Science, vol. 301, pp. 1203, (2003).

Ha-Thi, M-H. et al., "Highly selective and sensitive phosphane sulfide derivative for the detection of $Hg^{2+}$ in an organoaqueous medium", Organic Letters, vol. 9, No. 6, pp. 1133-1136, (2007).

Joyce, G.F. et al., "Directed evolution of nucleic acid enzymes", Annual Review Biochem., vol. 73, pp. 791-836, (2004).

Ko, S-K. et al., "In vivo monitoring of mercury ions using a rhodamine-based molecular probe", Journal of the American Chemical Society, vol. 128, pp. 14150-14155, (2006).

Kuswandi, B. et al., "Capillary optode: determination of mercury(II) in aqueous solution", Analytical Letters, vol. 32, No. 9. 4, pp. 649-664, (1999).

Kuswandi, B. et al., "Selective pool optode for mercury ion sensing in aqueous solution", Sensors and Actuators B, vol. 74, pp. 131-137, (2001).

Lee, J-S. et al., "Colorimetric detection of mercuric ion ($Hg^{2+}$) in aqueous media using DNA-functionalized gold nanoparticles", Angewandte Chemie International Edition, vol. 46, pp. 4093-4096, (2007).

Liu, B. et al., "A selective fluorescent ratiometric chemodosimeter for mercury ion", Chem. Communications, pp. 3156-3158, (2005).

Liu, J. et al., "Fluorescent DNAzyme biosensors for metal ions based on catalytic molecular beacons", Methods in Molecular Biology, vol. 335, pp. 275-288, (2006).

Matsushita, M. et al., "A blue fluorescent antibody-cofactor sensor for mercury", Organic Letters, vol. 7, No. 22, pp. 4943-4946, (2005).

Miyake, Y. et al., "$Mercury^{II}$-mediated formation of thymine-$Hg^{II}$-thymine base pairs in DNA duplexes", Journal of the American Chemical Society, vol. 128, No. 7, pp. 2172-2173, (2006).

Nolan, E.M. et al., "A "turn-on" fluorescent sensor for the selective detection of mercuric ion in aqueous media", Journal of the American Chemical Society, vol. 125, pp. 14270-14271, (2003).

Ono, A. et al., "highly selective oligonucleotide-based sensor for mercury (II) in aqueous solutions", Angew. Chem. Int. Ed., vol. 43, pp. 4300-4302, (2004).

Ostatna, V. et al., "Self-assembled monolayers of thiol-end-labeled DNA at mercury electrodes", Langmuir, vol. 22, pp. 6481-6484, (2006).

Prodi, L. et al., "An effective fluorescent achemosensor for mercury ions", Journal of the American Chemical Society, vol. 122, No. 28, pp. 6769-6770, (2000).

Silverman, S.K., "Survey and Summary: In vitro selection, characterization, and application of deoxyribozymes that cleave RNA", Nucleic Acids Research, vol. 33, No. 19, pp. 6151-6163, (2005).

Song, K.C. et al., "Fluorogenic $Hg^{2+}$-selective chemodosimeter derived from 8-hydroxyquinoline", Organic Letters, vol. 8, No. 16, pp. 3413-3416, (2006).

Szurdoki, F. et al., "A combinatorial approach to discover new chelators for optical metal ion sensing", Analytical Chemistry, vol. 72, No. 21, pp. 5250-5257, (2000).

Tanaka, Y. et al., "$^{15}$N-$^{15}$N J-coupling across $Hg^{II}$: Direct observation of $Hg^{II}$-mediated T-T base pairs in a DNA duplex" Journal of the American Chemical Society, vol. 129, No. 2, pp. 244-245, (2007).

Jacoby, M. "Mercury Sensor—Analytical Chemistry: Colorimetric method is sensitive and selective", Chemical & Engineering News, pp. 15, May 7, 2007.

Vannela, R. et al., "In vitro selection of Hg (II) and as (V)-dependent RNA-cleaving DNAzymes", Environmental Engineering Science, vol. 24, No. 1, pp. 73-84, (2007).

Vaughan, A.A. et al., "Optical fibre reflectance sensors for the detection of heavy metal ions based on immobilized Br-PADAP", Snesors and Actuators B, vol. 51, pp. 368-376, (1998).

Virta, M. et al., "A luminescence-based mercury biosensor", Analytical Chemistry, vol. 67, No. 3, pp. 667-669, (1995).

Wang, J. et al., "Detecting $Hg^{2+}$ ions with an ICT fluorescent sensor molecule: Remarkable emission spectra shift and unique selectivity", Journal of Organic Chemistry, vol. 71, pp. 4308-4311, (2006).

Wang, J. et al., "A series of polyamide receptor based PET fluorescent sensor molecules: Positively cooperative $Hg^{2+}$ ion binding with high sensitivity", Organic Letters, vol. 8, No. 17, pp. 3721-3724, (2006).

Widmann, A. et al., "Mercury detection in seawater using a mercaptoacetic acid modified gold microwire electrode", Electroanalysis, vol. 17, No. 10, pp. 825-831, (2005).

Xiao, Y. et al., "Electrochemical detection of parts-per-billion lead via an electrode-bound DNAzyme assembly", Journal of the American Chemical Society, vol. 129, pp. 262-263, (2007).

Yang, W. et al., "Solid phase extraction and spectrophotometric determination of mercury in tobacco and tobacco additives with 5-(p-aminobenzylidene)-thiothiorhodanine", Journal of the Brazilian Chemical Society, vol. 17, No. 5, pp. 1039-1044, (2006).

Yang, Y-K. et al., "A rhodamine-based fluorescent and colorimetric chemodosimeter for the rapid detection of Hg2+ ions in aqueous media", Journal of the American Chemical Society, vol. 127, pp. 16760-16761, (2005).

Zhang, X-B. et al "An optical fiber chemical sensor for mercury ions based on a porphyrin dimmer", Analytical Chemistry, vol. 74, No. 4, pp. 821-825, (2002).

Zhao, Y. et al., "A "turn-on" fluorescent sensor for selective Hg(II) detection in aqueous media based on metal-induced dye formation", Inorganic Chemistry, vol. 45, No. 25, pp. 10013-10015, (2006).

Zhao, Y. et al., "Tuning the sensitivity of a foldamer-based mercury sensor by its folding energy", Journal of the American Chemical Society, vol. 128, No. 31, pp. 9988-9989, (2006).

Zhao, Y. et al., "Detection of Hg2+ in aqueous solutions with a foldamer-based fluorescent sensor modulated by surgactant micelles", Organic Letters, vol. 8, No. 21, pp. 4715-4717, (2006).

Zuker, M., "Mfold web server for nucleic acid folding and hybridization prediction", Nucleic Acids Research, vol. 31, No. 13, pp. 3406-3415, (2003).

International Search Report dated May 10, 2007 for PCT application No. PCT/US2006/030617.

Liu, J. et al., "Adenosine-dependent assembly of aptazyme-functionalized gold nanoparticles and its application as a colorimetric biosensor", Analytical Chemistry, vol. 76, No. 6, pp. 1627-1632, (2004).

Liu, J. et al., "Smart nanomaterials responsive to multiple chemical stimuli with controllable cooperativity", Advanced Materials, vol. 18, No. 13, pp. 1667-1671, (2006).

Nutiu, R. et al., "Signaling aptamers for monitoring enzymatic activity and for inhibitor screening", Chembiochem—A European Journal of Chemical Biology, vol. 5, No. 8, pp. 1139-1144, (2004).

Nutiu, R. et al., "Structure-switching signaling aptamers: Transducing molecular recognition into fluorescence signaling", Chemistry—A European Journal, vol. 10, No. 8, pp. 1868-1876, (2004).

International Search Report dated Jul. 31, 2007 for PCT application No. PCT/US2007/064055.

Ahern, H., "Biochemical, reagent kits offer scientists good return on investment", The Scientist, vol. 9, No. 15, pp. 20-22, (1995).

Homann, M. et al., "Dissociation of long-chain duplex RNA can occur via strand displacement in vitro: biological implication", Nucleic Acids Research, vol. 24, No. 22, pp. 4395-4400, (1996).

Alivisatos, A.P. et al., "Quantum dots as cellular probes", Annual Review Biomed. Eng, vol. 7, pp. 55-76, (2005).

Dyadyusha, L. et al., "Quenching of CdSe quantum dot emission, a new approach for biosensing", Chemical Communication, pp. 3201-3203, (2005).

Ellington, A.D. et al., "In vitro selection of RNA molecules that bind specific ligands", Nature, vol. 346, pp. 818-822, (1990).

Gerion, D. et al., "Room-temperature single-nucleotide polymorphism and multiallele DNA detection using fluorescent nanocrystals and microarrays", Analytical Chemistry, vol. 75, No. 18, pp. 4766-4772, (2003).

Goldman, E.R. et al., "Multiplexed toxin analysis using four colors of quantum dot fluororeagents", Analytical Chemistry, vol. 76, No. 3, pp. 684-688, (2004).

Gueroui, Z. et al., "Single-molecule measurements of gold-quenched quantum dots", Physical Review Letters, vol. 93, No. 16, pp. 166108/1-166108/4, (2004).

Han, M. et al., "Quantum-dot-tagged microbeads for multiplexed optical coding of biomolecules", Nature Biotechnology, vol. 19, pp. 631-635, (2001).

Hansen, J.A. et al., "Quantum-dot/Aptamer-based ultrasensitive multi-analyte electrochemical biosensor", Journal of the American Chemical Society, vol. 128, No. 7, pp. 2228-2229, (2006).

Hartig, J.S. et al., "Protein-dependent ribozymes report molecular interactions in real time", Nature Biotechnology, vol. 20, pp. 717-722, (2002).

Herman, T. et al., "Adaptive recognition by nucleic acid aptamers", Science, vol. 287, pp. 820-825, (2000).

Kurreck, J., "Antisense technologies Improvement through novel chemical modifications", Eur. J. Biochem, vol. 270, pp. 1628-1644, (2003).

Lee, J.F. et al., "Aptamer database", Nucleic Acids Research, vol. 32, Database Issue, pp. D95-D100, (2004).

Levy, M. et al., "Quantum-dot aptamer beacons for the detection of proteins", ChemBioChem, vol. 6, pp. 2163-2166, (2005).

Liu, J. et al., "Smart nanomaterials responsive to multiple chemical stimuli with controllable cooperativity", Advanced Materials, vol. 18, pp. 1667-1671, (2006).

Liu, J. et al., "Preparation of aptamer-linked gold nanoparticle purple aggregates for colorimetric sensing of analytes", Nature Protocols, vol. 1, No. 1, pp. 246-252, (2006).

Medintz, I.L. et al., "Quantum dot bioconjugates for imaging, labeling and sensing", Nature Materials, vol. 4, pp. 435-446, (2005).

Miduturu, C. V. et al., "Modulation of DNA constraints that control macromolecular folding", Angew. Chem. Int. Ed., vol. 45, pp. 1918-1921, (2006).

Mitchell, G.P. et al., "Programmed assembly of DNA functionalized quantum dots", Journal of the American Chemical Society, vol. 121, No. 35, pp. 8122-8123, (1999).

Nutiu, R. et al., "Structure-switching signaling aptamers: Transducing molecular recognition into fluorescence signaling", Chem. Eur. J., vol. 10, pp. 1868-1876, (2004).

Oh, E. et al., "Inhibition assay of biomolecules based on fluorescence resonance energy transfer (FRET) between quantum dots and gold nanoparticles", Journal of the American Chemical Society, vol. 127, No. 10, pp. 3270-3271, (2005).

Rajendran, M. et al., "In vitro selection of molecular beacons", Nucleic Acids Research, vol. 31, No. 19, pp. 5700-5713, (2003).

Vet, J.A.M. et al., "Multiplex detection of four pathogenic retroviruses using molecular beacons", Proceedings of the National Academy of Science, USA., vol. 96, pp. 6394-6399, (1999).

Wargnier, R. et al., "Energy transfer in aqueous solutions of oppositely charged CdSe/ZnS core/shell quantum dot-nanogold assemblies", Nano Letters, vol. 4, No. 3, pp. 451-457, (2004).

Wilson, R. et al., "Encoded microcarriers for high-throughput multiplexed detection", Angewandte Chemie International Edition, vol. 45, pp. 6104-6117, (2006).

Winkler, W.C. et al., "Regulation of bacterial gene expression by riboswitches", The Annual Review of Microbiology, vol. 59, pp. 487-517, (2005).

Yang, C.J. et al., "Light-switching excimer probes for rapid protein monitoring in complex biological fluids", PNAS, vol. 102, No. 48, pp. 17278-17283, (2005).

Liu, J. et al., "Quantum dot encoding of aptamer-linked nanostructures for one-pot simultaneous detection of multiple analytes", Analytical Chemistry, vol. 79, No. 11, pp. 4120-4125, (2007).

Lu, Y. et al., "Smart nanomaterials inspired by biology: Dynamic assembly of error-free nanomaterials in response to multiple chemical and biological stimuli", Accounts of Chemical Research, vol. 40, No. 5, pp. 315-323, (2007).

Allen, M.J. et al., "Magnetic resonance contrast agents for medical and molecular imaging", Met. Ions Biol. Syst., vol. 42, pp. 1-38, (2004).

Artemov, D. et al., "MR molecular imaging of the Her-2/neu receptor in breast cancer cells using targeted iron oxide nanoparticles", Magnetic Resonance in Medicine, vol. 49, pp. 403-408, (2003).

Buerger, C. et al., "Sequence-specific peptide aptamers, interacting with the intracellular domain of the epidermal growth factor receptor, interfere with stat3 activation and inhibit the growth of tumor cells", The Journal of Biological Chemistry, vol. 278, No. 39, pp. 37610-37621, (2003).

Buerger, C. et al., "Bifunctional recombinant proteins in cancer therapy: cell penetrating peptide aptamers as inhibitors of growth factor signaling", J. Cancer Research Clin. Oncol., vol. 129, pp. 669-675, (2003).

Carr, D.H. et al., "Gadolinium-DTPA as a contrast agent in MRI: initial clinical experience in 20 patients", American Journal of Roentfenol., vol. 143, pp. 215-224, (1984).

Chen, Y. et al., "An autonomous DNA nanomotor powered by a DNA enzyme", Angew. Chem. Int. Ed., vol. 43, pp. 3554-3557, (2004).

Corot, C. et al., "Macrophage imaging in central nervous system and in carotid atherosclerotic plaque using ultrasmall superparamagnetic iron oxide in magnetic resonance imaging", Investigative Radiology, vol. 39, No. 10, pp. 619-625, (2004).

Dodd, C.H. et al., "Normal T-cell response and in vivo magnetic resonance imaging of T cells loaded with HIV transactivator-peptide-derived superparamagnetic nanoparticles", Journal of Immunological Methods, vol. 256, pp. 89-105, (2001).

Drolet, D.W. et al., "An enzyme-linked oligonucleotide assay", Nature Biotechnology, vol. 14, pp. 1021-1025, (1996).

Enochs, W.S. et al., "Improved delineation of human brain tumors on MR images using a long-circulating, superparamagnetic iron oxide agent", Journal of Magnetic Resonance Imaging, vol. 9, pp. 228-232, (1999).

Famulok, M. et al., "Nucleic acid aptamers-from selection in vitro to applications in vivo", Accounts of Chemical research, vol. 33, No. 9, pp. 591-599, (2000).

Fang, X. et al., "Molecular aptamer for real-time oncoprotein platelet-derived growth factor monitoring by fluorescence anisotropy", Analytical Chemistry, vol. 73, No. 23, pp. 5752-5757, (2001).

Frullano, L. et al., "Synthesis and characterization of a doxorubicin-Gd(III) contrast agent conjugate: A new approach toward prodrug-procontrast complexes", Inorganic Chemistry, vol. 45, No. 21, pp. 8489-8491, (2006).

Hamaguchi, N. et al., "Aptamer beacons for the direct detection of proteins", Analytical Biochemistry, vol. 294, pp. 126-131, (2001).

Harisinghani, M.G. et al., "Noninvasive detection of clinically occult lymph-node metastases in prostate cancer", The New England Journal of Medicine, vol. 348, No. 25, pp. 2491-2499, (2003).

Hermann, T. et al., "Adaptive recognition by nucleic acid aptamers", Science, vol. 287, pp. 820-825, (2000).

Hoppe-Seyler, F. et al., "Peptide aptamers: Specific inhibitors of protein function", Current Molecular Medicine, vol. 4, pp. 529-538, (2004).

Huang, C-C. et al., "Aptamer-modified gold nanoparticles for colorimetric determination of platelet-derived growth factors and their receptors", Analytical Chemistry, vol. 77, No. 17, pp. 5735-5741, (2005).

Josephson, L. et al., "High-efficiency intracellular magnetic labeling with novel superparamagnetic-tat peptide conjugates", Bioconjugate Chem., vol. 10, No. 2, pp. 186-191, (1999).

Josephson, L. et al., "The effects of iron oxides on proton relaxivity", Magnetic Resonance Imaging, vol. 6, pp. 647-653, (1988).

Josephson, L. et al., "Magnetic nanosensors for the detection of oligonucleotide sequences", Angew. Chem. Int. Ed., vol. 40, No. 17, pp. 3204-3206, (2001).

Kabalka, G. et al., "Gadolinium-labeled liposomes: Targeted MR contrast agents for the liver and spleen", Radiology, vol. 163, pp. 255-258, (1987).

Kooi, M.E. et al., "Accumulation of ultrasmall superparamagnetic particles of iron oxide in human atherosclerotic plaques can be detected by in vivo magnetic resonance imaging", Circulation, vol. 107, pp. 2453-2458, (2003).

Kresse, M. et al., "Targeting of ultrasmall superparamagnetic iron oxide (USPIO) particles to tumor cells in vivo by using transferring receptor pathways", Magn. Reson. Med., vol. 40, pp. 236-242, (1998).

Lee, J. et al., "A steroid-conjugated contrast agent for magnetic resonance imaging of cell signaling", Journal of American Chemical Society, vol. 127, No. 38, pp. 13164-13166, (2005).

Lewin, M. et al., "Tat peptide-derivatized magnetic nanoparticles allow in vivo tracking and recovery of progenitor cells", Nature Biotechnology, vol. 18, pp. 410-414, (2000).

Li, J.J. et al., "Molecular aptamer beacons for real-time protein recognition", Biochemical and Biophysical Research Communications, vol. 292, No. 1, pp. 31-40, (2002).

Li, W-H. et al., "A calcium-sensitive magnetic resonance imaging contrast agent", Journal of the American Chemical Society, vol. 121, No. 6, pp. 1413-1414, (1999).

Lin, C.H. et al., "Structural basis of DNA folding and recognition in an AMP-DNA aptamer complex: distinct architectures but common recognition motifs for DNA and RNA aptamers complexed to AMP", Chemistry and Biology, vol. 4, pp. 817-832, (1997).

Liss, M. et al., "An aptamer-based quartz crystal protein biosensor", Analytical Chemistry, vol. 74, No. 17, pp. 4488-4495, (2002).

Liu, Y. et al., "Aptamer-directed self-assembly of protein arrays on a DNA nanostructure", Angew. Chem. Int. Ed., vol. 44, pp. 4333-4338, (2005).

Macaya, R.F. et al., "Thrombin-binding DNA aptamer forms a unimolecular quadruplex structure in solution", Proceedings of the National Academy of Science USA, vol. 90, pp. 3745-3749, (1993).

Nagel-Wolfrum, K. et al., "The interaction of specific peptide aptamers with the DNA binding domain and the dimerization domain of the transcription factor stat3 inhibits transactivation and induces apoptosis in tumor cells", Molecular Cancer Research, vol. 2, pp. 170-182, (2004).

Nitin, N. et al., "Functionalization and pepride-based delivery of magnetic nanoparticles as an intracellular MRI contrast agent", J. Biol. Inorg. Chem., vol. 9, pp. 706-712, (2004).

Nutiu, R. et al., "Engineering DNA aptamers and DNA enzymes with fluorescence-signaling properties", Pure Appl. Chem., vol. 76, Nos. 7-8, pp. 1547-1561, (2004).

Padmanabhan, K. et al., "The structure of a-thrombin inhibited by a 15-mer single-stranded DNA aptamer", The Journal of Biological Chemistry, vol. 268, No. 24, pp. 17651-17654, (1993).

Pavlov, V. et al., "Aptamer-functionalized au nanoparticles for the amplified optical detection of thrombin", The Journal of the American Chemical Society, vol. 126, No. 38, pp. 11768-11769, (2004).

Pendergrast, P.S. et al., "Nucleic acid aptamers for target validation and therapeutic applications", Journal of Biomolecular Techniques, vol. 16, issue 3, pp. 224-234, (2005).

Perez, J.M. et al., "Use of magnetic nanoparticles as nanosensors to probe for molecular interactions", ChemBioChem, vol. 5, pp. 261-264, (2004).

Perez, J.M. et al., "Viral-induced self-assembly of magnetic nanoparticles allows the detection of viral particles in biological media", Journal of the American Chemical Society, vol. 125, No. 34, pp. 10192-10193, (2003).

Radi, A-E. et al., "Reagentless, reusable, ultrasensitive electrochemical molecular beacon aptasensor", Journal of the American Chemical Society, vol. 128, No. 1, pp. 117-124, (2006).

Saeed, M. et al., "Occlusive and reperfused myocardial infarcts: differentiation with Mn-DPDP-enhanced MR imaging", Radiology, vol. 172, pp. 59-64, (1989).

Shen, T. et al., "Monocrystalline iron oxide nanocompounds (MION): Physicochemical properties", Magn. Reson. Med., vol. 29, pp. 599-604, (1993).

Soriaga, M.P. et al., "Determination of the orientation of adsorbed molecules at solid-liquid interfaces by thin-layer electrochemistry: Aromatic compounds at platinum electrodes", Journal of the American Chemical Society, vol. 104, pp. 2735-2742, (1982).

Soriaga, M.P. et al., "Determination of the orientation of aromatic molecules adsorbed on platinum electrodes: The influence of iodide a surface-active anion", Journal of the American Chemical Society, vol. 104, pp. 2742-2747, (1982).

Soriaga, M.P. et al., "Determination of the orientation of aromatic molecules adsorbed on platinum electrodes: The effect of solute concentration", Journal of the American Chemical Society, vol. 104, pp. 3937-3945, (1982).

Sosnovik, D.E. et al., "Emerging concepts in molecular MRI", Current Opinion in Biotechnology, vol. 18, pp. 4-10, (2007).

Taboada, E. et al., "Relaxometric and magnetic characterization of ultrasmall iron oxide nanoparticles with high magnetization. Evaluation as potential $T_1$ magnetic resonance imaging contrast agents for molecular imaging", Langmuir, vol. 23, No. 8, pp. 4583-4588, (2007).

Tasset, D.M. et al., "Oligonucleotide inhibitors of human thrombin that bind distinct epitopes", J. Mol. Biol., vol. 272, pp. 688-698, (1997).

Tian, Y. et al., "DNAzyme amplification of molecular beacon signal", Talanta, vol. 67, pp. 532-537, (2005).

Tompkins, H.G. et al., "The study of the gas-solid interaction of acetic acid with a cuprous oxide surface using reflection-absorption spectroscopy", Journal of colloid and interface science, vol. 49, No. 3, pp. 410-421, (1974).

Tsourkas, A. et al., "Magnetic relaxation switch immunosensors detect enantiomeric impurities", Angew. Chem. Int. Ed., vol. 43, pp. 2395-2399, (2004).

Wang, S. et al., "Core/shell quantum dots with high relaxivity and photoluminescence for multimodality imaging", Journal of the American Chemical Society, vol. 129, No. 13, pp. 3848-3856, (2007).

Weissleder, R. et al., "MR imaging of splenic metastases: Ferrite-enhanced detection in rats", American Journal Roentgenol., vol. 149, pp. 723-726, (1987).

Xiao, Y. et al., "Label-free electronic detection of thrombin in blood serum by using an aptamer-based sensor", Angew. Chem. Int. Ed., vol. 44, pp. 5456-5459, (2005).

Xiao, Y. et al., "A reagentless signal-on architecture for electronic, aptamer-based sensors via target-induced strand displacement", Journal of the American Chemical Society, vol. 127, No. 51, pp. 17990-17991, (2005).

Xu, D. et al., "Label-free electrochemical detection for aptamer-based array electrodes", Analytical Chemistry, vol. 77, No. 16, pp. 6218-6224, (2005).

Yamamoto, R. et al., "Molecular beacon aptamer fluoresces in the presence of Tat protein of HIV-1", Genes to Cells, vol. 5, pp. 389-396, (2000).

Zhao, M. et al., "Magnetic sensors for protease assays", Angew. Chem. Int. Ed., vol. 42, No. 12, pp. 1375-1378, (2003).

Zhao, M. et al., "Differential conjugation of tat peptide to superparamagnetic nanoparticles and its effect on cellular uptake", Bioconjugate Chem., vol. 13, pp. 840-844, (2002).

Liu, J. et al., "Colorimetric Cu2+ detection with a ligation DNAzyme and nanoparticles", Chemical Communications, Advance Articles, DOI: 10.1039/b712421j, 6 pages, Oct. 24, 2007.

Liu, J. et al., "Non-Base pairing DNA provides a new dimension for controlling aptamer-linked nanoparticles and sensors", Journal of the American Chemical Society, vol. 129, No. 27, pp. 8634-8643, (2007).

Liu, J. et al., "Supporting Information for Colorimetric Cu2+ detection with a ligation DNAzyme and nanoparticles", Chemical Communications, Advance Articles, 4 pages, Oct. 24, 2007.

Stratagene Catolog, "Gene Characterization Kits", 2 pages, (1988).

Fahlman, R.P. et al., "DNA conformational switches as sensitive electronic sensors of analytes", Journal of the American Chemical Society, vol. 124, 4610-4616, (2002).

Mayer, G. et al., "High-throughput-compatible assay for glmS riboswitch metabolite dependence", ChemBioChem, vol. 7, pp. 602-604, (2006).

Elowe, N., et al., "Small-molecule screening made simple for a difficult target with a signaling nucleic acid aptamer that reports on deaminase activity", Angew. Chem. Int. Ed., vol. 45, pp. 5648-5652, (2006).

Yigit, M. et al., "Smart "turn-on" magnetic resonance contrast agents based on aptamer-functionalized superparamagnetic iron oxide nanoparticles", ChemBioChem, vol. 8, pp. 1675-1678, (2007).

Xu, D. et al., "Label-free electrochemical detection for aptamer-based array electrodes", Analytical Chemistry, vol. 77, No. 16, pp. 5107-5113, (2005).

Yigit, M et al., "MRI detection of thrombin with aptamer functionalized superparamagnetic iron oxide nanoparticles", Bioconjugate Chem., vol. 19, pp. 412-417, (2008).

International Search Report dated Mar. 4, 2009 for PCT application No. PCT/US2008/070177.

International Search Report dated Apr. 17, 2009 for PCT application No. PCT/US2008/051185.

International Search Report dated Aug. 13, 2009 for PCT application No. PCT/US2008/072327.

Liu, J. et al., "Rational design of turn-on allosteric DNAzyme catalytic beacons for aqueous mercury ions with ultrahigh sensitivity and selectivity", Angewandte Chemmie. International Edition, vol. 46, No. 40, pp. 7587-7590, (2007).

Stadler, B. et al., "Micropatterning of DNA-tagged vesicles", Langmuir, vol. 20, No. 26, pp. 11348-11354, (2004).

Pfeiffer, I. et al., "Bivalent cholesterol-Based coupling of oligonucleotides to lipid membrane assemblies", Journal of the American Chemical Society, vol. 126, No. 33, pp. 10224-10225, (2004).

Shin, J. et al., "Acid-triggered release via dePEGylation of DOPE liposomes containing acid-labile vinyl ether PEG-lipids", Journal of Controlled Release, vol. 91, issues 1-2, pp. 187-200, (2003).

Rusconi, C.P. et al., "Antidote-mediated control of an anticoagulant aptamer in vivo", Nature Biotechnology Letters, vol. 22, No. 11, pp. 1423-1428, (2004).

Willis M.C. et al., "Liposome-anchored vascular endothelial growth factor aptamers", Bioconjugate Chem., vol. 9, No. 5, pp. 573-582, (1998).

American Cancer Society Statistics for 2006. http://www.cancer.org/docroot/stt/stt_0.asp 2006.

Eifel, P. et al., "National Institutes of Health Consensus Development Panel, National Institutes of Health Consensus Development Conference statement: Adjuvant therapy for breast cancer, Nov. 1-3, 2000", Journal of the National Cancer Institute, vol. 93, No. 13, pp. 979-989, (2001).

Park, J.W. et al., "Tumor targeting using anti-her2 immunoliposomes", Journal of Controlled Release, vol. 74, pp. 95-113, (2001).

Kallab, V. et al., "HER2/EGFR internalization: a novel biomarker for ErbB-targeted therapeutics", Breast Cancer Research Treat., vol. 88, pp. S126-S127, (2004).

Wilson, K.S. et al., "Differential gene expression patterns in HER2/neu-positive and -negative breast cancer cell lines and tissues", American Journal of Pathology, vol. 161, No. 4, pp. 1171-1185, (2002).

Weigelt, B. et al., "Breast cancer metastasis: Markers and models", Nature Reviews, Cancer, vol. 5, pp. 591-602, (2005).

Pegram, M.D. et al., "Rational combinations of trastuzumab with chemotherapeutic drugs used in the treatment of breast cancer", Journal of the National Cancer Institute, vol. 96, No. 10, pp. 739-749, (2004).

Kirpotin, D.B. et al., "Antibody targeting of long-circulating lipidic nanoparticles does not increase tumor localization but does increase internalization in animal models", Cancer Research, vol. 66, No. 13, pp. 6732-6740, (2006).

Cheng, C. et al., "Formulation of Functionalized PLGA-PEG Nanoparticles for In Vivo Targeted Drug Delivery", Biomaterials, vol. 28, issue 5, pp. 869-876, (2007).

Bass, B.L. et al., "Specific interaction between the self-splicing RNA of Tetrahymena and its guanosine substrate: implications for biological catalysis by RNA", Nature, vol. 308, pp. 820-826, (1984).

Ellington, A.D. et al., "Combinatorial methods: aptamers and aptazymes", Part of the SPIE Conference on Advanced Materials and Opitical Systems for Chemical and Biological Detection, SPIE, vol. 3858, pp. 126-134, (1999).

Robertson, M.P. et al., "Aptazymes as generalized signal transducers", Nucleic Acids Symp. Ser., vol. 41, pp. 1-3, (1999).

Pagratis, N.C. et al., "Potent 2'-amino-, and 2'-fluoro-2'-deoxyribonucleotide RNA inhibitors of keratinocyte growth factor", Nature Biotechnology, vol. 15, pp. 68-73, (1997).

Lupold, S.E. et al., "Identification and characterization of nuclease-stabilized RNA molecules that bind human prostate cancer cells via the prostate-specific membrane antigen", Cancer research, vol. 62, pp. 4029-4033, (2002).

Jenison, R.D. et al., "Oligonucleotide inhibitors of P-selectin-dependent neutrophil-platelet adhesion", Antisense Nucleic Acid Drug Dev., vol. 8, pp. 265-279, (1998).

Hicke, B.J. et al., "DNA aptamers block L-selectin function in vivo. Inhibition of human lymphocyte trafficking in SCID mice", J. Clinical Invest., vol. 98, No. 12, pp. 2688-2692, (1996).

O'Connell, D. et al., "Calcium-dependent oligonucleotide antagonists specific for L-selectin", Proceedings of the National Academy of Science, U.S.A., vol. 93, pp. 5883-5887, (1996).

Soukup, G.A. et al., "Design of allosteric hammerhead ribozymes activated by ligand-induced structure stabilization", Structure, vol. 7, pp. 783-791, (1999).

Straubinger, R.M. et al., "Preparation and characterization of taxane-containing liposomes", Methods in Enzymology, vol. 391, pp. 97-117, (2005).

Rivera, E. "Liposomal anthracyclines in metastatic breast cancer: Clinical update", The Oncologist, vol. 8, supplement 2, pp. 3-9, (2003).

Kornblith, P. et al., "Breast cancer—Response rates to chemotherapeutic agents studied in vitro", Anticancer Research, vol. 23, pp. 3405-3411, (2003).

Pei, J. et al., "Combination with liposome-entrapped, ends-modified raf antisense oligonucleotide (LErafAON) improves the anti-tumor efficacies of cisplatin, epirubicin, mitoxantrone, docetaxel and gemcitabine", Anti-Cancer Drugs, vol. 15, pp. 243-253, (2004).

Allen, T.M. et al., "Therapeutic opportunities for targeted liposomal drug delivery", Advanced Drug Delivery Reviews, vol. 21, pp. 117-133, (1996).

Hofheinz, R.D. et al., "Liposomal encapsulated anti-cancer drugs", Anti-Cancer Drugs, vol. 16, pp. 691-707, (2005).

Schluep, T. et al., "Preclinical efficacy of the camptothecin-polymer conjugate IT-101 in multiple cancer models", Clinical Cancer Research, vol. 12, No. 5, pp. 1606-1614, (2006).

Schluep, T. et al., "Pharmacokinetics and biodistribution of the camptothecin-polymer conjugate IT-101 in rats and tumor-bearing mice", Cancer Chemoth. Pharm., vol. 57, pp. 654-662, (2006).

Cheng, J. et al., "Antitumor Activity of beta-Cyclodextrin Polymer-Camptothecin Conjugates", Molecular Pharmaceutics, vol. 1, No. 3, pp. 183-193, (2004).

Cheng, J. et al., "Synthesis of linear, beta-cyclodextrin-based polymers and their camptothecin conjugates", Bioconjugate Chem., vol. 14, pp. 1007-1017, (2003).

Guo, X. et al., "Steric stabilization of fusogenic liposomes by a low-pH sensitive PEG-diortho ester-lipid conjugate", Bioconjugate Chem., vol. 12, pp. 291-300, (2001).

Gerasimov, O.V. et al., "Cytosolic drug delivery using pH- and light-sensitive liposomes", Advanced Drug Delivery Reviews., vol. 38, pp. 317-338, (1999).

Rovira-Bru, M. et al., "Size and structure of spontaneously forming liposomes in lipid/PEG-lipid mixtures", Biophysical Journal, vol. 83, pp. 2419-2439, (2002).

Liu, J. et al., "Proofreading and error removal in a nanomaterial assembly", Angewandte Chemie, International Edition, vol. 44, pp. 7290-7293, (2005).

Liu, J. et al., "Design of asymmetric DNAzymes for dynamic control of nanoparticle aggregation states in response to chemical stimuli", Organic & Biomolecular Chemistry, vol. 4, pp. 3435-3441, (2006).

Cho, H.S. et al., "Structure of the extracellular region of HER2 alone and in complex with the Herceptin Fab", Nature, vol. 421, pp. 756-760, (2003).

Leahy, D.J. et al., "A Mammalian Expression Vector for Expression and Purification of Secreted Proteins for Structural Studies", Protein Expression and Purification, vol. 20, pp. 500-506, (2000).

Bartel, D.P. et al., "Isolation of new ribozymes from a large pool of random sequences", Science, vol. 261, pp. 1411-1418, (1993).

Jellinek, D. et al., "Inhibition of receptor binding by high-affinity RNA ligands to vascular endothelial growth factor", Biochemistry, vol. 33, pp. 10450-10456, (1994).

Jellinek, D. et al., "Potent 2'-Amino-2'-deoxypyrimidine RNA Inhibitors of Basic Fibroblast Growth Factor", Biochemistry, vol. 34, pp. 11363-11372, (1995).

Green, L.S. et al., "Inhibitory DNA Ligands to Platelet-Derived Growth Factor B-Chain", Biochemistry, vol. 35, pp. 14413-14424, (1996).

Lee, T.C. et al., "Overexpression of RRE-derived sequences inhibits HIV-1 replication in CEM cells", New Biologist, vol. 4, p. 66, (1992).

Andresen, T.L. et al., "Advanced strategies in liposomal cancer therapy: Problems and prospects of active and tumor specific drug release", Progress in Lipid Research, vol. 44, pp. 68-97, (2005).

Woodle, M.C. et al., "Sterically Stabilized Liposomes—Reduction in electrophoretic mobility but not electrostatic surface potential", Biophysical Journal, vol. 61, pp. 902-910, (1992).

Zalipsky, S. et al., "Long Circulating, Cationic Liposomes Containing Amino-Peg-Phosphatidylethanolamine", FEBS Letters, vol. 353, pp. 71-74, (1994).

Morrison, W., "A fast, simple and reliable method for the microdetermination of phosphorus in biological materials", Analytical Biochemistry, vol. 7, issue 2, pp. 218-224, (1964).

Kirpotin, D. et al., "Sterically Stabilized Anti-HER2 Immunoliposomes: Design and Targeting to Human Breast Cancer Cells in Vitro", Biochemistry, vol. 36, pp. 66-75, (1997).

Klibanov, A.L. et al., "Activity of Amphipathic Poly(Ethylene Glycol)-5000 to Prolong the Circulation Time of Liposomes Depends on the Liposome Size and Is Unfavorable for Immunoliposome Binding to Target", Biochim. Biophys. Acta, vol. 1062, pp. 142-148, (1991).

Park, J.W. et al., "Development of Anti-P185$^{HER2}$ Immunoliposomes for Cancer-Therapy", Proceedings of the National Academy of Science U.S.A., vol. 92, pp. 1327-1331, (1995).

Zalipsky, S. "Synthesis of an End-Group Functionalized Polyethylene Glycol-Lipid Conjugate for Preparation of Polymer-Grafted Liposomes", Bioconjugate Chem., vol. 4, pp. 296-299, (1993).

Allen, T.M. et al., "A New Strategy for Attachment of Antibodies to Sterically Stabilized Liposomes Resulting in Efficient Targeting to Cancer-Cells", Biochimica et Biophysica Acta, vol. 1237, pp. 99-108, (1995).

Gillies, E.R. et al., "A new approach towards acid sensitive copolymer micelles for drug delivery", Chemical Communications, Issue 14, pp. 1640-1641, (2003).

Joensuu, O.I., "Fossil Fuels as a Source of Mercury Pollution", Science, vol. 172, No. 3987, pp. 1027-1028, (1971).

Malm, O., "Gold mining as a source of mercury exposure in the Brazilian Amazon", Environmental Research, vol. 77, No. 2, pp. 73-78, (1998).

Tchounwou, P.B. et al., "Environmental exposure to mercury and its toxicopathologic implications for public health", Environmental Toxicology, vol. 18, No. 3, pp. 149-175, (2003).

Yoon, S. et al., "A bright and specific fluorescent sensor for mercury in water, cells, and tissue", Angewandte Chemie International Edition, vol. 46, No. 35, pp. 6658-6661, (2007).

Liu, X.F. et al., "Optical detection of mercury(II) in aqueous solutions by using conjugated polymers and label-free oligonucleotides", Advanced Materials, vol. 19, No. 11, p. 1471, (2007).

Chiang, C.K. et al., "Oligonucleotide-based fluorescence probe for sensitive and selective detection of mercury(II) in aqueous solution", Analytical Chemistry, vol. 80, No. 10, pp. 3716-3721, (2008).

Yamini, Y. et al., "Solid phase extraction and determination of ultra trace amounts of mercury(II) using octadecyl silica membrane disks modified by hexathia-18-crown-6-tetraone and cold vapour atomic absorption spectrometry", Analytica Chimica Acta, vol. 355, issue 1, pp. 69-74, (1997).

Darbha, G.K. et al., "Gold nanoparticle-based miniaturized nanomaterial surface energy transfer probe for rapid and ultrasensitive detection of mercury in soil, water, and fish", Acs Nano, vol. 1, No. 3, pp. 208-214, (2007).

Li, D. et al., "Optical analysis of Hg2+ ions by oligonucleotide-gold-nanoparticle hybrids and DNA-based machines", Angewandte Chemie International Edition, vol. 47, No. 21, pp. 3927-3931, (2008).

Liu, C.W. et al., "Detection of mercury(II) based on Hg2+-DNA complexes inducing the aggregation of gold nanoparticles", Chemical Communications, vol. 19, pp. 2242-2244, (2008).

Xue, X. et al., "One-step, room temperature, colorimetric detection of mercury (Hg2+) using DNA/nanoparticle conjugates", Journal of the American Chemical Society, vol. 130, No. 11, pp. 3244-3245, (2008).

Wang, L. et al., "Gold nanoparticle-based optical probes for target-responsive DNA structures", Gold Bulletin, vol. 41, No. 1, pp. 37-41, (2008).

Clarkson, T.W. et al., "Mercury—Major Issues in Environmental-Health", Environmental Health Perspectives, vol. 100, pp. 31-38, (1993).

Wren, C.D. "A Review of Metal Accumulation and Toxicity in Wild Mammals, 1 Mercury", Environmental Research, vol. 40, No. 1, pp. 210-244, (1986).

Koos, B.J. et al., "Mercury Toxicity in Pregnant Woman, Fetus, and Newborn-Infant-Review", American Journal of Obstetrics and Gynecology, vol. 126, No. 3, pp. 390-409, (1976).

Yu, Y. et al., "p-dimethylaminobenzaldehyde thiosemicarbazone: A simple novel selective and sensitive fluorescent sensor for mercury(II) in aqueous solution", Talanta, vol. 69, No. 1, pp. 103-106, (2006).

Braman, R.S., "Membrane Probe—Spectral Emission Type Detection System for Mercury in Water", Analytical Chemistry, vol. 43, No. 11, pp. 1462-1467, (1971).

Wernette, D.P. et al., "Surface immobilization of catalytic beacons based on ratiometric fluorescent DNAzyme sensors: a systematic study", Langmuir, vol. 23, No. 18, pp. 9513-9521, (2007).

Wang, Z. et al., "Highly sensitive "turn-on" fluorescent sensor for Hg2+ in aqueous solution based on structure-switching DNA", Chemical Communications, pp. 6005-6007, (2008).

Lu, Y. "New catalytic DNA fluorescent and colorimetric sensors for on-sit and real-time monitoring of industrial and drinking water", ISTC Reports, Illinois Sustainable Technology Center Institute of Natural Resource Sustainability, University of Illinois at Urbana-Champaign, http://www.istc.illinois.edu/info/library_docs/RR/RR-114.pdf, pp. i-ix, and 1-30, (2009).

Turner, A. P. F., "Biochemistry: Biosensors—Sense and Sensitivity", Science, vol. 290, No. 5495, pp. 1315-1317, (2000).

Abbasi, S. A., "Atomic absorption spectrometric and spectrophotometric trace analysis of uranium in environmental samples with n-p-methoxyphenyl-2-4-(2-pyridylazo) resorcinol", Int. J. Environ. Anal. Chem., vol. 36, pp. 163-172, (1989).

Arnez, J. G. et al., "Crystal structure of unmodified tRNA$^{Gln}$ complexed with glutaminyl-tRNA synthetase and ATP suggests a possible role for pseudo-uridines in stabilization of RNA structure", Biochemistry, vol. 33, pp. 7560-7567, (1994).

Blake, R. C., II, et al., "Novel monoclonal antibodies with specificity for chelated uranium (VI): isolation and binding properties", Bioconjug. Chem., vol. 15, pp. 1125-1136, (2004).

Boomer, D. W., et al, "Determination of uranium in environmental samples using inductively coupled plasma mass spectrometry", Anal. Chem., vol. 59, pp. 2810-2813, (1987).

Breaker, R. R., "Natural and engineered nucleic acids as tools to explore biology", Nature, vol. 432, pp. 838-845, (2004).

Brina, R. et al., "Direct detection of trace levels of uranium by laser-induced kinetic phosphorimetry", Anal. Chem., vol. 64, pp. 1413-1418, (1992).

Chung N. et al., "Selective extraction of gold(III) in the presences of Pd(II) and Pt(IV) by saltin-out of the mixture of 2-propanol and water", Talanta, vol. 58, pp. 927-933, (2002).

Craft, E. et al., "Depleted and natural uranium: chemistry and toxicological effects", J. Toxicol. Environ. Health, Part B, vol. 7, pp. 297-317, (2004).

Demers, L. M. et al., "Thermal desorption behavior and binding properties of DNA bases and nucleosides on gold", J. Am. Chem. Soc. vol. 124, pp. 11248-11249, (2002).

Frankforter G. et al., "Equilibria in the systems of the higher alcohols, water and salts", J. Am. Chem. Soc., vol. 37, pp. 2697-2716 (1915).

Frankforter G., et al., "Equilibria in the systems, water, acetone and inorganic salts", J. Am. Chem. Soc., vol. 36, pp. 1103-1134, (1914).

Frankforter G., et al., "Equilibria in systems containing alcohols, salts and water, including a new method of alcohol analysis", J. Phys. Chem., vol. 17, pp. 402-473, (1913).

Ginnings, P. et al., "Ternary systems: water, tertiary butanol and salts at 30° C.", J. Am. Chem. Soc., vol. 52, pp. 2282-2286, (1930).

Gongalsky, K., "Impact of pollution caused by uranium production on soil macrofauna", Environ. Monit. Assess., vol. 89, pp. 197-219, (2003).

Homola, J. et al., "Surface Plasmon Resonance (SPR) Sensors", Springer Series on Chemical Sensors and Biosensors, vol. 4, pp. 45-67, (2006).

US EPA, "Drinking water contaminants", found at http://www.epa.gov/safewater/contaminants/index.html, pp. 1-17, printed on Nov. 23, 2009.

Jones, L. A., et al., "Extraction of phenol and its metabolites from aqueous solution", J. Agric. Food Chem., vol. 41, pp. 735-741, (1993).

Katz, E. et al., "Integrated nanoparticle-biomolecule hybrid systems: sythesis, properties, and applications", Angew. Chem. Int. Ed., vol. 43, pp. 6042-6108, (2004).

Kobe, K. A. et al., "The ternary systems ethylene glycol-potassium carbonate-water and dioxane-potassium carbonate-water", J. Phys. Chem., vol. 446, pp. 629-633, (1940).

Laromaine, A. et al., "Protease-triggered dispersion of nanoparticle assemblies", J. Am. Chem. Soc., vol. 129, pp. 4156-4157, (2007).

Lazarova, Z. et al., "Solvent extraction of lactic acid from aqueous solution", Journal of Biotechnology, vol. 32, pp. 75-82, (1994).

Lee, J. H. et al., "Site-specific control of distances between gold nanoparticles using phosphorothioate anchors on DNA and a short bifunctional molecular fastener", Angew. Chem. Int. Ed., vol. 46, pp. 9006-9010, (2007).

Leggett, D. C. et al., "Salting-out solvent extraction for preconcentration of neutral polar organic solutes from water", Anal. Chem., vol. 62, pp. 1355-1356, (1990).

Leinonen, H., "Stress corrosion cracking and life prediction evaluation of austenitic stainless steels in calcium chloride solution", Corrosion Science, vol. 52, No. 5, pp. 337-346, (1996).

Li, D. et al., "Amplified electrochemical detection of DNA through the aggregation of Au nanoparticles on elctrodes and the incorporation of methylene blue into the DNA-crosslinked structure", Chem. Comm., pp. 3544-3546, (2007).

Li, H. et al., "Detection of specific sequences in rna using differential adsorption of single-stranded oligonucleotides on gold nanoparticles", Anal. Chem., vol. 77 No. 19, pp. 6229-6233, (2005).

Li, H. et al., "Colorimetric detection of dna sequences based on electrostatic interactions with unmodified gold nanoparticles", Proc. Natl. Acad. Sci. U.S.A., vol. 101, pp. 14036-14039, (2004).

Li, H. et al., "Label-free colorimetric detection of specific sequences in genomic dna amplified by the polymerase chain reaction", J. Am. Chem. Soc., vol. 126, pp. 10958-10961, (2004).

Likidis, Z. et al., "Recovery of penicillin G from fermentation broth with reactive extraction in a mixer-settler", Biotechnology Letters, vol. 9, No. 4, pp. 229-232, (1987).

Lim, I. et al., "Homocysteine-mediated reactivity and assembly of gold nanoparticles", Langmuir, vol. 23, pp. 826-833, (2007).

Lu, Y. et al., "Functional DNA nanotechnology:emerging applications of DNAzymes and aptamers", Curr. Opion. Biotech., vol. 17, pp. 580-588, (2006).

Long, F. A., et al., "Activity coefficients of nonelectrolyte solutes in aqueous salt solutions", Chem. Rev., vol. 51, pp. 119-169, (1952).

Lu, X. et al., "Salting-out separation and liquid-liquid equilibrium of tertiary butanol aqueous solution", Chemical Engineering Journal, vol. 78, pp. 165-171, (2000).

Lu, Y. et al., "Smart nanomaterials inspired by biology: dynamic assembly of error-free nanomaterials in response to multiple chemical and biological stimuli", Accounts of Chemical Research, vol. 40, pp. 315-323, (2007).

Mlakar, M. et al., "Stripping voltammetric determination of trace levels of uranium by synergic adsorptions", Analytica Chimica Acta, vol. 221, pp. 279-287, (1989).

Nishihama, S., "Review of advanced liquid-liquid extraction systems for the separation of metal ions by a combination of conversion of the metal species with chemical reaction", Ind. Eng. Chem. Res., vol. 40, pp. 3085-3091, (2001).

Pierotti, R. A., "A scaled particle theory of aqueous and nonaqueous solutions", Chemical Reviews, vol. 76, No. 6, pp. 717-726, (1976).

Centers for Disease Control, "Preventing lead poisoning in young children", U.S. Department of Health and Human Services, Public Health Service, Centers for Disease Control: Atlanta, GA, (1991).

Public Law 102-550; Residential Lead-Based Paint Hazard Reduction Act of the housing and Community Development Act of 1992; 28 pages, (1992).

Qiang, Z. et al., "Potentiometric determination of acid dissociation constants (pK$_a$) for human and veterinary antibiotics", Water Research, vol. 38, pp. 2874-2890, (2004).

Rohwer, H. et al., "Interactions of uranium and thorium with arsenazo III in an aqueous medium", Analytica Chimica Acta, vol. 341, pp. 263-268, (1997).

Safavi, A. et al., "A novel optical sensor for uranium determination", Analytica Chimica Acta vol. 530, pp. 55-60, (2005).

Sato, K. et al., "Rapid aggregation of gold nanoparticles induced by non-cross-linking DNA hybridization", J. Am. Chem. Soc., vol. 125, pp. 8102-8103, (2003).

Schenk, F. J. et. al., "Comparison of magnesium sulfate and sodium sulfate for removal of water from pesticide extracts of foods", J. AOAC International, vol. 85, No. 5, pp. 1177-1180, (2002).

Sessler, J. L. et al., "Hexaphyrin (1.0.1.0.0.0). a new colorimetric actinide sensor", Tetrahedron, vol. 60, pp. 11089-11097, (2004).

Shafer-Peltier, K. E. et al., "Toward a glucose biosensor based on surface-enhanced raman scattering", J. Am. Chem. Soc., vol. 125, pp. 588-593, (2003).

Sharma, J. et al., "DNA-templated self-assembly of two-dimensional and periodical gold nanoparticle arrays", Angew. Chem. Int. Ed., vol. 45, pp. 730-735, (2006).

Si, S. et al., "pH-controlled reversible assembly of peptide-functionalized gold nanoparticles", Langmuir, vol. 23, pp. 190-195, (2007).

Simard, J. et al., "Formation and pH-controlled assembly of amphiphilic gold nanoparticles", Chemical Commun., pp. 1943-1944, (2000).

Singleton, V. L., "An extraction technique for recovery of flavors, pigments, and other constituents from wines and other aqueous solutions", Am. J. Enol. Vitic., vol. 12, pp. 1-8, (1961).

Rao, C.V.S.R. et al., "Extraction of acetonitrile from aqueous solutions. 1. Ternary liquid equilibria", Journal of Chemical and Engineering Data, vol. 23, No. 1, pp. 23-25, (1978).

Rao, D.S. et al., "Extraction of acetonitrile from aqueous solutions. 2. ternary liquid equilibria", Journal of Chemical and Engineering Data, vol. 24, No. 3, pp. 241-244, (1979).

Tabata, M. et al., "Ion-pair extraction of metalloporphyrins into acetonitrile for determination of copper(II)", Analytical Chemistry, vol. 68, No. 5, pp. 758-762, (1996).

Tabata, M. et al., "Chemical properties of water-miscible solvents separated by salting-out and their application to solvent extraction", Analytical sciences, vol. 10, pp. 383-388, (1994).

Van der Wal, Sj., "Low viscosity organic modifiers in reversed-phase HPLC", Chromatographia, vol. 20, No. 5, pp. 274-278, (1985).

Wang, J. et al., "A gold nanoparticle-based aptamer target binding readout for ATP assay", Adv. Mater., vol. 19, pp. 3943-3946, (2007).

Wang, L. et al., "Unmodified gold nanoparticles as a colorimetric probe for potassium DNA aptamers", Chem. Comm., vol. 36, 3780-3782, (2006).

Wang, Z. et al., "Label-free colorimetric detection of lead ions with a nanomolar detection limit and tunable dynamic range by using gold nanoparticles and DNAzyme", Advanced Materials, vol. 20, pp. 3263-3267. (2008).

Warren, K. W., Reduction of corrosion through improvements in desalting, Benelux Refinery Symposium, Lanaken, Belgium, 11 pages, (1995).

Wei, H. et al., "Simple and sensitive aptamer-based colorimetric sensing of protein using unmodified gold nanoparticle probes", Chem. Comm., vol. 36, pp. 3735-3737, (2007).

Wernette, D. P. et al., "Surface immobilization of catalytic beacons based on ratiometric fluorescent DNAzyme sensors: A systematic study", Langmuir, vol. 23, pp. 9513-9521, (2007).

Willner, I. et al., "Electronic aptamer-based sensors", Angew. Chem., Int. Ed., vol. 46, pp. 6408-6418, (2007).

Wu, Y. G., et al., "An extended Johnson-Furter equation to salting-out phase separation of aqueous solution of water-miscible organic solvents", Fluid Phase Equilibria, vol. 192, pp. 1-12, (2001).

Yan, H., "Nucleic acid nanotechnology", Science, vol. 306, pp. 2048-2049, (2004).

Yang, W. H. et al., "Discrete dipole approximation for calculating extinction and raman intensities for small particles with arbitrary shapes", J. Chem. Phys., vol. 103, pp. 869-875, (1995).

Deng, Z. et al., "DNA-Encoded self-assembly of gold nanoparticles into one-dimensional arrays", Angew. Chem. Int. Ed., vol. 44, pp. 3582-3585, (2005).

Zhao, W. et al., "Simple and rapid colorimetric biosensors based on DNA aptamer and noncrosslinking gold naoparticle aggregation", ChemBioChem, vol. 8, pp. 727-731, (2007).

Zhao, W. et al., "Highly stabilized nucleotide-capped small gold nanoparticles with tunable size", Advanced Materials vol. 19, pp. 1766-1771, (2007).

Zhao, W. et al., "DNA polymerization on gold nanoparticles through rolling circle amplification: towards novel scaffolds for three-dimensional periodic nanoassemblies", Angew. Chem. Int. Ed., vol. 45, pp. 2409-2413, (2006).

Zhao, W. et al., "DNA aptamer folding on gold nanoparticles: from colloid chemistry to bionsenors", J. Am. Chem. Soc., vol. 130, (11), pp. 3610-3618, (2008).

Zhou, P. et al., "Extraction of oxidized and reduced forms of uranium from contaminated soils: effects of carbonate concentration pH", Environmental Science Technology, vol. 39, No. 12, pp. 4435-4440, (2005).

Jacoby, M., "Sensitive, selective mercury sensor nanoparticle-based colorimetric method detects part-per-billion levels of mercury", Chemical & Engineering News, pp. 1-3, May 2, 2007.

Cruz, R.P.G. et al., supplemental to "Dinucleotide junction cleavage versatility of 8-17 deoxyribozyme", Chemistry & Biology, vol. 11, pp. 57-67, (pp. 1-8) (2004).

Saleh, O. A. et al., "Direct detection of antibody-antigen binding using an on-chip artificial pore", Proceedings of the National Academy of Science, vol. 100, No. 3, pp. 820-824, (2003).

Han, C. et al., "Highly selective and sensitive colorimetric probes for $Yb^{3+}$ ions based on supramolecular aggregates assembled from B-cyclodextrin-4,4'-dipyridine inclusion complex modified silver nanoparticles", Chem. Commun., pp. 3545-3547, (2009).

Aldaye, F.A., et al., "Sequential Self-Assembly of a DNA Hexagon as a Template for the Organization of Gold Nanoparticles", Angew. Chem. Int. Ed., 45, pp. 2204-2209, 2006.

Loweth, C.J. et al., "DNA-Based Assembly of Gold Nanocrystals", Angew. Chem. Int. Ed., 38, No. 12, pp. 1808-1812, 1999.

Carbone, A., et al., "Circuits and programmable self-assembling DNA structures", Proceedings of the National Academy of Sciences of the United States of America, vol. 99, No. 20, pp. 12577-12582, 2002.

Chelyapov, N., et al., "DNA Triangles and Self-Assembled Hexagonal Tilings", J. Am. Chem. Soc., 126, pp. 13924-13925, 2004.

Conway, N.E., et al., "The Covalent Attachment of Multiple Fluorophores to DNA Containing Phosphorothioate Diesters Results in Highly Sensitive Detection of Single-Stranded DNA", Bioconjugate Chem, 2, pp. 452-457, 1991.

Ding, B., et al., "Pseudohexagonal 2D DNA Crystals from Double Crossover Cohesion", J. Am. Chem. Soc., 126, pp. 10230-10231, 2004.

Endo, M., et al., "DNA Tube Structures Controlled by a Four-Way-Branched DNA Connector", Angew. Chem. Int. Ed., 44, pp. 6074-6077, 2005.

Fidanza, J.A, et al. "Site-Specific Labeling of DNA Sequences Containing Phosphorothioate Diesters", J. Am. Chem. Soc., 114, pp. 5509-5517, 1992.

Goodman, R.P., et al., "Rapid Chiral Assembly of Rigid DNA Building Blocks for Molecular Nanofabrication", Science, 310, pp. 1661-1665, 2005.

Hagleitner, C., et al., "Smart single-chip gas sensor microsystem", Nature, vol. 414, pp. 293-296, 2001.

He, Y., et al., "Sequence Symmetry as a Tool for Designing DNA Nanostructures", Angew. Chem. Int. Ed., 44, pp. 6694-6696, 2005.

Heath, J.R., et al., "A Defect-Tolerant Computer Architecture: Opportunities for Nanotechnology", Science, vol. 280, pp. 1716-1719, 1998.

Holloway, G., et al., "An Organometallic Route to Oligonucleotides Containing Phosphoroselenoate", ChemBioChem, 3, pp. 1061-1065, 2002.

Li, H., et al., "DNA-Templated Self-Assembly of Protein and Nanoparticle Linear Arrays", J. Am. Chem. Soc., 126, pp. 418-419, 2004.

Cunningham, L., et al., "Spectroscopic Evidence for Inner-Sphere Coordination of Metal Ions to the Active Site of a Hammerhead Ribozyme", J. Am. Chem. Soc., 120, pp. 4518-4519, 1998.

Luduena, R.F., et al., N,N-Bis(α-iodoacetyl)-2,2'-dithiobis(ethylamine), a Reversible Crosslinking Reagent for Protein Sulfhydryl Groups, Analytical Biochemistry, 117. pp. 76-80, 1981.

Lund, K., et al., "Self-Assembling a Molecular Pegboard", J. Am. Chem. Soc., 127, pp. 17606-17607, 2005.

Mathieu, F., et al. "Six-Helix Bundles Designed from DNA", Nano Letters, vol. 5, No. 4, pp. 661-665, 2005.

Liu, H., et al, "Approaching the Limit: Can One DNA Oligonucleotide Assemble into Large Nanostructures?", Angew. Chem., 118, pp. 1976-1979, 2006.

Fidanza, J. et al, "Introduction of Reporter Groups at Specific Sites in DNA Containing Phosphorothioate Diesters", J. Am. Chem. Soc., 111, pp. 9117-9119, 1989.

Nakao, H., et al, "Highly Ordered Assemblies of Au Nanoparticles Organized on DNA", Nano Letters, vol. 3, No. 10, pp. 1391-1394, 2003.

Patolsky, F., et al., "Au-Nanoparticle Nanowires Based on DNA and Polylysine Templates", Angew. Chem. Int. Ed., 41, No. 13, pp. 2323-2327, 2002.

Pinto, Y., et al., "Sequence-Encoded Self-Assembly of Multiple-Nanocomponent Arrays by 2D DNA Scaffolding", Nano Letters, vol. 5, No. 12, pp. 2399-2402, 2005.

Rothemund, P., "Folding DNA to create nanoscale shapes and patterns", Nature, vol. 440, pp. 297-302, 2006.

Yang, X., et al, "Ligation of DNA Triangles Containing Double Crossover Molecules", J. Am. Chem. Soc., 120, pp. 9779-9786, 1998.

Seeman, N.C., "Nucleic Acid Nanostructures and Topology", Angew. Chem. Int. Ed., 37, pp. 3220-3238, 1998.

Seeman, N. C., "At the Crossroads of Chemistry, Biology, and Materials: Structural DNA Nanotechnology", Chemistry & Biology, vol. 10, pp. 1151-1159, 2003.

Le, J.D., et al., "DNA-Templated Self-Assembly of Metallic Nanocomponent Arrays on a Surface", Nano Letters, vol. 4, No. 12, pp. 2343-2347, 2004.

Seeman, N.C., et al. "Nucleic acid nanostructures: bottom-up control of geometry on the nanoscale", Reports on Progress in Physics, 68, pp. 237-270, 2005.

Warner, M.G., et al., "Linear assemblies of nanoparticles electrostatically organized on DNA scaffolds", Nature Materials, vol. 2, pp. 272-277, 2003.

Winfree, E., et al., "Design and self-assembly of two-dimensional DNA crystals", Nature, vol. 394, pp. 539-544, 1998.

Woehrle, G.H., et al., "Molecular-Level Control of Feature Separation in One-Dimensional Nanostructure Assemblies Formed by Biomolecular Nanolithography", Langmuir, 20, pp. 5982-5988, 2004.

Zhang, J., et al, "Periodic Square-Like Gold Nanoparticle Arrays Templated by Self-Assembled 2D DNA Nanogrids on a Surface", Nano Letters, vol. 6, No. 2, pp. 248-251, 2006.

Yang, T. et al. "Tunneling Phase Logic Cellular Nonlinear Networks", International Journal of Bifurcation and Chaos, vol. 11, No. 12, pp. 2895-2911, 2001.

Liu, Z., et al., "Imaging DNA Molecules on Mica Surface by Atomic Force Microscopy in Air and in Liquid", Microscopy Research and Technique, 66, pp. 179-185, 2005.

Niemeyer, C.M., et al., "Covalent DNA-Streptavidin Conjugates as Building Blocks for Novel Biometallic Nanostructures", Angew. Chem. Int. Ed., 37, No. 16, pp. 2265-2268, 1998.

"What wavelength goes with a color" from eosweb. larc. Nasa.gov. Printed on Jan. 7, 2011.

Cadmium sulfide from Wikipedia, the free encyclopedia. Printed on Jan. 7, 2011.

Yeh et al., Quantum dot-mediated biosensing assays for specific nucleic acid detection. Nanomedicine, 1, 115-121, 2005.

* cited by examiner

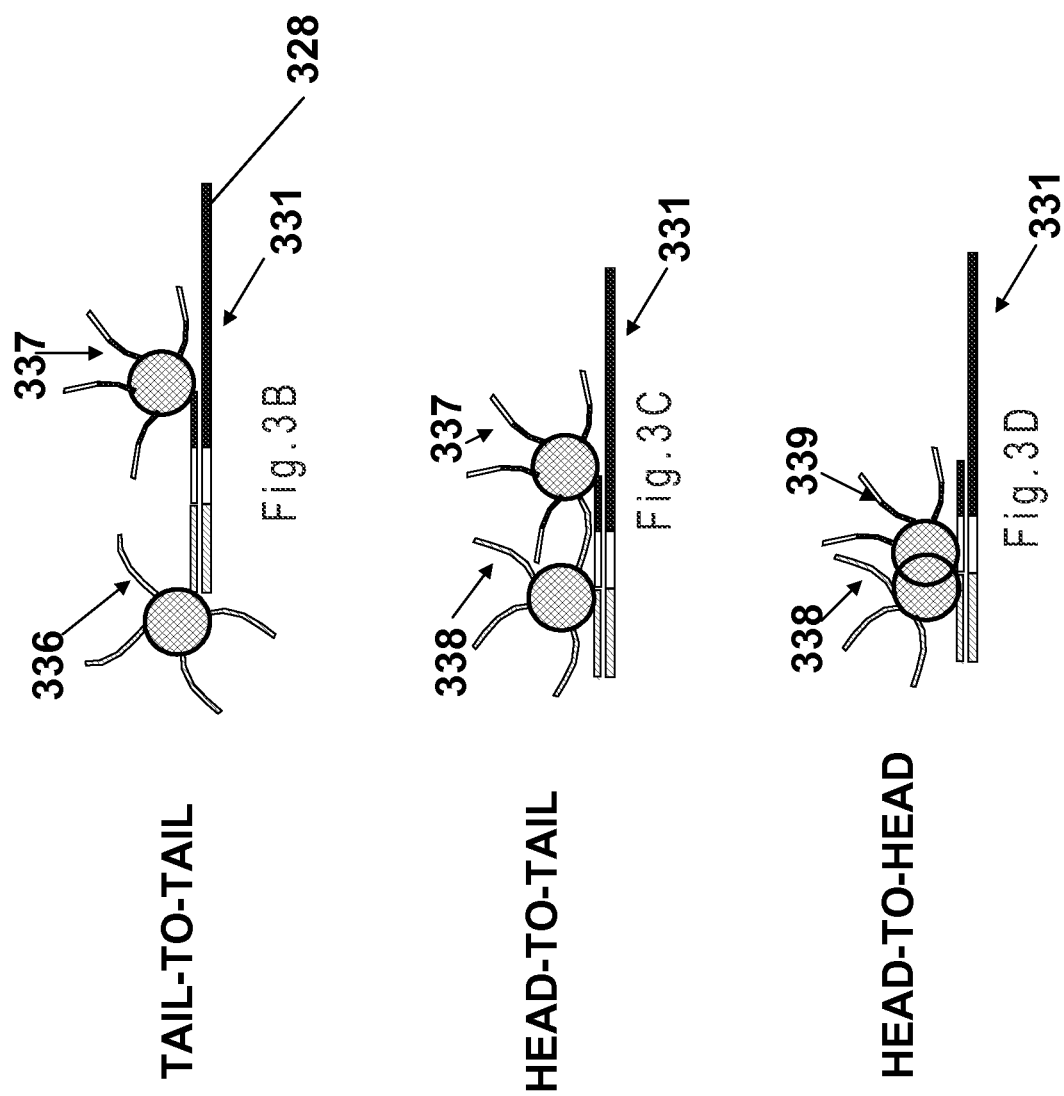

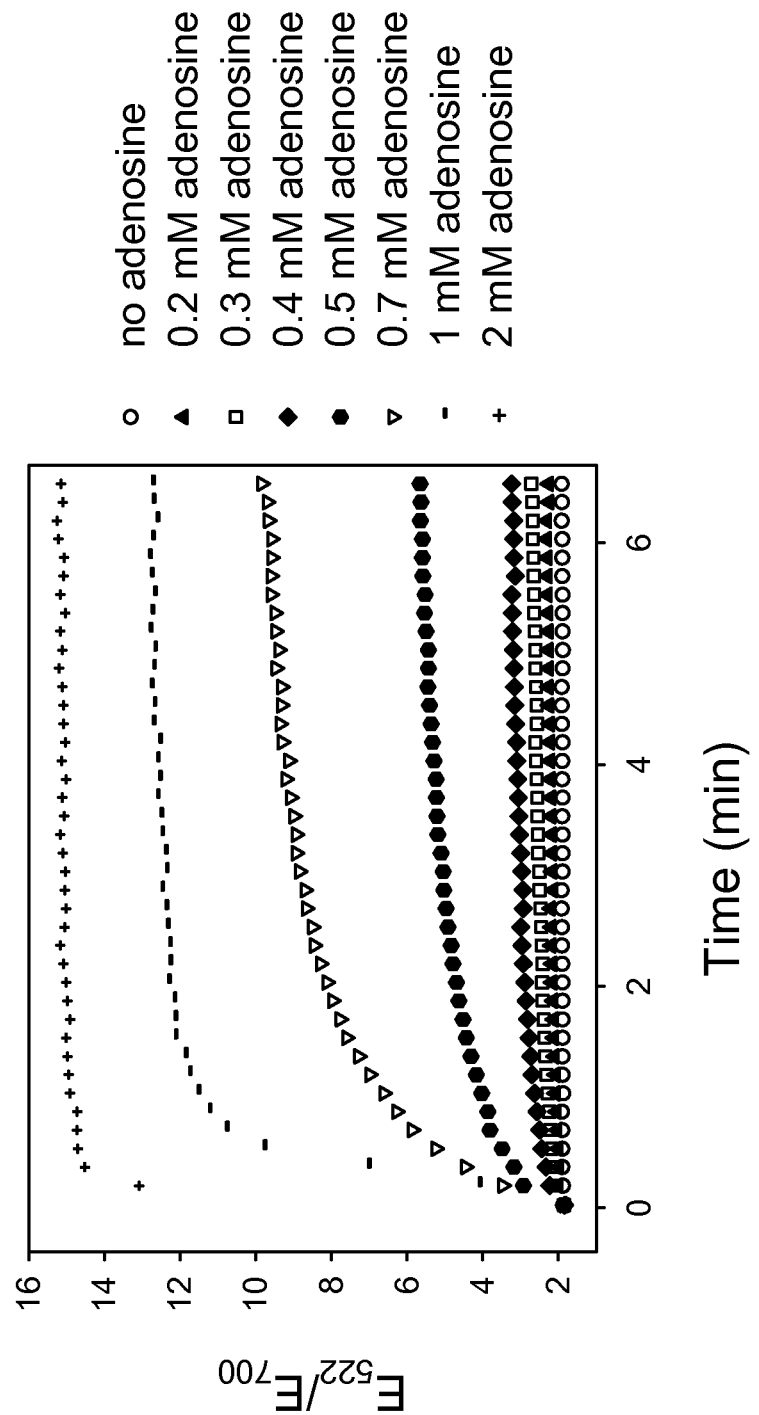

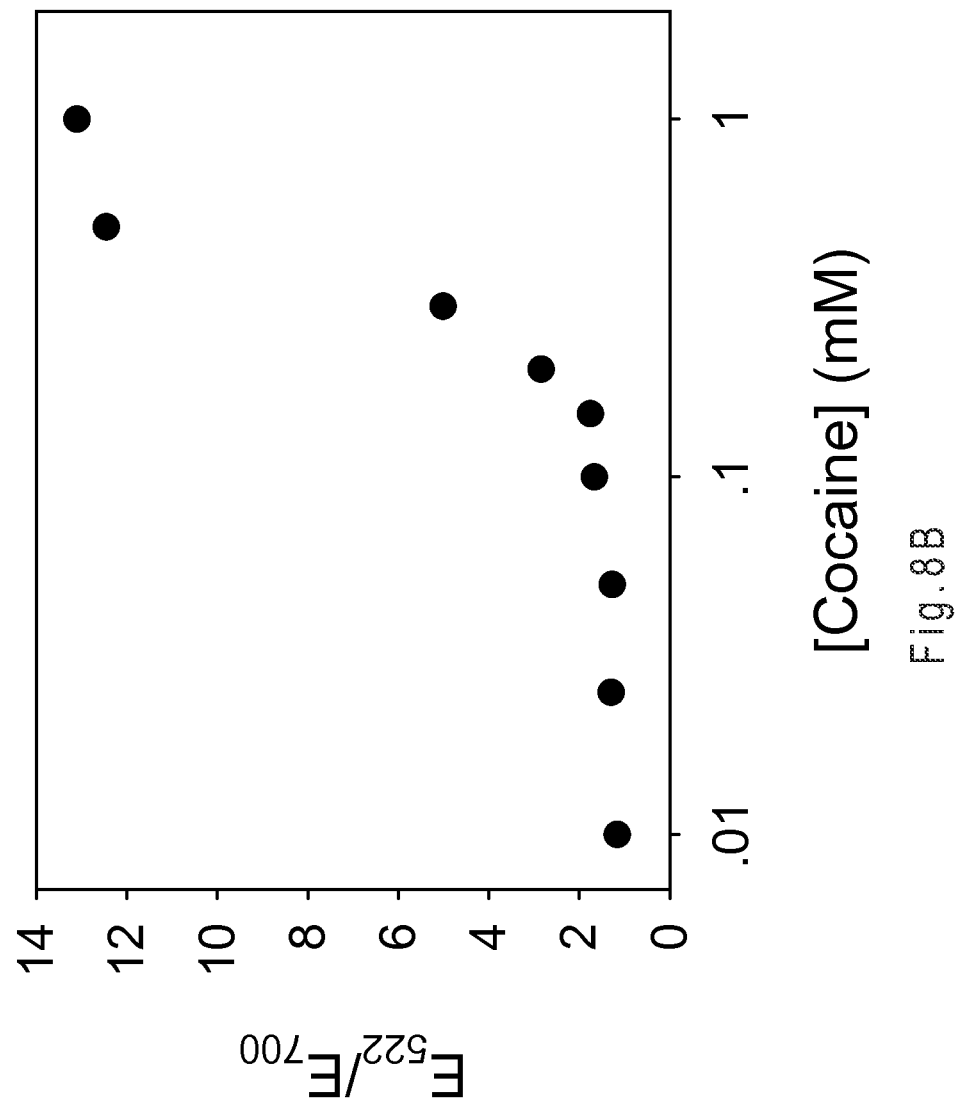

```
                        SEQUENCE LISTING

<160> NUMBER OF SEQ ID NOS: 59

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      aptamer motif sequence

<400> SEQUENCE: 1
gggttagggt tagggttagg g                                              21

<210> SEQ ID NO 2
<211> LENGTH: 29
<212> TYPE: RNA
<213> ORGANISM: Artificial Sequence
<220> FEATURE:
<223> OTHER INFORMATION: Description of Artificial Sequence: Synthetic
      aptamer motif sequence

<400> SEQUENCE: 2
aggcgaggug aaaugagcgg uaauagccu                                      29

<210> SEQ ID NO 3
<211> LENGTH: 95
<212> TYPE: RNA
<213> ORGANISM: Artificial Sequence
<220> FEATURE:
<223> OTHER INFORMATION: Description of Artificial Sequence: Synthetic
      aptamer motif sequence

<400> SEQUENCE: 3
gggagaggau acuacacgug auagucaggg aacaugacaa acacagggac uugcgaaaau    60
caguguuuug ccauugcaug uagcagaagc uuccg                               95

<210> SEQ ID NO 4
<211> LENGTH: 132
<212> TYPE: DNA
<213> ORGANISM: Artificial Sequence
<220> FEATURE:
<223> OTHER INFORMATION: Description of Artificial Sequence: Synthetic
      aptamer motif sequence

<400> SEQUENCE: 4
gggagaattc ccgcggcaga agcccacctg gctttgaact ctatgttatt gggtggggga    60
aacttaagaa aactaccacc cttcaacatt accgccttc agcctgccag cgccctgcag    120
cccgggaagc tt                                                       132

<210> SEQ ID NO 5
<211> LENGTH: 38
<212> TYPE: RNA
<213> ORGANISM: Artificial Sequence
<220> FEATURE:
```

```
<223> OTHER INFORMATION: Description of Artificial Sequence: Synthetic
      aptamer motif sequence

<400> SEQUENCE: 5
ggaucccgac uggcgagagc cagguaacga auggaucc                                38

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
      aptamer motif sequence

<400> SEQUENCE: 6
ccggccaagg gtgggaggga gggggccgg                                          29

<210> SEQ ID NO 7
<211> LENGTH: 61
<212> TYPE: RNA
<213> ORGANISM: Artificial Sequence
<220> FEATURE:
<223> OTHER INFORMATION: Description of Artificial Sequence: Synthetic
      aptamer motif sequence

<400> SEQUENCE: 7
auggcaccga ccauaggcuc ggguugccag agguuccaca cuuucaucga aaagccuaug        60
c                                                                        61

<210> SEQ ID NO 8
<211> LENGTH: 33
<212> TYPE: RNA
<213> ORGANISM: Artificial Sequence
<220> FEATURE:
<223> OTHER INFORMATION: Description of Artificial Sequence: Synthetic
      aptamer motif sequence

<400> SEQUENCE: 8
ggcgauacca gccgaaaggc ccuuggcagc guc                                     33

<210> SEQ ID NO 9
<211> LENGTH: 52
<212> TYPE: RNA
<213> ORGANISM: Artificial Sequence
<220> FEATURE:
<223> OTHER INFORMATION: Description of Artificial Sequence: Synthetic
      aptamer motif sequence

<400> SEQUENCE: 9
gauaggacga uuaucgaaaa ucaccagauu ggacccuggu uaacgaucca uu                52

<210> SEQ ID NO 10
<211> LENGTH: 39
<212> TYPE: DNA
<213> ORGANISM: Artificial Sequence
<220> FEATURE:
<223> OTHER INFORMATION: Description of Artificial Sequence: Synthetic
      aptamer motif sequence

<400> SEQUENCE: 10
gggagacaag gataaatcct tcaatgaagt gggtcgaca                               39

<210> SEQ ID NO 11
<211> LENGTH: 67
<212> TYPE: RNA
<213> ORGANISM: Artificial Sequence
<220> FEATURE:
```

<223> OTHER INFORMATION: Description of Artificial Sequence: Synthetic
      aptamer motif sequence

<400> SEQUENCE: 11
gggaauuccg cgugugcgcc gcggaagagg gaauauagag gccagcacau agugaggccc    60
uccuccc                                                              67

<210> SEQ ID NO 12
<211> LENGTH: 72
<212> TYPE: RNA
<213> ORGANISM: Artificial Sequence
<220> FEATURE:
<223> OTHER INFORMATION: Description of Artificial Sequence: Synthetic
      aptamer motif sequence

<400> SEQUENCE: 12
gggagcucag aauaaacgcu caaggaggac cgugcacucc ucgaacauuu cgagaugaga    60
cacggauccu gc                                                        72

<210> SEQ ID NO 13
<211> LENGTH: 44
<212> TYPE: RNA
<213> ORGANISM: Artificial Sequence
<220> FEATURE:
<223> OTHER INFORMATION: Description of Artificial Sequence: Synthetic
      aptamer motif sequence

<400> SEQUENCE: 13
gacgagaagg agugcugguu auacuagcgg uuaggucacu cguc                    44

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic
      aptamer motif sequence

<400> SEQUENCE: 14
acctggggga gtattgcgga ggaaggt                                        27

<210> SEQ ID NO 15
<211> LENGTH: 31
<212> TYPE: RNA
<213> ORGANISM: Artificial Sequence
<220> FEATURE:
<223> OTHER INFORMATION: Description of Artificial Sequence: Synthetic
      aptamer motif sequence

<400> SEQUENCE: 15
ggaagagaug gcgacuaaaa cgacuugucg c                                   31

<210> SEQ ID NO 16
<211> LENGTH: 39
<212> TYPE: RNA
<213> ORGANISM: Artificial Sequence
<220> FEATURE:
<223> OTHER INFORMATION: Description of Artificial Sequence: Synthetic
      aptamer motif sequence

<400> SEQUENCE: 16
ucuagcaguu cagguaacca cguaagauac gggucuaga                           39

<210> SEQ ID NO 17
<211> LENGTH: 84
<212> TYPE: RNA

-continued

```
<213> ORGANISM: Artificial Sequence
<220> FEATURE:
<223> OTHER INFORMATION: Description of Artificial Sequence: Synthetic
      aptamer motif sequence
<220> FEATURE:
<221> NAME/KEY: modified_base
<222> LOCATION: (44)..(44)
<223> OTHER INFORMATION: a, c, u, g, unknown or other
<220> FEATURE:
<221> NAME/KEY: modified_base
<222> LOCATION: (56)..(56)
<223> OTHER INFORMATION: a, c, u, g, unknown or other

<400> SEQUENCE: 17
gggagcucag aauaaacgcu caacccgaca gaucggcaac gccnuguuuu cgacangaga      60
caccgauccu gcaccaaagc uucc                                            84

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      aptamer motif sequence

<400> SEQUENCE: 18
acctggggga gtattgcgga ggaaggt                                         27

<210> SEQ ID NO 19
<211> LENGTH: 65
<212> TYPE: DNA
<213> ORGANISM: Artificial Sequence
<220> FEATURE:
<223> OTHER INFORMATION: Description of Artificial Sequence: Synthetic
      aptamer motif sequence

<400> SEQUENCE: 19
gcagtctcgt cgacacccag cagcgcatgt aactcccata catgtgtgtg ctggatccga     60
cgcag                                                                 65

<210> SEQ ID NO 20
<211> LENGTH: 52
<212> TYPE: RNA
<213> ORGANISM: Artificial Sequence
<220> FEATURE:
<223> OTHER INFORMATION: Description of Artificial Sequence: Synthetic
      aptamer motif sequence

<400> SEQUENCE: 20
gggcacgagc gaagggcaua agcugacgaa agucagacaa gacauggugc cc             52

<210> SEQ ID NO 21
<211> LENGTH: 49
<212> TYPE: RNA
<213> ORGANISM: Artificial Sequence
<220> FEATURE:
<223> OTHER INFORMATION: Description of Artificial Sequence: Synthetic
      aptamer motif sequence

<400> SEQUENCE: 21
ggaacccaac uaggcguuug aggggauucg gccacgguaa caaccccuc                 49

<210> SEQ ID NO 22
<211> LENGTH: 45
<212> TYPE: RNA
<213> ORGANISM: Artificial Sequence
<220> FEATURE:
<223> OTHER INFORMATION: Description of Artificial Sequence: Synthetic
``` aptamer motif sequence

<400> SEQUENCE: 22
gggcauaagg uauuuaauuc cauacaaguu uacaagaaag augca      45

<210> SEQ ID NO 23
<211> LENGTH: 37
<212> TYPE: DNA
<213> ORGANISM: Artificial Sequence
<220> FEATURE:
<223> OTHER INFORMATION: Description of Artificial Sequence: Synthetic
      aptamer motif sequence

<400> SEQUENCE: 23
taaactaaat gtggagggtg ggacgggaag aagttta      37

<210> SEQ ID NO 24
<211> LENGTH: 31
<212> TYPE: RNA
<213> ORGANISM: Artificial Sequence
<220> FEATURE:
<223> OTHER INFORMATION: Description of Artificial Sequence: Synthetic
      aptamer motif sequence

<400> SEQUENCE: 24
ccggugcgca uaaccaccuc agugcgagca a      31

<210> SEQ ID NO 25
<211> LENGTH: 108
<212> TYPE: RNA
<213> ORGANISM: Artificial Sequence
<220> FEATURE:
<223> OTHER INFORMATION: Description of Artificial Sequence: Synthetic
      aptamer motif sequence

<400> SEQUENCE: 25
gggagaauuc cgaccagaag cuuugguugu cuugacguu cacuguuacg auuguguuag      60
guuuaacuac acuuugcaau cgcauaugug cgucuacaug gauccuca      108

<210> SEQ ID NO 26
<211> LENGTH: 41
<212> TYPE: DNA
<213> ORGANISM: Artificial Sequence
<220> FEATURE:
<223> OTHER INFORMATION: Description of Artificial Sequence: Synthetic
      aptamer motif sequence

<400> SEQUENCE: 26
gcggggttgg gcgggtgggt tcgctgggca ggggcgagt g      41

<210> SEQ ID NO 27
<211> LENGTH: 40
<212> TYPE: RNA
<213> ORGANISM: Artificial Sequence
<220> FEATURE:
<223> OTHER INFORMATION: Description of Artificial Sequence: Synthetic
      aptamer motif sequence

<400> SEQUENCE: 27
uacagaaugg guuggauaggc auaccuaauc gagaaugaua      40

<210> SEQ ID NO 28
<211> LENGTH: 113
<212> TYPE: RNA
<213> ORGANISM: Artificial Sequence
<220> FEATURE:
<223> OTHER INFORMATION: Description of Artificial Sequence: Synthetic -continued aptamer motif sequence

<400> SEQUENCE: 28
ggagcucagc cuucacugca augggccgcu agguugaugu gcagugaagu cagcugaggc    60
ccagggcuga aaggaucgcc cuccucgacu cguggcacca cggucggauc cac           113

<210> SEQ ID NO 29
<211> LENGTH: 45
<212> TYPE: RNA
<213> ORGANISM: Artificial Sequence
<220> FEATURE:
<223> OTHER INFORMATION: Description of Artificial Sequence: Synthetic
      aptamer motif sequence

<400> SEQUENCE: 29
ggaucgcauu uggacuucug cccagggggc accacggucg gaucc                     45

<210> SEQ ID NO 30
<211> LENGTH: 60
<212> TYPE: RNA
<213> ORGANISM: Artificial Sequence
<220> FEATURE:
<223> OTHER INFORMATION: Description of Artificial Sequence: Synthetic
      aptamer motif sequence

<400> SEQUENCE: 30
ggccuaaaac auaccagauu ucgaucugga gaggugaaga auucgaccac cuaggccggu    60

<210> SEQ ID NO 31
<211> LENGTH: 46
<212> TYPE: DNA
<213> ORGANISM: Artificial Sequence
<220> FEATURE:
<223> OTHER INFORMATION: Description of Artificial Sequence: Synthetic
      aptamer motif sequence

<400> SEQUENCE: 31
acgtgaatga tagacgtatg tcgagttgct gtgtgcggat gaacgt                    46

<210> SEQ ID NO 32
<211> LENGTH: 107
<212> TYPE: RNA
<213> ORGANISM: Artificial Sequence
<220> FEATURE:
<223> OTHER INFORMATION: Description of Artificial Sequence: Synthetic
      aptamer motif sequence

<400> SEQUENCE: 32
gggagcugag aauaaacgcu caagggcaac gcgggcaccc cgacaggugc aaaaacgcac    60
cgacgcccgg ccgaagaagg ggauucgaca ugaggcccgg auccggc                  107

<210> SEQ ID NO 33
<211> LENGTH: 24
<212> TYPE: RNA
<213> ORGANISM: Human immunodeficiency virus

<400> SEQUENCE: 33
uccguuuuca gucgggaaaa acug                                            24

<210> SEQ ID NO 34
<211> LENGTH: 15
<212> TYPE: DNA
<213> ORGANISM: Homo sapiens

<400> SEQUENCE: 34

```
ggttggtgtg gttgg                                                      15

<210> SEQ ID NO 35
<211> LENGTH: 23
<212> TYPE: RNA
<213> ORGANISM: Unknown
<220> FEATURE:
<223> OTHER INFORMATION: Description of Unknown: VEGF motif sequence

<400> SEQUENCE: 35
gcgguaggaa gaauuggaag cgc                                             23

<210> SEQ ID NO 36
<211> LENGTH: 98
<212> TYPE: RNA
<213> ORGANISM: Unknown
<220> FEATURE:
<223> OTHER INFORMATION: Description of Unknown: NF-kB sequence

<400> SEQUENCE: 36
gggauauccu cgagacauaa gaaacaagau agauccugaa acuguuuuaa gguuggccga     60
ucuucugcuc gagaaugcau gaagcguucc auauuuuu                             98

<210> SEQ ID NO 37
<211> LENGTH: 37
<212> TYPE: DNA
<213> ORGANISM: Homo sapiens

<400> SEQUENCE: 37
ggggcacgtt tatccgtccc tcctagtggc gtgcccc                              37

<210> SEQ ID NO 38
<211> LENGTH: 44
<212> TYPE: RNA
<213> ORGANISM: Unknown
<220> FEATURE:
<223> OTHER INFORMATION: Description of Unknown: Elongation factor Tu
      sequence

<400> SEQUENCE: 38
ggggcuauug ugacucagcg guucgacccc gcuuagcucc acca                      44

<210> SEQ ID NO 39
<211> LENGTH: 39
<212> TYPE: RNA
<213> ORGANISM: Homo sapiens

<400> SEQUENCE: 39
ugacguccuu agaauugcgc auuccucaca caggaucuu                            39

<210> SEQ ID NO 40
<211> LENGTH: 96
<212> TYPE: DNA
<213> ORGANISM: Unknown
<220> FEATURE:
<223> OTHER INFORMATION: Description of Unknown: YPEN-1 endothelial
      sequence

<400> SEQUENCE: 40
ataccagctt attcaattag gcggtgcatt gtggttggta gtatacatga ggtttggttg     60
agactagtcg caagatatag atagtaagtg caatct                               96

<210> SEQ ID NO 41

<400> SEQUENCE: 41
```

000

<210> SEQ ID NO 42
<211> LENGTH: 28
<212> TYPE: RNA
<213> ORGANISM: Rous sarcoma virus

<400> SEQUENCE: 42
aggacccucg agggagguug cgcagggu                                28

<210> SEQ ID NO 43
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
tcacagatga gt                                                 12

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
tcacagatga gtaaaaaaaa aaaa                                    24

<210> SEQ ID NO 45
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
cccaggttct ct                                                 12

<210> SEQ ID NO 46
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
actcatctgt gaagagaacc tgggggagta ttgcggagga aggt              44

<210> SEQ ID NO 47
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
actcatctgt gaagaga                                            17

<210> SEQ ID NO 48

```
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48 acctggg                                                                   7

<210> SEQ ID NO 49
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49 tggaccc                                                                   7

<210> SEQ ID NO 50
<211> LENGTH: 44
<212> TYPE: DNA
<213> ORGANISM: Artificial Sequence
<220> FEATURE:
<223> OTHER INFORMATION: Description of Artificial Sequence: Synthetic
      linker sequence

<400> SEQUENCE: 50
actcatctgt gaagatgacc tgggggagta ttgcggagga aggt                          44

<210> SEQ ID NO 51
<211> LENGTH: 44
<212> TYPE: DNA
<213> ORGANISM: Artificial Sequence
<220> FEATURE:
<223> OTHER INFORMATION: Description of Artificial Sequence: Synthetic
      linker sequence

<400> SEQUENCE: 51
actcatctgt gaagagaacc tgggggagta ttgcggagga aggt                          44

<210> SEQ ID NO 52
<211> LENGTH: 38
<212> TYPE: DNA
<213> ORGANISM: Artificial Sequence
<220> FEATURE:
<223> OTHER INFORMATION: Description of Artificial Sequence: Synthetic
      potassium linker sequence

<400> SEQUENCE: 52
actcatctgt gatctaaggg ttagggttag ggttaggg                                 38

<210> SEQ ID NO 53
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
aacccttaga                                                               10

<210> SEQ ID NO 54
<211> LENGTH: 56
<212> TYPE: DNA
```

```
<213> ORGANISM: Artificial Sequence
<220> FEATURE:
<223> OTHER INFORMATION: Description of Artificial Sequence: Synthetic
      cocaine linker sequence

<400> SEQUENCE: 54
actcatctgt gaatctcggg agacaaggat aaatccttca atgaagtggg tctccc        56

<210> SEQ ID NO 55
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
gtctcccgag a                                                          11

<210> SEQ ID NO 56
<211> LENGTH: 39
<212> TYPE: DNA
<213> ORGANISM: Artificial Sequence
<220> FEATURE:
<223> OTHER INFORMATION: Description of Artificial Sequence: Synthetic
      aptamer oligonucleotide

<400> SEQUENCE: 56
gggagacaag gataaatcct tcaatgaagt gggtctccc                            39

<210> SEQ ID NO 57
<211> LENGTH: 27
<212> TYPE: DNA
<213> ORGANISM: Artificial Sequence
<220> FEATURE:
<223> OTHER INFORMATION: Description of Artificial Sequence: Synthetic
      aptamer oligonucleotide

<400> SEQUENCE: 57
acctggggga gtattgcgga ggaaggt                                         27

<210> SEQ ID NO 58
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
gtctcccgag at                                                         12

<210> SEQ ID NO 59
<211> LENGTH: 39
<212> TYPE: DNA
<213> ORGANISM: Artificial Sequence
<220> FEATURE:
<223> OTHER INFORMATION: Description of Artificial Sequence: Synthetic
      aptamer oligonucleotide

<400> SEQUENCE: 59
gggagacaag gataaatcct tcaatgaagt gggtctccc                            39
```

APTAMER-BASED COLORIMETRIC SENSOR SYSTEMS

CROSS REFERENCE TO RELATED APPLICATION

This application is a continuation application of U.S. patent application Ser. No. 11/202,380, filed Aug. 11, 2005, now U.S. Pat. No. 7,892,734 entitled "APTAMER-BASED COLORIMETRIC SENSOR SYSTEMS."

FEDERALLY SPONSORED RESEARCH OR DEVELOPMENT

This subject matter of this application may have been funded in part under the following research grants and contracts: National Science Foundation Contract Numbers CTS-0120978 and DMR-0117792. The U.S. Government may have rights in this invention.

SEQUENCE LISTING

The instant application contains a Sequence Listing which has been submitted in ASCII format via EFS-Web and is hereby incorporated by reference in its entirety. Said ASCII copy, created on May 26, 2011, is named ILL76CON.txt and is 14,947 bytes in size.

BACKGROUND

The ability to determine the presence of an analyte in a sample is of significant benefit. For example, many metals and metal ions, such as lead, mercury, cadmium, chromium, and arsenic, pose significant health risks when present in drinking water supplies. To prevent the contamination of drinking and other water supplies, it is common to test industrial waste-streams before their release to the water treatment plant. Biological fluids, such as blood and those originating from body tissues, also may be tested for a variety of analytes to determine if the body has been exposed to harmful agents or if a disease state exists. For example, the need to detect trace amounts of anthrax in a variety of samples has recently emerged.

Colorimetric methods are commonly used for the detection of metals and ions in soil, water, waste-streams, biological samples, body fluids, and the like. In relation to instrument based methods of analysis, such as atomic absorption spectroscopy, colorimetric methods tend to be rapid and require little in the way of equipment or user sophistication. For example, colorimetric tests are available to aquarists that turn darker shades of pink when added to aqueous samples containing increasing concentrations of the nitrate ($NO_3^-$) ion. In this manner, colorimetric tests show that the analyte of interest, such as nitrate, is present in the sample and also may provide an indicator of the amount of analyte in the sample through the specific hue of color generated. While conventional colorimetric tests are extremely useful, they only exist for a limited set of analytes, and often cannot detect very small or trace amounts of the analyte.

As can be seen from the above description, there is an ongoing need for colorimetric sensor systems that can identify trace amounts of a broader scope of analytes and that increase the reliability of the analysis.

SUMMARY

A sensor system for detecting an analyte includes a linker comprising an aptamer that folds in response to the analyte and second particles coupled to a second oligonucleotide that is complementary to at least a portion of the aptamer. The linker may include an extension where a first oligonucleotide coupled to first particles is complementary to at least a portion of the extension.

A method of detecting an analyte includes combining an aggregate with a sample to detect a color change responsive to the analyte. The aggregate may include a linker and second particles. The aggregate also may include first particles and the linker may include an extension.

A kit for detecting an analyte includes a first container containing a system for forming aggregates that includes second particles and a linker including an aptamer, which folds in response to the analyte. The second particles are coupled to second oligonucleotides that are complementary to at least a portion of the aptamer.

A method for determining the sensitivity and selectivity of an aptamer to an analyte includes combining an aggregate with the analyte, detecting a color change responsive to the analyte, and determining if the DNA strand folded to provide the color change. The aggregate includes second particles and a linker including a DNA strand. The aggregate also may include first particles. The linker may include an extension.

In order to provide a clear and consistent understanding of the specification and claims, the following definitions are provided.

The term "sample" is defined as a composition that will be subjected to analysis that is suspected of containing the analyte of interest. Typically, a sample for analysis is in a liquid form, and preferably the sample is an aqueous mixture. A sample may be from any source, such as an industrial sample from a waste-stream or a biological sample, such as blood, urine, or saliva. A sample may be a derivative of an industrial or biological sample, such as an extract, a dilution, a filtrate, or a reconstituted precipitate.

The term "analyte" is defined as one or more substance potentially present in the sample. The analysis determines the presence, quantity, or concentration of the analyte present in the sample.

The term "colorimetric" is defined as an analysis where the reagent or reagents constituting the sensor system produce a color change in the presence or absence of an analyte.

The term "light-up" refers to a colorimetric sensor system that undergoes a desired color change in response to an analyte present in a sample.

The term "light-down" refers to a colorimetric sensor system that does not undergo a color change when an analyte is present in a sample, but does undergo a desired color change in the absence of the analyte.

The term "sensitivity" refers to the smallest increase in an analyte concentration that is detectable by the sensor system (resolution) or to the lowest concentration limit at which a sensor system can differentiate a signal responsive to the analyte from a background signal (detection limit). Thus, the more sensitive a sensor system is to an analyte, the better the system is at detecting lower concentrations of the analyte.

The term "selectivity" refers to the ability of the sensor system to detect a desired analyte in the presence of other species.

The term "hybridization" refers to the ability of a first polynucleotide to form at least one hydrogen bond with at least one second nucleotide under low stringency conditions.

The term "aptamer" refers to a strand of nucleic acids that undergoes a conformational change in response to an analyte.

The term "conformational change" refers to the process by which an aptamer adopts a tertiary structure from another state. For simplicity, the term "fold" may be substituted for conformational change.

BRIEF DESCRIPTION OF THE DRAWINGS

The invention can be better understood with reference to the following drawings and description. The components in the figures are not necessarily to scale and are not intended to accurately represent molecules or their interactions, emphasis instead being placed upon illustrating the principles of the invention.

FIG. 3B represents the tail-to-tail hybridization of oligonucleotide functionalized particles with a linker.

FIG. 3C represents the head-to-tail hybridization of oligonucleotide functionalized particles with a linker.

FIG. 3D represents the head-to-head hybridization of oligonucleotide functionalized particles with a linker.

FIG. 5C is a graph depicting the extinction ratios for multiple adenosine concentrations over a 6 minute time period.

FIG. 8B is a graph depicting the correlation between the observed extinction ratios for the color change of the sensor system and the concentration of the cocaine analyte after 1 minute of aggregation.

DETAILED DESCRIPTION

Aptamers may be easier to isolate than nucleic acid based catalysts. The simpler structure of aptamers in relation to nucleic acid enzymes also may allow for the design of analyte sensor systems for which nucleic acid enzymes are not available. The present invention makes use of the discovery that by selecting the hybridization strength between the folded and unfolded conformations of an aptamer and an oligonucleotide functionalized particle, the particle may be released in response to an analyte. In this manner, a light-up colorimetric sensor is provided that undergoes a desired color change in response to a selected analyte at room temperature, thus overcoming a disadvantage of the sensor system disclosed in U.S. Ser. No. 10/144,679.

Figure 1:
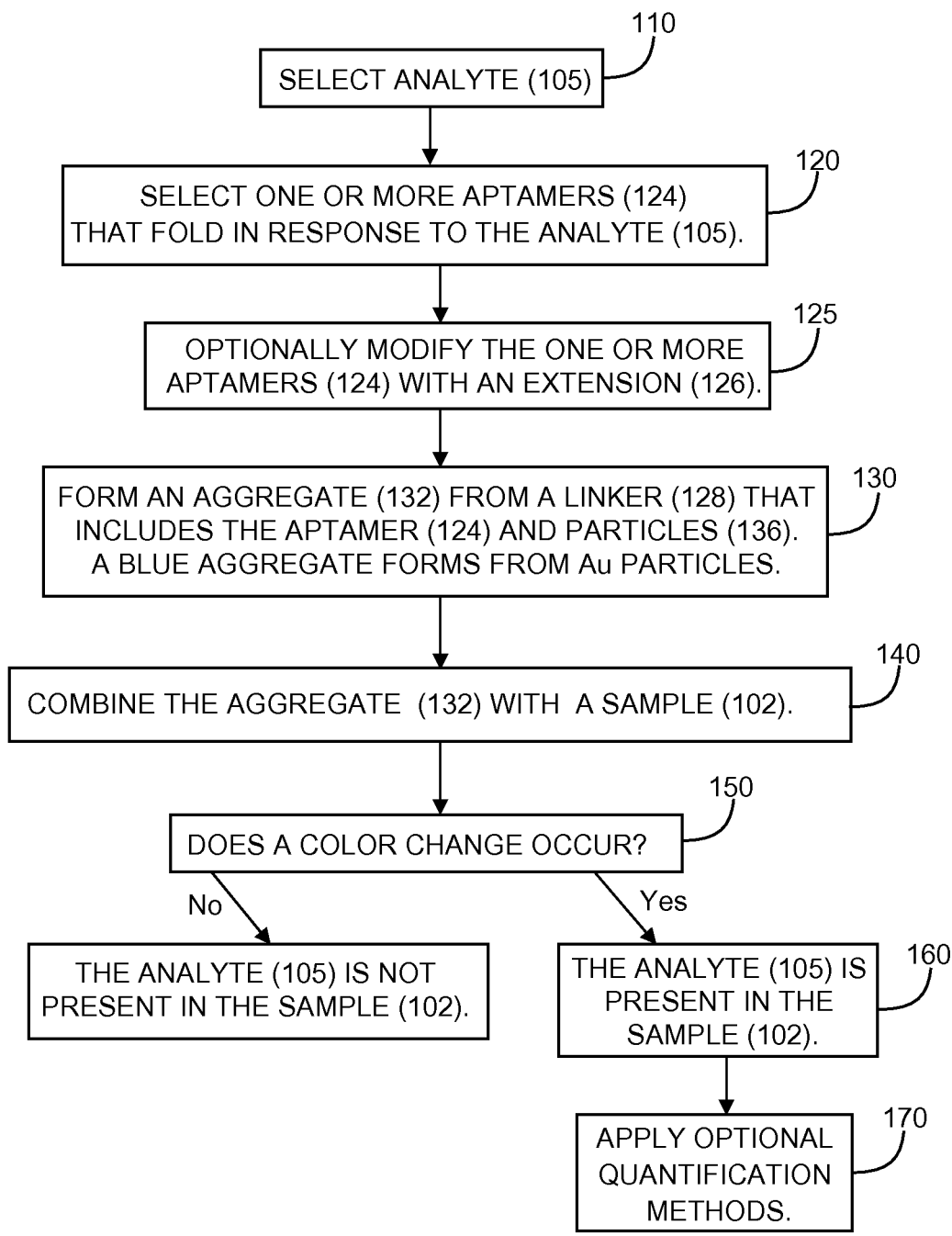
FIG. 1 represents a colorimetric analysis for determining the presence and optionally the concentration of an analyte in a sample.

FIG. 1 represents a colorimetric analysis 100 for determining the presence and optionally the concentration of an analyte 105 in a sample 102. In 110, the analyte 105 for which the method 100 will determine the presence/concentration of is selected.

In one aspect, the analyte 105 may be any ion that causes an aptamer 124 to fold. In another aspect, the analyte 105 may be any metal ion that causes an aptamer 124 to fold. Preferable monovalent ions having a $^{+}1$ formal oxidation state (I) include $NH_4^+$, K(I), Li(I), Tl(I), and Ag(I). Preferable divalent metal ions having a $^{+}2$ formal oxidation state (II) include Mg(II), Ca(II), Mn(II), Co(II), Ni(II), Zn(II), Cd(II), Cu(II), Pb(II), Hg(II), Pt(II), Ra(II), Sr(II), Ni(II), and Ba(II). Preferable trivalent and higher metal ions having $^{+}3$ (III), $^{+}4$ (IV), $^{+}5$ (V), or $^{+}6$ (VI) formal oxidation states include Co(III), Cr(III), Ce(IV), As(V), U(VI), Cr(VI), and lanthanide ions. More preferred analyte ions include monovalent metal ions and metal ions that are toxic to living organisms, such as Ag(I), Pb(II), Hg(II), U(VI), and Cr(VI).

In another aspect, the analyte 105 may be any biomolecule that causes the aptamer 124 to fold. Preferable biomolecules include large biomolecules, such as proteins (e.g. proteins related to HIV, hCG-hormone, insulin), antibodies, growth factors, enzymes, virus (e.g. HIV, small pox), viral derived components (e.g. HIV-derived molecules), bacteria (e.g. anthrax), bacteria derived molecules and components (e.g. anthrax derived molecules), or cells. Preferable biomolecules also may include small biomolecules, such as amino acids (e.g. arginine), nucleotides (e.g. ATP, GTP), neurotransmitters (e.g. dopamine), cofactors (e.g. biotin), peptides, or amino-glycosides.

In another aspect, the analyte 105 may be any organic molecule that causes the aptamer 124 to fold. Preferable organic molecules include drugs, such as antibiotics and theophylline, or controlled substances, such as cocaine, dyes, oligosaccharides, polysaccharides, glucose, nitrogen fertilizers, pesticides, dioxins, phenols, 2,4-dichlorophenoxyacetic acid, nerve gases, trinitrotoluene (TNT), or dinitrotoluene (DNT).

Once the analyte 105 is selected, the one or more aptamer 124 is selected that folds in response to the analyte 105. The aptamer selection 120 may be performed by in vitro selection, directed evolution, or other method known to those of ordinary skill in the art. The aptamer selection 120 may provide one or more aptamers that demonstrate enhanced folding in the presence of the selected analyte 105 (thereby providing sensor sensitivity). The selection 120 also may exclude aptamers that fold in the presence of selected analytes, but that do not fold in the presence of non-selected analytes and/or other species present in the sample 102 (thereby providing sensor selectivity).

For example, an aptamer may be selected that specifically binds K(I), while not significantly binding Na(I), Li(I), Cs(I), Rb(I), or other competing metal ions. In one aspect, this may be achieved by isolating aptamers that bind K(I), then removing any aptamers that bind Na(I), Li(I), Cs(I), or Rb(I). In another aspect, aptamers that bind Na(I), Li(I), Cs(I), or Rb(I) are first discarded and then those that bind K(I) are isolated. In this manner, the selectivity of the aptamer may be increased.

The aptamer 124 includes a nucleic acid strand that folds in the presence of the analyte 105. In one aspect, the folding may be considered the conversion of a primary or duplex structure to a tertiary structure. The base sequence of the aptamer may be designed so that the aptamer may undergo at least partial hybridization with at least one oligonucleotide functionalized particle. In this aspect, at least a portion of the base sequence of the aptamer 124 may be complementary to at least one oligonucleotide of the oligonucleotide functionalized particle.

The aptamer 124 may be formed from deoxyribonucleotides, which may be natural, unnatural, or modified nucleic acids. Peptide nucleic acids (PNAs), which include a polyamide backbone and nucleoside bases (available from Biosearch, Inc., Bedford, Mass., for example), also may be useful.

Table I below lists analytes, the aptamer or aptamers that bind with and fold in response to that analyte, and the reference or references where the sequence of each aptamer is described. The analyte binding region of these, and other, aptamers may be adapted for use in a linker 128. For example, the non-analyte binding region of the cocaine aptamer, given as SEQ ID NO: 10 in Table I below, may be modified to provide the aptamer GGGAGACAAGGATAAATCCT-TCAATGAAGTGGGTCTCCC (SEQ ID NO: 56) and included in the linker 128.

TABLE I

| Analyte class | Example | Aptamer Motif Sequence (SEQ ID NO:) | Ref |
|---|---|---|---|
| Metal ions | K(I) | GGGTTAGGGTTAGGGTTAGGG (SEQ ID NO: 1) | 1 |
| | Zn(II) | AGGCGAGGUGAAAUGAGCGGUAAUAGCCU (SEQ ID NO: 2) | 2 |
| | Ni(II) | GGGAGAGGAUACUACACGUGAUAGUCAGGGAAC AUGACAAACACAGGGACUUGCGAAAAUCAGUGU UUUGCCAUUGCAUGUAGCAG AAGCUUCCG (SEQ ID NO: 3) | 3 |
| Organic dyes | Cibacron blue | GGGAGAATTCCCGCGGCAGAAGCCCACCTGGCT TTGAACTCTATGTTATTGGGTGGGGGAAACTTA AGAAAACTACCACCCTTCAACATTACCGCCCTT CAGCCTGCCAGCGCCCTGCAGCCCGGGAAGCTT (SEQ ID NO: 4) | 4 |
| | Malachite green | GGAUCCCGACUGGCGAGAGCCAGGUA ACGAAU GGAUCC (SEQ ID NO: 5) | 5 |
| | Sulforhodamine B | CCGGCCAAGGGTGGGAGGGAGGGGGCCGG (SEQ ID NO: 6) | 6 |
| Small organic molecules | Biotin | AUGGCACCGACCAUAGGCUCGGGUUGCCAGAGG UUCCACACUUUCAUCGAAAAGCCUAUGC (SEQ ID NO: 7) | 7 |
| | Theophylline | GGCGAUACCAGCCGAAAGGCCCUUGGCAGCGUC (SEQ ID NO: 8) | 8 |
| | Adenine | GAUAGGACGAUUAUCGAAAAUCACCAGAUUGGA CCCUGGUUAACGAUCCAUU (SEQ ID NO: 9) | 9 |
| | Cocaine | GGGAGACAAGGATAAATCCTTCAATGAAGTGGG TCGACA (SEQ ID NO: 10) | 10 |
| | Dopamine | GGGAAUUCCGCGUGUGCGCCGCGGAAGAGGGAA UAUAGAGGCCAGCACAUAGUGAGGCCCUCCUCC C (SEQ ID NO: 11) | 11 |
| Amino acids | Arginine | GGGAGCUCAGAAUAAACGCUCAAGGAGGACCGU GCACUCCUCGAACAUUUCGAGAUGAGACACGGA UCCUGC (SEQ ID NO: 12) | 12 |
| | Citrulline | GACGAGAAGGAGUGCUGGUUAUACUAGCGGUUA GGUCACUCGUC (SEQ ID NO: 13) | 13 |
| Nucleosides & nucleotides | ATP | ACCTGGGGGAGTATTGCGGAGGAAGGT (SEQ ID NO: 14) | 14 |
| | cAMP | GGAAGAGAUGGCGACUAAAACGACUUGUCGC (SEQ ID NO: 15) | 15 |
| | GTP | UCUAGCAGUUCAGGUAACCACGUAAGAUACGGG UCUAGA (SEQ ID NO: 16) | 16 |
| | Guanosine | GGGAGCUCAGAAUAAACGCUCAACCCGACAGAU CGGCAACGCCNUGUUUUCGACANGAGACACCGA UCCUGCACCAAAGCUUCC (SEQ ID NO: 17) | 17 |

TABLE I-continued

| Analyte class | Example | Aptamer Motif Sequence (SEQ ID NO:) | Ref |
|---|---|---|---|
| | Adenosine | ACCTGGGGGAGTATTGCGGAGGAAGGT (SEQ ID NO: 18) | 18 |
| RNA | TAR-RNA | GCAGTCTCGTCGACACCCAGCAGCGCATGTAAC TCCCATACATGTGTGTGCTGGATCCGACGCAG (SEQ ID NO: 19) | 19 |
| Biological cofactors | CoA | GGGCACGAGCGAAGGGCAUAAGCUGACGAAAGU CAGACAAGACAUGGUGCCC (SEQ ID NO: 20) | 20 |
| | NMN | GGAACCCAACUAGGCGUUUGAGGGGAUUCGGCC ACGGUAACAACCCCUC (SEQ ID NO: 21) | 21 |
| | FAD | GGGCAUAAGGUAUUUAAUUCCAUACAAGUUUAC AAGAAAGAUGCA (SEQ ID NO: 22) | 22 |
| | Porphyrin | TAAACTAAATGTGGAGGGTGGGACGGGAAGAAG TTTA (SEQ ID NO: 23) | 23 |
| | Vitamin B12 | CCGGUGCGCAUAACCACCUCAGUGCGAGCAA (SEQ ID NO: 24) | 24 |
| Amino-glycosides | Tobramycin | GGGAGAAUUCCGACCAGAAGCUUUGGUUGUCUU GUACGUUCACUGUUACGAUUGUGUUAGGUUUAA CUACACUUUGCAAUCGCAUAUGUGCGUCUACAU GGAUCCUCA (SEQ ID NO: 25) | 25 |
| Oligo-saccharides | Cellobiose | GCGGGGTTGGGCGGGTGGGTTCGCTGGGCAGGG GGCGAGTG (SEQ ID NO: 26) | 26 |
| Poly-saccharides | Sephadex | UACAGAAUGGGUUGGUAGGCAUACCUAAUCGAG AAUGAUA (SEQ ID NO: 27) | 27 |
| Antibiotics | Viomycin | GGAGCUCAGCCUUCACUGCAAUGGGCCGCUAGG UUGAUGUGCAGUGAAGUCAGCUGAGGCCCAGGG CUGAAAGGAUCGCCCUCCUCGACUCGUGGCACC ACGGUCGGAUCCAC (SEQ ID NO: 28) | 28 |
| | Streptomycin | GGAUCGCAUUUGGACUUCUGCCCAGGGGGCACC ACGGUCGGAUCC (SEQ ID NO: 29) | 29 |
| | Tetracycline | GGCCUAAAACAUACCAGAUUUCGAUCUGGAGAG GUGAAGAAUUCGACCACCUAGGCCGGU (SEQ ID NO: 30) | 30 |
| | Vasopressin | ACGTGAATGATAGACTATGTCGAGTTGCTGTG TGCGGATGAACGT (SEQ ID NO: 31) | 31 |
| Peptides | Substance P | GGGAGCUGAGAAUAAACGCUCAAGGGCAACGCG GCACCCCGACAGGUGCAAAAACGCACCGACGC CCGGCCGAAGAAGGGGAUUCGACAUGAGGCCCG GAUCCGGC (SEQ ID NO: 32) | 32 |
| Enzymes | HIV Rev Transscriptase | UCCGUUUUCAGUCGGGAAAAACUG (SEQ ID NO: 33) | 33 |
| | Human thrombin | GGTTGGTGTGGTTGG (SEQ ID NO: 34) | 34 |
| Growth factors | VEGF$_{165}$ | GCGGUAGGAAGAAUUGGAAGCGC (SEQ ID NO: 35) | 35 |
| Transcription factors | NF-KB | GGGAUAUCCUCGAGACAUAAGAAACAAGAUAGA UCCUGAAACUGUUUUAAGGUUGGCCGAUCUUCU GCUCGAGAAUGCAUGAAGCGUUCCAUAUUUUU (SEQ ID NO: 36) | 36 |
| Antibodies | Human IgE | GGGGCACGTTTATCCGTCCCTCCTAGTGGCGTG CCCC (SEQ ID NO: 37) | 37 |
| Gene Regulatory factors | Elongation factor Tu | GGGGCUAUUGUGACUCAGCGGUUCGACCCCGCU UAGCUCCACCA (SEQ ID NO: 38) | 38 |

TABLE I-continued

| Analyte class | Example | Aptamer Motif Sequence (SEQ ID NO:) | Ref |
|---|---|---|---|
| Cell adhesion molecules | Human CD4 | UGACGUCCUUAGAAUUGCGCAUUCCUCAC ACAGGAUCUU (SEQ ID NO: 39) | 39 |
| cells | YPEN-1 endothelial | ATACCAGCTTATTCAATTAGGCGGTGCATTGTG GTTGGTAGTATACATGAGGTTTGGTTGAGACTA GTCGCAAGATATAGATAGTAAGTGCAATCT (SEQ ID NO: 40) | 40 |
| Viral/bacterial components | Anthrax spores | Sequences are not given | 41 |
| | Rous sarcoma virus | AGGACCCUCGAGGGAGGUUGCGCAGGGU (SEQ ID NO: 42) | 42 |

Reference Listing for Table I

1. Ueyama, H., Takagi, M. & Takenaka, S. A novel potassium sensing in aqueous media with a synthetic oligonucleotide derivative. fluorescence resonance energy transfer associated with guanine quartet-potassium ion complex formation. *J. Am. Chem.* Soc. 124, 14286-14287 (2002).
2. Ciesiolka, J. & Yarus, M. Small RNA-divalent domains. *RNA* 2, 785-793 (1996)
3. Hofmann, H. P., Limmer, S., Hornung, V. & Sprinzl, M. Ni2+-binding RNA motifs with an asymmetric purine-rich internal loop and a G-A base pair. *RNA* 3, 1289-300. (1997).
4. Ellington, A. D. & Szostak, J. W. In vitro selection of RNA molecules that bind specific ligands. *Nature (London)* 346, 818-22 (1990).
5. Grate, D. & Wilson, C. Laser-mediated, site-specific inactivation of RNA transcripts. *Proc. Natl. Acad. Sci. U.S.A.* 96, 6131-6136 (1999).
6. Wilson, C. & Szostak, J. W. Isolation of a fluorophore-specific DNA aptamer with weak redox activity. *Chemistry & Biology* 5, 609-617 (1998).
7. Wilson, C., Nix, J. & Szostak, J. Functional Requirements for Specific Ligand Recognition by a Biotin-Binding RNA Pseudoknot. *Biochemistry* 37, 14410-14419 (1998).
8. Zimmermann, G. R., Wick, C. L., Shields, T. P., Jenison, R. D. & Pardi, A. Molecular interactions and metal binding in the theophylline-binding core of an RNA aptamer. *Rna* 6, 659-667 (2000).
9. Meli, M., Vergne, J., Decout, J.-L. & Maurel, M.-C. Adenine-aptamer complexes. A bipartite RNA site that binds the adenine nucleic base. *J. Biol. Chem.* 277, 2104-2111 (2002).
10. Stojanovic, M. N.; Landry, D. W., Aptamer-Based Colorimetric Probe for Cocaine; J. Am. Chem. Soc.; 124(33); 9678-9679 (2002).
11. Mannironi, C., Di Nardo, A., Fruscoloni, P. & Tocchini-Valentini, G. P. In vitro selection of dopamine RNA ligands. *Biochemistry* 36, 9726-9734 (1997).
12. Connell, G. J., Illangesekare, M. & Yarus, M. Three small ribooligonucleotides with specific arginine sites. *Biochemistry* 32, 5497-502 (1993).
13. Famulok, M. Molecular Recognition of Amino Acids by RNA-Aptamers: An L-Citrulline Binding RNA Motif and Its Evolution into an L-Arginine Binder. *J. Am. Chem. Soc.* 116, 1698-706 (1994).
14. Sassanfar, M. & Szostak, J. W. An RNA motif that binds ATP. *Nature (London)* 364, 550-3 (1993).
15. Koizumi, M. & Breaker, R. R. Molecular Recognition of cAMP by an RNA Aptamer. *Biochemistry* 39, 8983-8992 (2000).
16. Davis, J. H. & Szostak, J. W. Isolation of high-affinity GTP aptamers from partially structured RNA libraries. *Proc. Natl. Acad. Sci. U.S.A.* 99, 11616-11621 (2002).
17. Connell, G. J. & Yarus, M. RNAs with dual specificity and dual RNAs with similar specificity. *Science (Washington, D. C.)* 264, 1137-41 (1994).
18. Huizenga D. E. and Szostak J. W., A DNA aptamer that binds adenosine and ATP. *Biochemistry*, 34, 656-65 (1995).
19. Boiziau, C., Dausse, E., Yurchenko, L. & Toulme, J.-J. DNA aptamers selected against the HIV-1 trans-activation-responsive RNA element form RNA-DNA kissing complexes. *J. Biol. Chem.* 274, 12730-12737 (1999).
20. Burke, D. & Hoffman, D. A Novel Acidophilic RNA Motif That Recognizes Coenzyme A. *Biochemistry* 37, 4653-4663 (1998).
21. Lauhon, C. T. & Szostak, J. W. RNA aptamers that bind flavin and nicotinamide redox cofactors. *J. Am. Chem.* Soc. 117, 1246-57 (1995).
22. Roychowdhury-Saha, M., Lato, S. M., Shank, E. D. & Burke, D. H. Flavin Recognition by an RNA Aptamer Targeted toward FAD. *Biochemistry* 41, 2492-2499 (2002).
23. Chinnapen, D. J. F. & Sen, D. Hemin-Stimulated Docking of Cytochrome c to a Hemin-DNA Aptamer Complex. *Biochemistry* 41, 5202-5212 (2002).

Reference Listing for Table I

24. Lorsch, J. R. & Szostak, J. W. In vitro selection of RNA aptamers specific for cyanocobalamin. *Biochemistry* 33, 973-82 (1994).
25. Wang, Y., Killian, J., Hamasaki, K. & Rando, R. R. RNA Molecules That Specifically and Stoichiometrically Bind Aminoglycoside Antibiotics with High Affinities. *Biochemistry* 35, 12338-12346 (1996).
26. Yang, Q., Goldstein, I. J., Mei, H.-Y. & Engelke, D. R. DNA ligands that bind tightly and selectively to cellobiose. *Proc. Natl. Acad. Sci. U.S.A.* 95, 5462-5467 (1998).
27. Srisawat, C., Goldstein, I. J. & Engelke, D. R. Sephadex-binding RNA ligands: rapid affinity purification of RNA from complex RNA mixtures. *Nucleic Acids Res.* 29, E4/1-E4/5 (2001).
28. Wallis, M. G. et al. In vitro selection of a viomycin-binding RNA pseudoknot. *Chem. Biol.* 4, 357-366 (1997).
29. Wallace, S. T. & Schroeder, R. In vitro selection and characterization of streptomycin-binding RNAs: recognition discrimination between antibiotics. *Rna* 4, 112-123 (1998).
30. Berens, C., Thain, A. & Schroeder, R. A tetracycline-binding RNA aptamer. *Bioorganic & Medicinal Chemistry* 9, 2549-2556 (2001).
31. Williams, K. P. et al. Bioactive and nuclease-resistant L-DNA ligand of vasopressin. *Proc. Natl. Acad. Sci. U.S.A.* 94, 11285-11290 (1997).
32. Nieuwlandt, D., Wecker, M. & Gold, L. In Vitro Selection of RNA Ligands to Substance P. *Biochemistry* 34, 5651-9 (1995).
33. Tuerk, C., MacDougal, S. & Gold, L. RNA pseudoknots that inhibit human immunodeficiency virus type 1 reverse transcriptase. *Proc. Natl. Acad. Sci. U.S.A.* 89, 6988-92 (1992).
34. Bock, L. C., Griffin, L. C., Latham, J. A., Vermaas, E. H. & Toole, J. J. Selection of single-stranded DNA molecules that bind and inhibit human thrombin. *Nature (London)* 355, 564-6 (1992).
35. Ruckman, J. et al. 2'-Fluoropyrimidine RNA-based aptamers to the 165-amino acid form of vascular endothelial growth factor (VEGF165). Inhibition of receptor binding and VEGF-induced vascular permeability through interactions requiring the exon 7-encoded domain. *J. Biol. Chem.* 273, 20556-20567 (1998).
36. Lebruska, L. L. & Maher, L. J., III. Selection and Characterization of an RNA Decoy for Transcription Factor NF-kB. *Biochemistry* 38, 3168-3174 (1999).
37. Wiegand, T. W. et al. High-affinity oligonucleotide ligands to human IgE inhibit binding to Fc epsilon receptor I. *J. Immunol.* 157, 221-30 (1996).
38. Nazarenko, I. A. & Uhlenbeck, O. C. Defining a Smaller RNA Substrate for Elongation Factor Tu. *Biochemistry* 34, 2545-52 (1995).
39. Davis, K. A., Lin, Y., Abrams, B. & Jayasena, S. D. Staining of cell surface human CD4 with 2'-F-pyrimidine-containing RNA aptamers for flow cytometry. *Nucleic Acids Res.* 26, 3915-3924 (1998).
40. Blank, M., Weinschenk, T., Priemer, M. & Schluesener, H. Systematic evolution of a DNA aptamer binding to rat brain tumor microvessels. Selective targeting of endothelial regulatory protein pigpen. *J. Biol. Chem.* 276, 16464-16468 (2001).
41. Bruno, J. G. & Kiel, J. L. In vitro selection of DNA aptamers to anthrax spores with electrochemiluminescence detection. *Biosensors & Bioelectronics* 14, 457-464 (1999).
42. Pan, W. et al. Isolation of virus-neutralizing RNAs from a large pool of random sequences. *Proc. Natl. Acad. Sci U.S.A.* 92, 11509-13 (1995).

After selecting an appropriate aptamer or aptamers in 120, a linker 128 is formed that includes the aptamer 124. In one aspect, the aptamer 124 may serve directly as the linker 128. In another aspect, the linker 128 may be formed by joining the aptamer 124 with one or more extensions 126.

The extension 126 may be any nucleic acid sequence that may be joined with the aptamer 124, that may undergo at least partial hybridization with one or more oligonucleotide functionalized particles, and that is compatible with the analysis 100. In this aspect, at least a portion of the base sequence of the extension 126 may be complementary to at least one oligonucleotide of one or more oligonucleotide functionalized particle. In one aspect, solid phase synthesis may be used to join the aptamer 124 with the extension 126 to form the linker 128. In another aspect, after the aptamer 124 portion of the linker 128 is synthesized, the synthesis is continued to form the extension 126. Similarly, the linker 128 may be extended with the aptamer 124 sequence.

Preferably, the extension 126 includes from 1 to 100 bases. In one aspect, at least 50, 70, or 90% of the bases present in the extension 126 are capable of hybridizing with a complementary portion of a first oligonucleotide functionalized particle, such as the TGAGTAGACACT-5' (SEQ ID NO: 43) portion of particle 336 in FIG. 3A, while at least 50, 35, 25, or 10% of the bases present in the extension are capable of hybridizing with a second oligonucleotide functionalized particle, such as particle 337 in FIG. 3A.

After selecting or synthesizing the linker 128, an aggregate 132 may be formed in 130. The aggregate 132 includes the linker 128 and oligonucleotide functionalized particles 136. Considering the physical size of its components, the aggregate 132 may be quite large.

The linker 128 hybridizes with the oligonucleotide functionalized particles 136 and includes the aptamer 124 and may include the extension 126. For example, if first and second oligonucleotide functionalized particles have base sequences of 3'-AAAAAAAAAAAATGAGTAGACACT (SEQ ID NO: 44) and 5'-CCCAGGTTCTCT (SEQ ID NO. 45), respectively, an appropriate sequence for the linker 128 that includes the aptamer 124 that folds in the presence of an adenosine analyte and the extension 126 may be 5'-ACT-CATCTGTGAAGAGAACCTGGGGGAGTAT-TGCGGAGGAAGGT (SEQ ID NO. 46).

For the adenosine analyte, the extension 126 portion of the linker 128 is the ACTCATCTGTGAAGAGA (SEQ ID NO: 47) portion of the sequence, which allows the extension 126 to hybridize with twelve bases of the first functionalized particle and five bases of the second functionalized particle. Similarly, the aptamer 124 portion of the linker 128 is the ACCTGGGGGAGTATTGCGGAGGAAGGT (SEQ ID NO: 18) portion of the sequence, which allows the ACCTGGG (SEQ ID NO: 48) portion of the aptamer 124 to hybridize with the TGGACCC (SEQ ID NO: 49) portion of the second functionalized particle.

Because the particles 136 demonstrate distance-dependent optical properties, the particles are one color when closely held in the aggregate 132 and undergo a color change as the distance between the particles increases. For example, when the particles 136 are gold nanoparticles, the aggregate 132 displays a blue color in aqueous solution that turns red as disaggregation proceeds.

Disaggregation occurs when the aptamer 124 portion of the linker 128 binds with and folds in response to the analyte 105. When the aptamer 124 folds, a portion of the hybridization with the second oligonucleotide functionalized particles is lost. This hybridization loss allows the second oligonucleotide functionalized particles to separate from the aggregate 132. Thus, as the particles 136 diffuse away from the aggregate 132, the solution changes from blue to red.

The particles 136 may be any species that demonstrate distance-dependent optical properties and are compatible with the operation of the sensor system. Suitable particles may include metals, such as gold, silver, copper, and platinum; semiconductors, such as CdSe, CdS, and CdS or CdSe coated with ZnS; and magnetic colloidal materials, such as those described in Josephson, Lee, et al., *Angewandte Chemie*, International Edition (2001), 40(17), 3204-3206. Specific useful particles may include ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, and GaAs.

In a preferred aspect, the particles are gold (Au) nanoparticles and have an average diameter from 5 to 70 nanometers (nm) or from 10 to 50 nm. In a more preferred aspect, gold nanoparticles having an average diameter of from 10 to 15 nm are functionalized to the oligonucleotides.

For a more detailed treatment of how to prepare oligonucleotide functionalized gold particles, See U.S. Pat. No. 6,361,944; Mirkin, et al., *Nature* (London) 1996, 382, 607-609; Storhoff, et al., *J. Am. Chem. Soc.* 1998, 20, 1959-1064; and Storhoff, et al., *Chem. Rev.* (Washington, D.C.) 1999, 99, 1849-1862. While gold nanoparticles are presently preferred, other species that undergo a distance-dependent color change, such as inorganic crystals, quantum dots, and the like also may be attached to oligonucleotides.

In 140 the aggregate 132 may be combined with the sample 102. In 150 the sample 102 is monitored for a color change. If a color change does not occur, then the analyte 105 is not present in the sample 102. If a color change does occur in 160, the analyte 105 is present in the sample 102. The color change signifies that the analyte 105 caused the aptamer 124 to fold, thus allowing the particles 136 to diffuse away from the aggregate 132 and into the solution of the sample 102. Thus, the analysis 100 provides a "light-up" sensor system because a color change occurs in the presence of the analyte 105.

The rate at which a substantially complete color change occurs in response to the analyte 105 may be considered the response time of the sensor system. In one aspect, the color change may be considered substantially complete when the absorption peak in the visible region increases by 20%. In another aspect, the color change may be considered substantially complete when the extinction coefficient at 522 nm over 700 nm increases by 100% for gold particles. Preferable response times for the sensor system are from 1 second to 60 minutes or from 2 seconds to 10 minutes. More preferable response times for the sensor system are from 5 seconds to 2 minutes or from 8 to 12 seconds. Preferable temperature ranges for operation of the sensor system are from 0° to 60° or from 15° to 40° C. More preferable ranges for operation of the sensor system are from 23° to 37° or from 25° to 30° C. In another aspect, when the analysis 100 is conducted from 23° to 37° C., a preferable response time may be less than 2 minutes or from 1 to 12 seconds.

The degree the color changes in response to the analyte 105 may be quantified by colorimetric quantification methods known to those of ordinary skill in the art in 170. Various color comparator wheels, such as those available from Hach Co., Loveland, Colo. or LaMotte Co., Chestertown, Md. may be adapted for use with the present invention. Standards containing known amounts of the selected analyte may be analyzed in addition to the sample to increase the accuracy of the comparison. If higher precision is desired, various types of spectrophotometers may be used to plot a Beer's curve in the desired concentration range. The color of the sample may then be compared with the curve and the concentration of the analyte present in the sample determined. Suitable spectrophotometers include the Hewlett-Packard 8453 and the Bausch & Lomb Spec-20.

In yet another aspect, the method 100 may be modified to determine the sensitivity and selectivity of an aptamer to the analyte 105. In this aspect, one or more DNA strand suspected of being an aptamer responsive to the analyte 105 is selected in 120. The DNA strand may or may not be modified with the extension 126 in 125. In 130, an aggregate is formed from the DNA strands and appropriate particles. In 140, the aggregates are combined with the analyte 105. If the aggregate undergoes a color change, then the DNA strand is an appropriate aptamer sequence for the target 105. In this manner, multiple aptamers selected in 120 may be tested for use in a colorimetric sensor system.

Figure 2A:
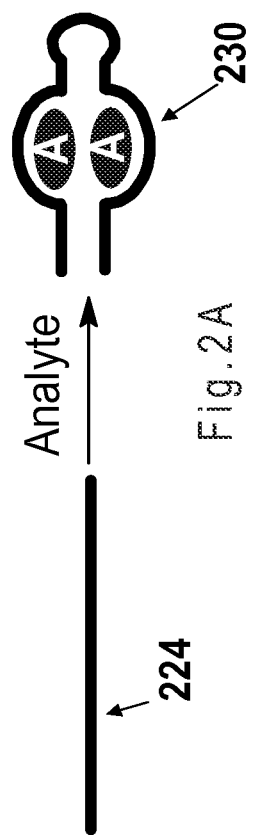
FIG. 2A depicts an aptamer that depends on two analyte molecules to fold.
Figure 2B:
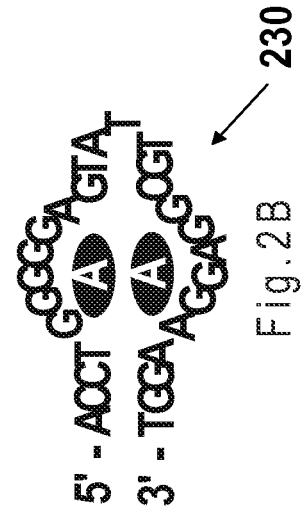
FIG. 2B depicts the base pairs for an aptamer depending on two adenosine molecules to fold (SEQ ID NO: 57).

FIG. 2A depicts an aptamer 224 that depends on two analyte molecules to undergo a conformational change to adopt a folded structure 230. FIG. 2B depicts the specific base pairs of the aptamer 224 that forms the folded structure 230 in response to two adenosine molecules. While this specific aptamer sequence relies on two molecules of the adenosine analyte to fold, other aptamers may fold in response to a single analyte molecule.

Figure 2C:
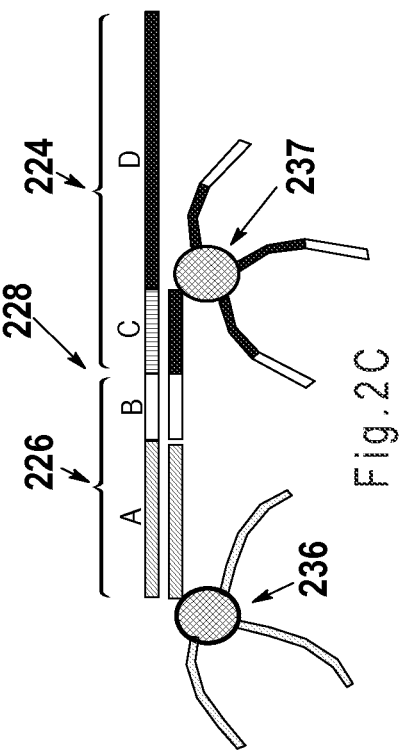
FIG. 2C depicts an aptamer joined to an extension to form a linker.

FIG. 2C depicts the aptamer 224 joined to an extension 226 to form a linker 228. The extension 226 includes A and B portions, where the A portion includes enough complementary bases to form stable hybridization with the oligonucleotide of a first particle 236. For example, a non-complementary poly-adenine chain ($A_{12}$) including 12 adenine bases may be appended to the complementary sequence of the first particle 236 to enhance hybridization stability. The sequence for the B portion of the extension 226 may be selected to eliminate linkers that inherently form stable secondary structures. A computer program, such as M-fold available at (www.bioinfospi.edu/applications/mfold/) (M. Zuker. Mfold web server for nucleic acid folding and hybridization prediction. *Nucleic Acids Res.* 31 (13), 3406-15, (2003)) or others, may be used to predict stable linkers for elimination. For example if a stable sequence for a linker is ACTCATCTGTGAAGA TGACCTGGGGGAGTATTGCGGAGGAAGGT (SEQ ID NO: 50), by substituting the underlined TG bases for GA bases to give the sequence ACTCATCTGTGAAGAGAACCTGGGGGAGTATTGCGGAGGAAGGT (SEQ ID NO: 51), the linker may be rendered inherently unstable.

The aptamer 224 includes C and D portions. In one aspect, the hybridization stability of the combined B portion of the extension 226 and the C portion of the aptamer 224 with the second particle 237 may be less than that for A and the first particle 236. In a preferred aspect, the melting temperature of this C+B/second particle hybridization is higher than the temperature at which the sensor system is to be used. In another preferred aspect, the melting temperature of a B portion hybridized to the oligonucleotide sequence of the second particle 237 is less than the temperature at which the sensor system is to be used. In another preferred aspect, the stability of a C+D+analyte complex should be greater than the hybridization stability of C with the second particle 237. In another aspect, the sequences of B and C are as short as is compatible with the operation of the sensor system.

Figure 3A:
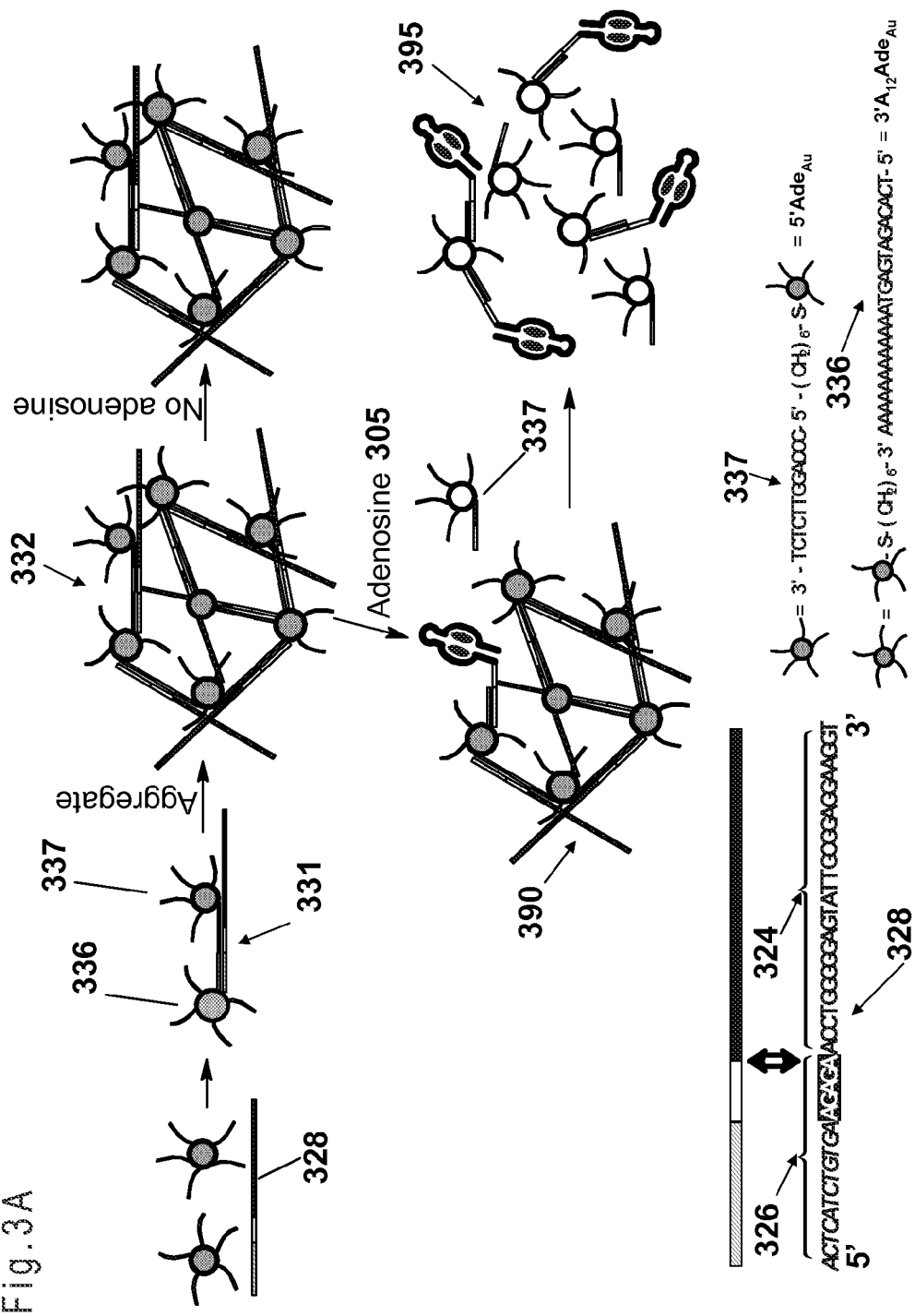
FIG. 3A represents the disaggregation of an aggregate in the presence of an adenosine analyte (SEQ ID NOS: 46, 45, 44).

FIG. 3A depicts the disaggregation of an aggregate 332 in the presence of an adenosine analyte 305. The aggregate 332 is formed from multiple aggregate units 331. Each of the aggregate units 331 is formed from a linker 328, which is hybridized to the 3' and 5' thiol-oligonucleotide functionalized particles 336 and 337, respectively. The linker 328 includes an aptamer portion 324 and an extension portion 326. The 3'-$A_{12}$Ade$_{Au}$ (SEQ ID NO: 44) particle 336 hybridizes with the extension 326, while the 5'-Ade$_{Au}$ particle 337 hybridizes with the extension 326 and the aptamer 324 to from the aggregate unit 331.

While one base sequence for the linker and the particles are shown, the bases may be changed on the opposing strands to maintain the pairings. For example, any cytosine in the A or B portions of the linker 228 may be changed to thymine, as long as the paired base of the particle oligonucleotide is changed from guanine to adenine.

In the presence of the adenosine analyte 305, the aptamer portion 324 of the linker 328 folds, thus eliminating at least a portion of the hybridization between the aptamer portion 324 of the linker 328 and the 5'-Ade$_{Au}$ particle 337. This loss of hybridization between the aptamer 324 and the 5'-Ade$_{Au}$ particle 337 releases the 5'-Ade$_{Au}$ particle to the solution.

As the 5'-Ade$_{Au}$ particles 337 are released, the blue aggregate 332 begins to disaggregate to form partial aggregate 390. This partial disaggregation adds red color to the blue solution as the particles 337 diffuse away from the aggregate 332, thus giving a purple solution. If enough of the adenosine analyte 305 is present in the sample, the reaction will continue until the aggregate 332 is completely disaggregated, to give 395. Complete disaggregation results in a red solution due to the greater distance between the particles 336, 337.

The alignment of the particles 336, 337 (tail-to-tail, head-to-tail, or head-to-head) with respect to each other may influence how tightly the aggregate units 331 bind. FIG. 3B depicts the aggregate unit 331 formed when the functionalized particles, such as 336 and 337, hybridize to the linker 328 in a tail-to-tail arrangement. Head-to-tail (FIG. 3C) or head-to-head (FIG. 3D) hybridization may be selected by reversing one or both ends of the oligonucleotide to which the particle is attached, respectively. Thus, by reversing the 3' attachment of functionalized particle 336 to 5', particle 338 may hybridize to give the head-to-tail alignment of FIG. 3C. Similarly by reversing the 3' attachment of the functionalized particle 336 to the 5' attachment of the particle 338 and by reversing the 5' attachment of the particle 337 to the 3' attachment of particle 339, the particles 338, 339 may hybridize to give the head-to-head alignment of FIG. 3D.

At present, the tail-to-tail hybridization arrangement of FIG. 3B is preferred because the head-to-tail and head-to-head hybridization arrangements of FIGS. 3C and 3D may produce aggregates that sterically hinder aptamer binding and/or aggregate formation. However, this steric hindrance may be reduced through a reduction in the average diameter of the particles or by increasing the number of bases functionalized to the particles and the length of the extension, for example.

While not shown, the methodology of FIG. 3A may be applied to other analytes, including potassium ions, cocaine, and the analytes listed above in Table I. Table II, below, gives the base sequences of the linkers and particles for adenosine, K(I), and cocaine sensor systems. The aptamer portion of each linker is presented in uppercase, while the extension portion of each linker is presented in lowercase.

TABLE II

| Name | Sequence | SEQ ID NO: |
|---|---|---|
| Adenosine Linker | 5'-actcatctgtgaagagaACCTGGGGGAGTATTGCGGAGGAAGGT | 46 |
| 3'-$A_{12}$Ade$_{Au}$ | 3'-AAAAAAAAAAAATGAGTAGACACT | 44 |
| 5'-Ade$_{Au}$ | 5'-CCCAGGTTCTCT | 45 |
| Potassium Linker | 5'-actcatctgtgatctaaGGGTTAGGGTTAGGGTTAGGG | 52 |
| 3'-$A_{12}$K(I)$_{Au}$ | 3'-AAAAAAAAAAAATGAGTAGACACT | 44 |
| 5'-K(I)$_{Au}$ | 5'-AACCCTTAGA | 53 |
| Cocaine Linker | 5'-actcatctgtgaatctcGGGAGACAAGGATAAATCCTTCAATGAAGTGGGTCTCCC | 54 |
| 3'- $A_{12}$Coc$_{Au}$ | 3'-AAAAAAAAAAAATGAGTAGACACT | 44 |
| 5'-Coc$_{Au}$ | 5'-GTCTCCCGAGA | 55 |

The ionic strength of the sample may influence how tightly the moieties that form the aggregate bind together. Higher salt concentrations favor aggregation, thus slowing sensor response, while lower salt concentrations may lack the ionic strength necessary to maintain the aggregates. In one aspect, the sample may include or be modified with a reagent to include a monovalent metal ion concentration of 30 mM and greater. The ionic strength of the sample may be modified with Na$^+$ ions, for example. In a preferred aspect, the monovalent metal ion concentration of the sample, which contains the aggregate, is from 150 to 400 mM. At present, especially preferred monovalent metal ion concentrations are about 300 mM for adenosine and potassium analytes and about 150 mM for cocaine as an analyte. pH also may influence the aggregate binding, possibly attributable to the protonation of the polynucleotide base pairs at lower pH. In one aspect, a pH from 5 to 9 is preferred, with an approximately neutral pH being more preferred.

Thus, the performance of the sensor may be improved by adjusting the ionic strength and pH of the sample prior to combining it with the aggregate. Depending on the sample, it may be preferable to add the sample or analyte to a solution containing the aggregate (where the ionic strength and pH may be controlled) or the reverse.

The sensor system, including the aptamer, extension, and oligonucleotide functionalized particles may be provided in the form of a kit. In one aspect, the kit includes the aptamer and the extension joined to form the linker. In yet another aspect, the kit includes the extension, but excludes the aptamer, which is then provided by the user or provided separately. In this aspect, the kit also may include the reagents required to link the supplied extension with an aptamer. In this aspect, the kit also may be used to determine the specificity and/or selectivity of various aptamers to a selected analyte. Thus, the kit may be used to select an appropriate aptamer in addition to detecting the analyte. In yet another aspect, the kit includes an exterior package that encloses a linker and oligonucleotide functionalized particles.

One or more of these kit components may be separated into individual containers, or they may be provided in their aggregated state. If separated, the aggregate may be formed before introducing the sample. Additional buffers and/or pH modifiers may be provided in the kit to adjust the ionic strength and/or pH of the sample.

The containers may take the form of bottles, tubs, sachets, envelopes, tubes, ampoules, and the like, which may be formed in part or in whole from plastic, glass, paper, foil, MYLAR®, wax, and the like. The containers may be equipped with fully or partially detachable lids that may initially be part of the containers or may be affixed to the containers by mechanical, adhesive, or other means. The containers also may be equipped with stoppers, allowing access to the contents by syringe needle. In one aspect, the exterior package may be made of paper or plastic, while the containers are glass ampoules.

The exterior package may include instructions regarding the use of the components. Color comparators; standard analyte solutions, such as a 10 μm solution of the analyte; and visualization aids, such as thin layer chromatography (TLC) plates, test tubes, and cuvettes, also may be included. Containers having two or more compartments separated by a membrane that may be removed to allow mixing may be included. The exterior package also may include filters and dilution reagents that allow preparation of the sample for analysis.

In another aspect, in addition to the sensor system of the present invention, the kit also may include multiple sensor systems to further increase the reliability of analyte determination and reduce the probability of user error. In one aspect, multiple light-up sensor systems in accord with the present invention may be included. In another aspect, a "light-down" sensor system may be included with the light-up sensor system of the present invention. Suitable light-down sensors for inclusion in the presently claimed kit may rely on DNAzyme/Substrate/particle aggregates that are not formed in the presence of the selected analyte. A more detailed description of suitable light-down sensor systems for inclusion in the presently claimed kit may be found, for example, in U.S. patent application Ser. No. 10/756,825, filed Jan. 13, 2004, entitled "Biosensors Based on Directed Assembly of Particles," which is hereby incorporated by reference.

The preceding description is not intended to limit the scope of the invention to the described embodiments, but rather to enable a person of ordinary skill in the art to make and use the invention. Similarly, the examples below are not to be construed as limiting the scope of the appended claims or their equivalents, and are provided solely for illustration. It is to be understood that numerous variations can be made to the procedures below, which lie within the scope of the appended claims and their equivalents.

EXAMPLES

All DNA samples were purchased from Integrated DNA Technology Inc., Coralville, Iowa. The DNA samples that formed the extensions were purified by gel electrophoresis, while the thiol-modified DNA samples for forming the oligonucleotide functionalized particles were purified by standard desalting. Adenosine, cytidine, uridine, guanosine and cocaine were purchased from Aldrich. Gold nanoparticles having an average diameter of 13 nm were prepared and functionalized with 12-mer thiol-modified DNA following literature procedures, such as those disclosed in Storhoff, J., et al., "One-pot colorimetric differentiation of polynucleotides with single base imperfections using gold particle probes," *JACS* 120: 1959-1964 (1998), for example. The average diameter of the gold nanoparticles was verified by transmission electronic microscope (JEOL 2010).

Example 1

Preparation of a Colorimetric Adenosine Sensor

Five-hundred microliters of 5'-$Ade_{Au}$ (extinction at 522 nm equals 2.2) and 500 μL of 3'-$A_{12}Ade_{Au}$ (SEQ ID NO: 44) (extinction at 522 nm equals 2.2) were mixed in the presence of 300 mM NaCl, 25 mM Tris acetate buffer, pH 8.2, and 100 nM of the adenosine aptamer/extension (Adenosine Linker). The sample was warmed to 65° C. for one minute and then allowed to cool slowly to 4° C. The nanoparticles changed color from red to dark purple during this process. The sample was centrifuged and the precipitates were collected and then dispersed in 2000 μL of the same buffer (300 mM NaCl, 25 mM Tris acetate, pH 8.2). The suspension was used for detection of adenosine.

Example 2

Colorimetric Detection of Adenosine

One-hundred microliters of the sensor suspension from Example 1 was added to a small volume of concentrated adenosine solution. For example, 2 μL of 50 mM adenosine was added to give a final concentration of 1 mM. The color change was monitored with a UV-vis spectrometer or by the naked eye.

Example 3

Monitoring the Performance of the Adenosine Sensor

Figure 4:
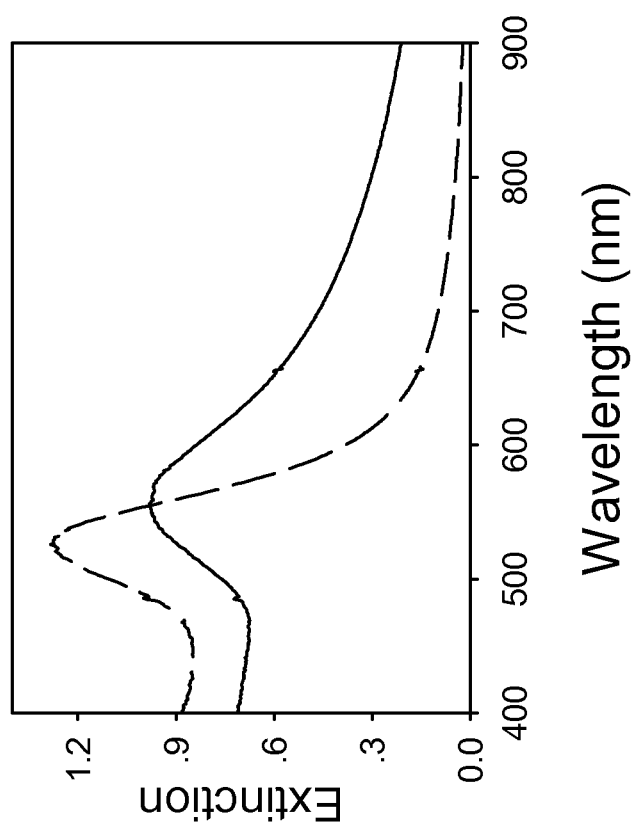
FIG. 4 is a graph relating extinction ratios to the wavelengths of light emitted from a sample by aggregated (solid line) and disaggregated (dashed line) gold nanoparticles.

The color change of the sample from Example 2 was monitored by UV-vis extinction spectroscopy. FIG. 4 is a graph relating the extinction ratios provided at specific wavelengths from a sample during disaggregation. The dashed line in FIG. 4 shows the strong extinction peak at 522 nm exhibited by separated 13 nm nanoparticles, which provide a deep red color. As may be seen from the solid line in FIG. 4, upon aggregation, the 522 nm peak decreases in intensity and shifts to longer wavelength, while the extinction at 700 nm region increases, resulting in a red-to-blue color transition. Therefore a higher extinction ratio at 522 to 700 nm is associated with the red color of separated nanoparticles, while a low extinction ratio is associated with the blue color of aggregated nanoparticles. This extinction ratio was used to monitor the aggregation state of the particles.

Example 4

Selectivity and Sensitivity of the Adenosine Sensor

To a quarts UV-vis spectrophotometer cell (Hellma, Germany) was added 100 μL of the adenosine sensor system prepared in Example 1. A small volume (1-5 µL) of solutions including adenosine, uridine, cytidine or guanosine was added to the spectrophotometer cell to bring the analyte concentration to the desired level in the cell.

Figure 5A:
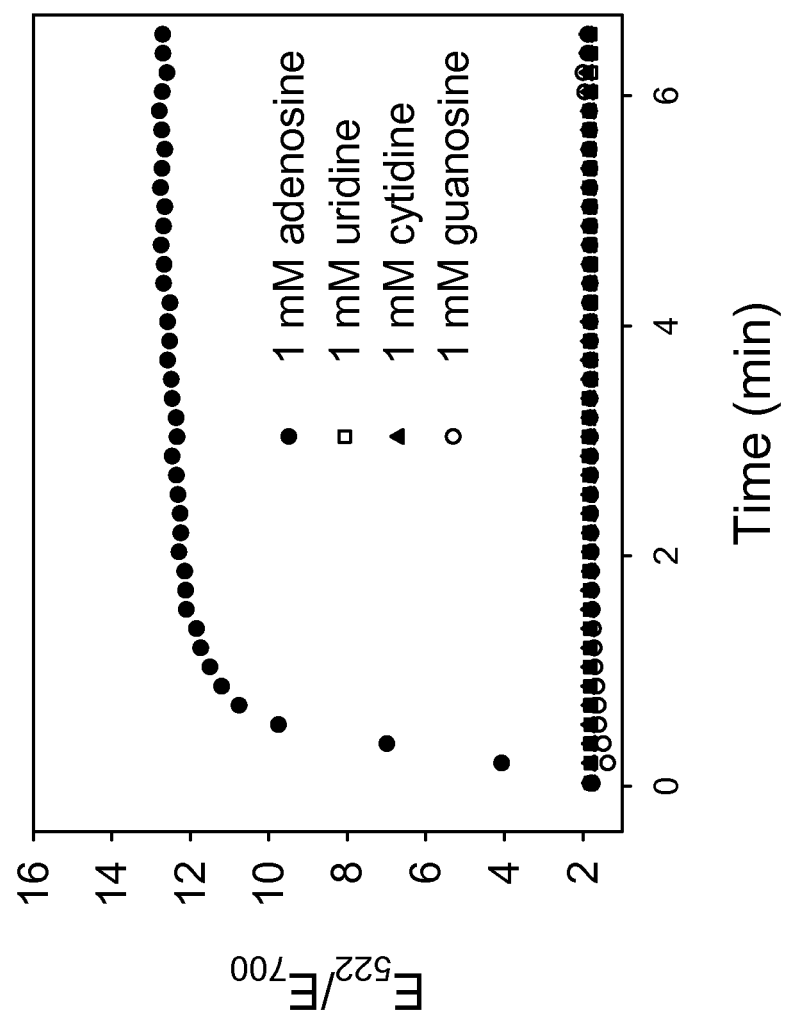
FIG. 5A is a graph showing the change in extinction ratios over time for samples containing guanosine (○), cytidine (▲), uridine (□), and adenosine (●).

The dispersion kinetics for each cell was monitored as a function of time using a Hewlett-Packard 8453 spectrophotometer. FIG. 5A is a graph depicting the ratios of extinction at 522 and 700 nm plotted as a function of time. As may be seen from the plots, only adenosine gave significant increase in the extinction ratio as a function of time, while uridine, cytidine, and guanosine provided a color change consistent with the background. Therefore, the high selectivity of the sensor was confirmed.

Figure 5B:
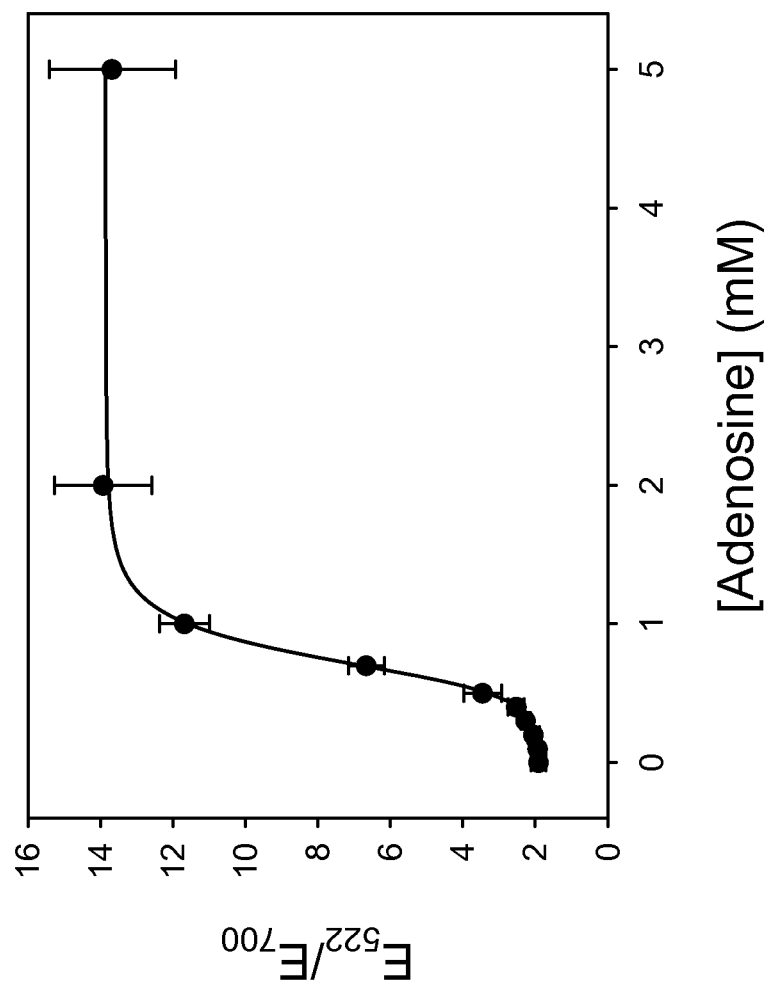
FIG. 5B is a graph depicting the correlation between the observed extinction ratios for the color change of the sensor system and the concentration of the adenosine analyte after one minute.

FIG. 5B is a graph depicting the correlation between the observed extinction ratios for the color change of the sensor system and the concentration of the adenosine analyte after five minutes of aggregation. The exceptional linearity of the sensor system was evident from about 0.1 to about 1.5 mM.

FIG. 5C is a graph depicting the extinction ratios for multiple adenosine analyte concentrations over a 6 minute time period. The graph demonstrates the ability of the sensor system to effectively differentiate between different analyte concentrations within a few minutes. Thus, the ability of the sensor system to provide accurate quantitative information was established.

In addition to the instrumental method of FIG. 5B, the color developed by the sensor was conveniently observed visually. A color progression from blue to red was seen as the adenosine concentration increased from 0 to 2 mM. Uridine, cytidine, and guanos provided a color similar to the background.

Example 5

Preparation of a Colorimetric Potassium Ion Sensor

Figure 6A:
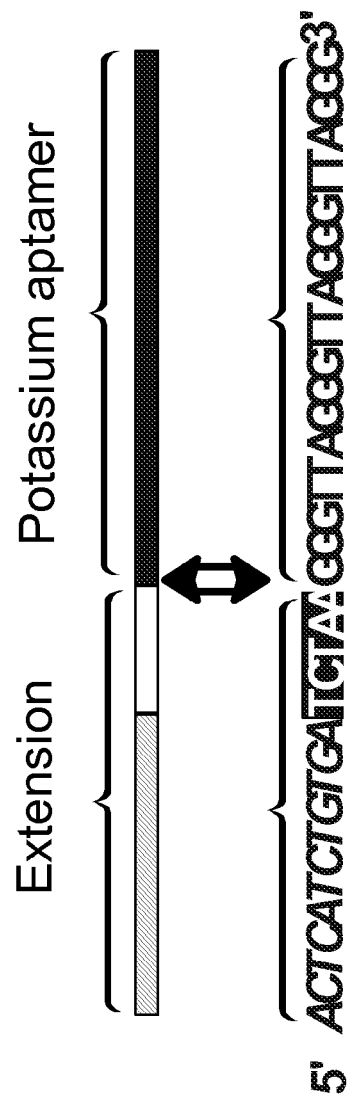
FIG. 6A provides the sequences of the extension and aptamer portions of a linker and of the oligonucleotide functionalized particles for a potassium ion sensor system (SEQ ID NOS: 52, 53, and 44, respectively in order of appearance).
Figure 6A:
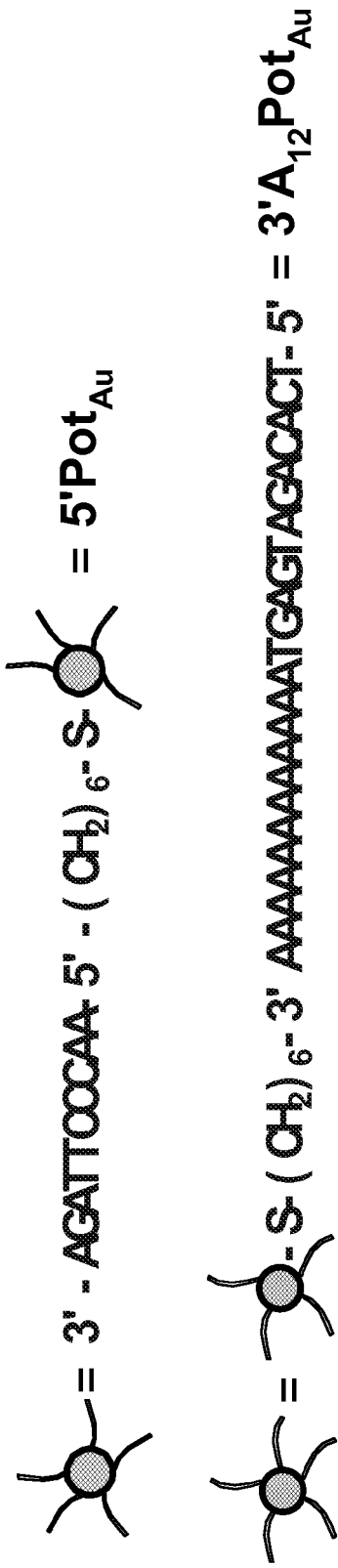
Figure 6B:
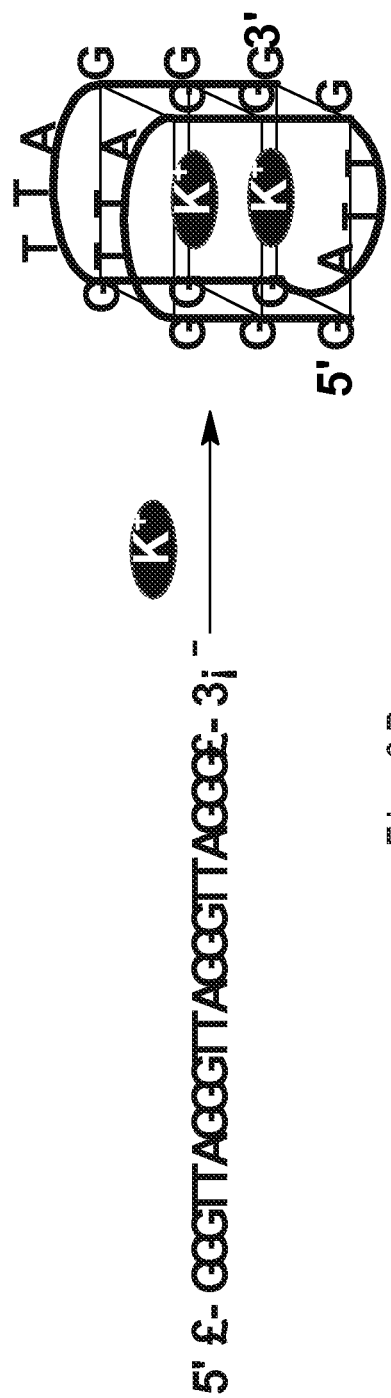
FIG. 6B depicts the aptamer folding in the presence of the K(I) analyte (SEQ ID NO: 1).

FIGS. 6A-6B represent an analyte sensor system that includes an aptamer that folds in the presence of K(I). FIG. 6A provides the sequences of the extension and aptamer portions of a linker and of the oligonucleotide functionalized particles. FIG. 6B depicts the aptamer folding in the presence of the K(I) analyte. To prepare the K(I) sensor system, 500 µL of 5'-K(I)$_{Au}$ (extinction at 522 nm equals 2.2) and 500 µL of 3'-A$_{12}$K(I)$_{Au}$ (SEQ ID NO: 44) (extinction at 522 nm equals 2.2) were mixed in the presence of 300 mM NaCl, 25 mM Tris acetate buffer, pH 8.2, and 100 nM of the potassium ion aptamer/extension (Potassium Linker). The sample was warmed to 65° C. for one minute and then allowed to cool slowly to 4° C. The nanoparticles changed color from red to dark purple during this process. The sample was centrifuged and the precipitates were collected and dispersed in 10 µL of the same buffer (300 mM NaCl, 25 mM Tris acetate, pH 8.2). The suspension was used for detection of K$^+$.

Example 6

Colorimetric Detection of Potassium

Figure 6C:
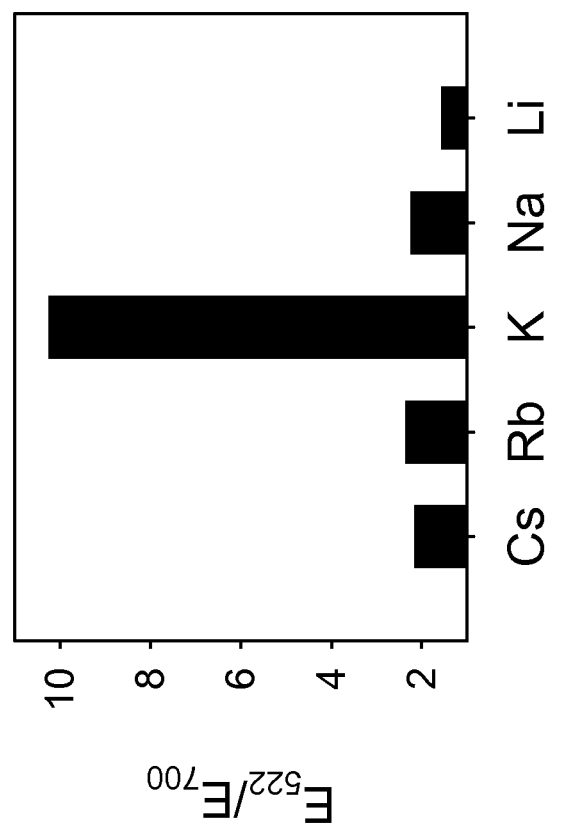
FIG. 6C depicts the extinction ratio of the potassium ion sensor for multiple metal ions.

Metal ion solutions of Li$^+$, Na$^+$, K$^+$, Rb$^+$, or Cs$^+$ ions were made by dissolving LiCl, NaCl, KCl, RbCl or CsCl salt, respectively, in deionized water to obtain an ion concentration of 3 M. From these metal ion stock solutions were prepared solutions containing 25 mM of Tris acetate buffer, pH 8.2, and 300 mM of Li$^+$, Na$^+$, K$^+$, Rb$^+$, or Cs$^+$ ions. To each of these five solutions was added 1 µL of the K(I) sensor system from Example 5 for each 99 µL of the metal ion containing solution. Therefore, each solution contained ~300 mM of Li$^+$, Na$^+$, K$^+$, Rb$^+$, or Cs$^+$ metal ions and an additional 3 mM of Na$^+$ ions as background. Each sample was heated to 65° C. and then cooled slowly to 4° C. in 1 hour. The color change was monitored with a UV-vis spectrometer or by the naked eye. FIG. 6C depicts the extinction ratio of the potassium ion sensor system in the presence of Li$^+$, Na$^+$, K$^+$, Rb$^+$, or Cs$^+$ ions, thus confirming the selectivity of the sensor system to K(I).

Example 7

Preparation of a Colorimetric Cocaine Sensor

Figure 7A:
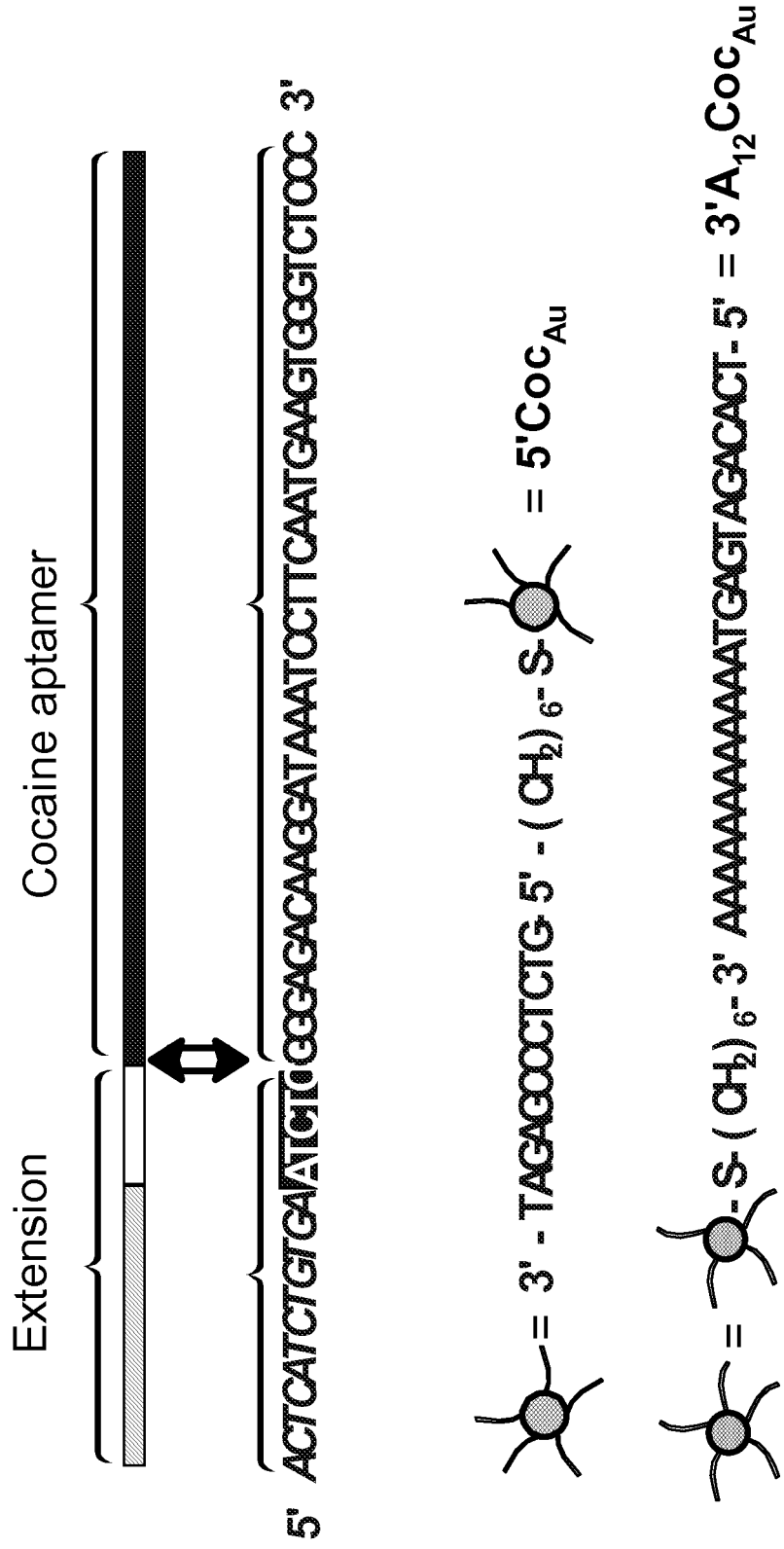
FIG. 7A provides the sequences of the extension and aptamer portions of a linker and of the oligonucleotide functionalized particles for a cocaine sensor system (SEQ ID NOS: 54, 58 and 44, respectively in order of appearance).
Figure 7B:
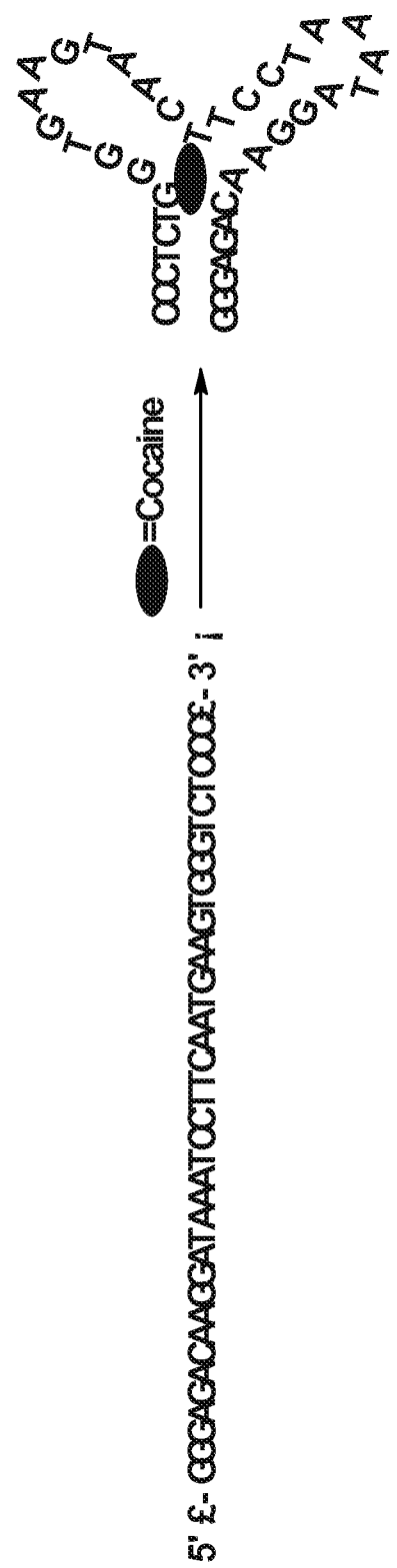
FIG. 7B depicts the aptamer folding in the presence of the cocaine analyte (SEQ ID NO: 59).

FIGS. 7A-7B represent an analyte sensor system that includes an aptamer that folds in the presence of cocaine. FIG. 7A provides the sequences of the extension and aptamer portions of the linker and of the oligonucleotide functionalized particles. FIG. 7B depicts the aptamer folding in the presence of the cocaine analyte. To prepare the cocaine sensor system, 500 µL of 5'-CocAu (extinction at 522 nm equals 2.2) and 500 µL of 3'-A12CocAu (SEQ ID NO: 44) (extinction at 522 nm equals 2.2) were mixed in the presence of 300 mM NaCl, 25 mM Tris acetate buffer, pH 8.2, and 100 nM of the cocaine aptamer/extension (Cocaine Linker). The sample was warmed to 65° C. for one minute and then allowed to cool slowly to 4° C. The nanoparticles changed color from red to dark purple during this process. The sample was centrifuged and the precipitates collected. The collected precipitates were then dispersed in 2000 µL of another buffer (150 mM NaCl, 25 mM Tris acetate, pH 8.2. The suspension was used for detection of cocaine.

Example 8

Colorimetric Detection of Cocaine

One-hundred microliters of the above prepared cocaine sensor suspension were combined with a small volume of concentrated cocaine solution. For example, 1 µL of 100 mM cocaine was added to the suspension to give a final concentration of 1 mM. The color change was monitored with a UV-vis spectrometer or by the naked eye.

Example 9

Selectivity and Sensitivity of the Cocaine Sensor

To a quarts UV-vis spectrophotometer cell (Hellma, Germany) was added 100 µL of the cocaine sensor system prepared in Example 7. A small volume (0.5-2 µL) of solutions including cocaine, adenosine, or sucrose was added to the spectrophotometer cell to bring the analyte concentration to the desired level in the cell.

Figure 8A:
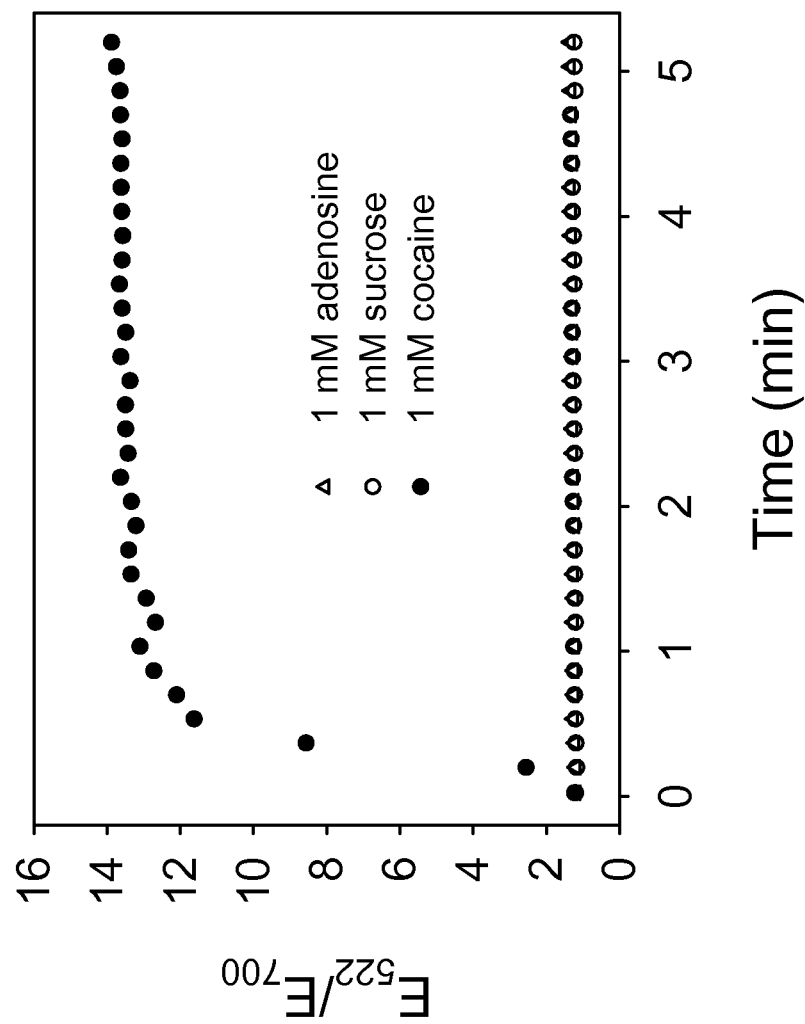
FIG. 8A is a graph showing the change in extinction ratios over time for samples containing adenosine (Δ), sucrose (○), and cocaine (●).

The dispersion kinetics for each cell was monitored as a function of time using a Hewlett-Packard 8453 spectrophotometer. FIG. 8A is a graph depicting the ratios of extinction at 522 and 700 nm plotted as a function of time. As may be seen from the plots, only cocaine gave a significant increase in the extinction ratio as a function of time, while adenosine and sucrose provided a color change consistent with the background. Therefore, the high selectivity of the sensor was confirmed.

FIG. 8B is a graph depicting the correlation between the observed extinction ratios for the color change of the sensor system and the concentration of the cocaine analyte after one minute of aggregation. The exceptional linearity of the sensor system was evident from about 0.1 to about 1 mM.

Figure 8C:
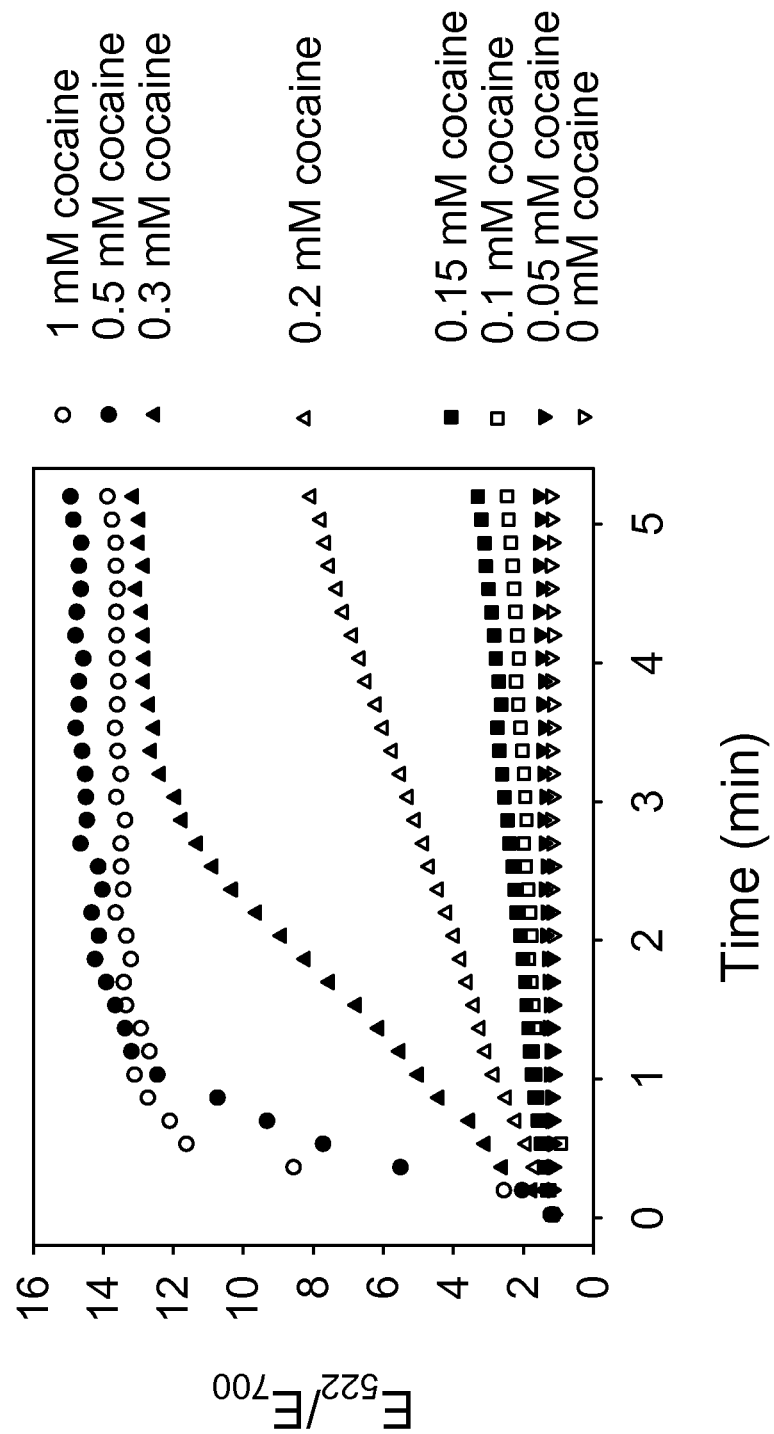
FIG. 8C is a graph depicting the extinction ratios for multiple cocaine analyte concentrations over a 5 minute time period.

FIG. 8C is a graph depicting the extinction ratios for multiple cocaine analyte concentrations over a 5 minute time period. The graph demonstrates the ability of the sensor system to effectively differentiate between different analyte concentrations within a few minutes. Thus, the ability of the sensor system to provide accurate quantitative information was established.

In addition to the instrumental method of FIG. 8B, the color developed by the sensor was conveniently observed visually. A color progression from blue to red was seen as the cocaine concentration increased from 0 to 1 mM. Adenosine and sucrose provided a color similar to the background.

As any person of ordinary skill in the art will recognize from the provided description, figures, and examples, that modifications and changes can be made to the preferred embodiments of the invention without departing from the scope of the invention defined by the following claims and their equivalents.

What is claimed is:

1. A method of detecting an analyte, comprising:
   combining an aggregate with a sample; and
   detecting a color change responsive to the analyte in the sample, the aggregate comprising:
   a linker, wherein the linker is a single oligonucleotide comprising an aptamer that is capable of folding in response to the analyte; and
   first particles coupled to a first oligonucleotide, the first oligonucleotide complementary to at least a portion of the aptamer, wherein binding of the analyte to the aptamer causes disaggregation of the aggregate the disaggregated aggregate is detectable as a color change.

2. A method for determining the sensitivity and selectivity of an aptamer to an analyte, comprising:
   combining an aggregate with the analyte;
   detecting a color change responsive to the analyte, the aggregate comprising:
   a linker, wherein the linker is a single oligonucleotide comprising the aptamer; and
   first particles coupled to a first oligonucleotide, the first oligonucleotide complementary to at least a portion of the aptamer, wherein binding of the analyte to the aptamer causes disaggregation of the aggregate and the disaggregated aggregate are detectable as a color change; and
   determining if the aptamer folded to provide the color change, thereby determining the sensitivity and selectivity of the aptamer.

3. The method of claim 2, the aggregate further comprising second particles coupled to a second oligonucleotide, the second oligonucleotide complementary to at least a portion of an extension that forms a portion of the linker, wherein the extension comprises bases.

4. The method of claim 3, where the extension comprises from 1 to 100 bases, at least 50% of the bases complementary to the first or second oligonucleotide.

5. The method of claim 2, where the linker further comprises an extension.

6. The method of claim 3, where at least a portion of the bases forming the extension inhibit the linker from forming an inherently stable secondary structure without the analyte.

7. The method of claim 3, where a portion of the second oligonucleotide is not complementary to the extension.

8. The method of claim 3, where the hybridization stability of the aptamer in combination with the analyte is greater than the hybridization stability of a portion of the aptamer with the first oligonucleotide.

9. The method of claim 3, where the first and second particles comprise a material selected from the group consisting of metals, semiconductors, magnetizable materials, and combinations thereof.

10. The method of claim 3, where the first and second particles comprise gold.

11. The method of claim 2, where the analyte is a metal ion.

12. The method of claim 2, where the analyte is selected from the group consisting of large biomolecules, small biomolecules, and organic molecules.

13. The method of claim 2, where the linker oligonucleotide comprises a sequence selected from the group consisting of SEQ ID NOS: 46, 52, and 54.

14. The method of claim 2, where the linker oligonucleotide comprises a sequence selected from the group consisting of SEQ ID NOS: 1-42.

15. The method of claim 2 having a response time of less than 60 minutes.

16. The method of claim 2 having a response time of less than 10 minutes at 23° to 37° C.

17. The method of claim 1, wherein the first oligonucleotide is further complementary to at least a portion of an extension that forms a portion of the linker.

18. The method of claim 1, the aggregate further comprising second particles coupled to a second oligonucleotide, the second oligonucleotide complementary to at least a portion of an extension that forms a portion of the linker.

19. The method of claim 18, where the hybridization stability of the aptamer in combination with the analyte is greater than the hybridization stability of a portion of the aptamer with the second oligonucleotide.

20. The method of claim 18, where the extension comprises from 1 to 100 bases, and at least 50% of the bases are complementary to the first or second oligonucleotide.

21. The method of claim 1, where the linker further comprises an extension.

22. The method of claim 18, where the first and second particles comprise a material selected from the group consisting of metals, semiconductors, magnetizable materials, and combinations thereof.

23. The method of claim 1, where the analyte is a metal ion.

24. The method of claim 1, where the analyte is selected from the group consisting of large biomolecules, small biomolecules, and organic molecules.

25. The method of claim 1, where the linker oligonucleotide comprises a sequence selected from the group consisting of SEQ ID NOS: 46, 52, and 54.

26. The method of claim 1, where the linker oligonucleotide comprises a sequence selected from the group consisting of SEQ ID NOS: 1-42.

27. The method of claim 1, where the linker oligonucleotide comprises a variant of a sequence selected from the group consisting SEQ ID NOS: 1-42, 46, 52, 54, and wherein the variant has one or more bases of that portion of the sequence that hybridizes to the first oligonucleotide, and the corresponding bases on the first oligonucleotide are also modified to maintain hybridization pairings C-G and A-T.

28. The method of claim 2, where the linker oligonucleotide comprises a variant of a sequence selected from the group consisting SEQ ID NOS: 1-42, 46, 52, 54, and wherein the variant has one or more bases of that portion of the sequence that hybridizes to the first oligonucleotide, and the corresponding bases on the first oligonucleotide are also modified to maintain hybridization pairings C-G and A-T.

29. The method of claim 18, where the first and second particles comprise gold.

30. A method of detecting an analyte, comprising:
   combining an aggregate with a sample; and
   detecting a color change responsive to the analyte in the sample, the aggregate comprising:
   a linker, wherein the linker is a single oligonucleotide comprising an extension and an aptamer that is capable of folding in response to the analyte; and
   first particles coupled to a first oligonucleotide, the first oligonucleotide complementary to at least a portion of the aptamer,
   second particles coupled to a second oligonucleotide, the second oligonucleotide complementary to at least a portion of the extension,
   wherein binding of the analyte to the aptamer causes disaggregation of the aggregate and the disaggregated aggregate is detectable as a color change.

* * * * *

UNITED STATES PATENT AND TRADEMARK OFFICE
CERTIFICATE OF CORRECTION

PATENT NO.       : 8,470,532 B2
APPLICATION NO.  : 13/008568
DATED            : June 25, 2013
INVENTOR(S)      : Lu and Liu Page 1 of 1

It is certified that error appears in the above-identified patent and that said Letters Patent is hereby corrected as shown below:

On the Title Page, Item (56):

On page 13, 2nd column, in the Ellington *et al.* reference, "Opitical" should be --Optical--.

In the Specification:

Column 20, line 30, "pH 8.2." should be --pH 8.2).--.

In the Claims:

Column 41, line 12, claim 1, "aggregate the" should be --aggregate and the--.

Column 41, line 26, claim 2, "aggregate are" should be --aggregate is--.

Column 42, line 36, claim 27, "consisting SEQ" should be --consisting of SEQ--.

Column 42, line 43, claim 28, "consisting SEQ" should be --consisting of SEQ--.

Signed and Sealed this
Twenty-eighth Day of January, 2014

Michelle K. Lee
*Deputy Director of the United States Patent and Trademark Office*